United States Patent
Walzman

(10) Patent No.: US 11,642,211 B2
(45) Date of Patent: May 9, 2023

(54) LASSO FILTER TIPPED MICROCATHETER FOR SIMULTANEOUS ROTATING SEPARATOR, IRRIGATOR FOR THROMBECTOMY AND METHOD FOR USE

(71) Applicant: Daniel Ezra Walzman, Bergenfield, NJ (US)

(72) Inventor: Daniel Ezra Walzman, Bergenfield, NJ (US)

( * ) Notice: Subject to any disclaimer, the term of this patent is extended or adjusted under 35 U.S.C. 154(b) by 311 days.

(21) Appl. No.: 17/140,343

(22) Filed: Jan. 4, 2021

(65) Prior Publication Data
US 2021/0121281 A1   Apr. 29, 2021

Related U.S. Application Data

(63) Continuation of application No. 16/501,593, filed on May 2, 2019, now Pat. No. 11,439,492, which is a
(Continued)

(51) Int. Cl.
*A61F 2/01*   (2006.01)
*A61B 17/22*   (2006.01)
(Continued)

(52) U.S. Cl.
CPC ............... *A61F 2/013* (2013.01); *A61B 8/06* (2013.01); *A61B 8/12* (2013.01); *A61B 17/22* (2013.01); *A61B 17/2202* (2013.01); *A61B 17/22012* (2013.01); *A61B 17/3207* (2013.01); *A61B 17/32037* (2013.01);
(Continued)

(58) Field of Classification Search
CPC ...... A61F 2/013; A61F 17/22; A61F 17/3207; A61F 17/320758; A61F 2017/00876; A61F 2017/22079; A61F 2090/3966; A61F 2217/005; A61F 2217/007
See application file for complete search history.

(56) References Cited

U.S. PATENT DOCUMENTS

| 3,874,388 A | 4/1975 | King et al. |
| 4,282,875 A | 8/1981 | Serbinenko et al. |

(Continued)

FOREIGN PATENT DOCUMENTS

| AU | 2011/353593 | 12/2011 |
| WO | WO 2011/057002 | 5/2011 |
| WO | WO 2019/173475 | 9/2019 |

OTHER PUBLICATIONS

Aggarwal S., et al., "Abdominal aortic aneurysm: A comprehensive review", Exp Clin Cardiol, 2011, vol. 16, pp. 11-15.
(Continued)

*Primary Examiner* — Phong Son H Dang

(57) ABSTRACT

The invention provides a filter assembly including a string or wire such that a lasso type cincture is effected, said filter being openable and closeable while in deployed within a bodily vessel. A string lengthen or shorting adjustment mechanism, such as a ratchet or reel allows more length of string into the device or alternatively to shorten the length of available string in the system. The described invention, when used to ameliorate venous clots and most arteriovenous dialysis grafts, a filter-tipped aspirator is used downstream from the clot to capture and remove dislocated emboli. A method of using same is disclosed.

18 Claims, 33 Drawing Sheets

Related U.S. Application Data continuation-in-part of application No. 16/125,691, filed on Sep. 8, 2018, now Pat. No. 10,307,242, which is a continuation-in-part of application No. 15/731,478, filed on Jun. 16, 2017, now Pat. No. 10,314,684, which is a continuation-in-part of application No. 15/530,898, filed on Mar. 20, 2017, now Pat. No. 10,299,824, which is a continuation-in-part of application No. 15/258,877, filed on Sep. 7, 2016, now abandoned.

(51) Int. Cl.
| | |
|---|---|
| *A61B 17/3203* | (2006.01) |
| *A61B 17/3207* | (2006.01) |
| *A61B 8/06* | (2006.01) |
| *A61B 8/12* | (2006.01) |
| *A61M 25/00* | (2006.01) |
| *A61B 90/00* | (2016.01) |
| *A61B 17/00* | (2006.01) |
| *A61B 8/08* | (2006.01) |
| *A61M 25/10* | (2013.01) |

(52) U.S. Cl.
CPC ......... *A61B 17/320758* (2013.01); *A61B 17/320783* (2013.01); *A61M 25/007* (2013.01); *A61M 25/0021* (2013.01); *A61B 8/0891* (2013.01); *A61B 2017/00876* (2013.01); *A61B 2017/00955* (2013.01); *A61B 2017/22039* (2013.01); *A61B 2017/22051* (2013.01); *A61B 2017/22067* (2013.01); *A61B 2017/22079* (2013.01); *A61B 2017/22084* (2013.01); *A61B 2017/320716* (2013.01); *A61B 2017/320733* (2013.01); *A61B 2017/320775* (2013.01); *A61B 2090/3784* (2016.02); *A61B 2090/3966* (2016.02); *A61B 2217/005* (2013.01); *A61B 2217/007* (2013.01); *A61F 2/011* (2020.05); *A61F 2002/018* (2013.01); *A61M 25/0026* (2013.01); *A61M 25/0032* (2013.01); *A61M 25/0068* (2013.01); *A61M 2025/0024* (2013.01); *A61M 2025/0042* (2013.01); *A61M 2025/1052* (2013.01)

(56) References Cited

U.S. PATENT DOCUMENTS

| | | | |
|---|---|---|---|
| 4,346,712 A | 8/1982 | Handa et al. | |
| 4,402,319 A | 9/1983 | Handa et al. | |
| 4,619,246 A | 10/1986 | Nielsen et al. | |
| 4,675,361 A | 6/1987 | Ward | |
| 5,165,421 A | 11/1992 | Fleischacker et al. | |
| 5,263,963 A | 11/1993 | Garrison et al. | |
| 5,325,619 A | 7/1994 | Paul | |
| 5,334,210 A | 8/1994 | Gianturco | |
| 5,354,310 A | 10/1994 | Gamic | |
| 5,375,612 A | 12/1994 | Cottenceau | |
| 5,376,100 A | 12/1994 | Lefebvre | |
| 5,733,294 A | 3/1998 | Forber et al. | |
| 5,833,650 A | 11/1998 | Imran | |
| 5,907,893 A | 6/1999 | Zadno-Azzizi et al. | |
| 5,941,896 A | 8/1999 | Kerr | |
| 6,135,991 A | 10/2000 | Muni | |
| 6,221,006 B1 * | 4/2001 | Dubrul .................. | A61B 17/221 606/117 |
| 6,221,086 B1 | 4/2001 | Forber | |
| 6,235,044 B1 | 5/2001 | Root | |
| 6,290,710 B1 | 9/2001 | Cryer | |
| 6,306,163 B1 | 10/2001 | Fitz | |
| 6,361,545 B1 | 3/2002 | Macoviak | |
| 6,375,670 B1 | 4/2002 | Greenhalgh | |
| 6,383,206 B1 | 5/2002 | Gillick | |
| 6,454,775 B1 | 9/2002 | Demarais et al. | |
| 6,605,074 B2 | 8/2003 | Zadno-Azizi | |
| 6,605,102 B1 | 8/2003 | Mazzocci et al. | |
| 6,610,077 B1 | 8/2003 | Hancock | |
| 6,620,148 B1 | 9/2003 | Tsugita | |
| 6,673,090 B2 | 1/2004 | Root | |
| 6,676,682 B1 * | 1/2004 | Tsugita .................. | A61F 2/013 606/200 |
| 6,706,055 B2 | 3/2004 | Douk | |
| 7,575,582 B2 | 8/2009 | Gandhi et al. | |
| 7,918,820 B2 | 4/2011 | Stalker | |
| 8,038,674 B2 | 10/2011 | Schmaltz | |
| 8,361,095 B2 | 1/2013 | Osborne | |
| 8,784,434 B2 | 7/2014 | Rosenbluth | |
| 9,271,818 B2 * | 3/2016 | Urbanski .............. | A61F 2/0108 |
| 9,579,116 B1 * | 2/2017 | Nguyen ............... | A61B 17/221 |
| 9,788,825 B2 | 10/2017 | Whittaker | |
| 9,848,975 B2 * | 12/2017 | Hauser .................. | A61B 17/221 |
| 9,968,740 B2 | 5/2018 | Pinchuk | |
| 10,016,266 B2 | 7/2018 | Hauser | |
| 10,390,817 B2 * | 8/2019 | Bonutti .............. | A61B 17/0401 |
| 10,500,038 B1 | 12/2019 | Orlov | |
| 11,090,460 B2 | 8/2021 | Jaroch | |
| 11,103,263 B2 | 8/2021 | Long | |
| 2001/0039411 A1 | 11/2001 | Johansson | |
| 2002/0062119 A1 | 5/2002 | Zadno-Azizi | |
| 2002/0065507 A1 | 5/2002 | Zadno-Azizi | |
| 2002/0095171 A1 | 7/2002 | Belef | |
| 2002/0169472 A1 | 11/2002 | Douk | |
| 2002/0177800 A1 | 11/2002 | Bagaoisan | |
| 2003/0104073 A1 | 6/2003 | Johansson | |
| 2003/0150821 A1 | 8/2003 | Bates | |
| 2003/0187475 A1 | 10/2003 | Tsugita | |
| 2005/0004594 A1 | 1/2005 | Nool | |
| 2005/0080356 A1 | 4/2005 | Dapolito | |
| 2005/0245894 A1 | 11/2005 | Zadno-Azizi | |
| 2005/0277976 A1 | 12/2005 | Galdonik | |
| 2006/0200191 A1 | 9/2006 | Zadno-Azizi | |
| 2006/0253145 A1 | 11/2006 | Lucas | |
| 2006/0271060 A1 | 11/2006 | Gordon | |
| 2007/0112374 A1 | 5/2007 | Paul | |
| 2007/0156170 A1 * | 7/2007 | Hancock ................. | A61F 2/013 606/200 |
| 2007/0198028 A1 | 8/2007 | Miloslavski | |
| 2007/0208370 A1 | 9/2007 | Hauser | |
| 2008/0033341 A1 | 2/2008 | Grad | |
| 2008/0033460 A1 | 2/2008 | Ziniti | |
| 2008/0195145 A1 | 8/2008 | Bonutti | |
| 2008/0208317 A1 | 8/2008 | Jang et al. | |
| 2009/0099640 A1 | 4/2009 | Weng | |
| 2009/0149881 A1 | 6/2009 | Vale | |
| 2009/0326562 A1 | 12/2009 | White | |
| 2010/0069948 A1 | 3/2010 | Veznedaroglu et al. | |
| 2010/0211087 A1 | 8/2010 | Osborne | |
| 2010/0324665 A1 | 12/2010 | Shaw et al. | |
| 2012/0041538 A1 | 2/2012 | White | |
| 2012/0283811 A1 | 11/2012 | Neilan | |
| 2013/0030461 A1 | 1/2013 | Marks | |
| 2013/0035628 A1 | 2/2013 | Garrison | |
| 2013/0072960 A1 | 3/2013 | Schneider | |
| 2013/0204278 A1 | 8/2013 | Cully | |
| 2013/0253571 A1 | 9/2013 | Bates | |
| 2013/0281788 A1 | 10/2013 | Garrison | |
| 2013/0345617 A1 | 12/2013 | Wallace | |
| 2014/0005540 A1 | 1/2014 | Merhi | |
| 2014/0142598 A1 | 5/2014 | Fulton, III | |
| 2014/0243878 A1 | 8/2014 | Urbanski | |
| 2014/0276403 A1 | 9/2014 | Follmer | |
| 2015/0313732 A1 | 11/2015 | Fulton, III | |
| 2015/0366649 A1 | 12/2015 | Tafti | |
| 2016/0151112 A1 | 6/2016 | Ku et al. | |
| 2016/0220265 A1 | 8/2016 | Pokomey | |
| 2016/0235515 A1 | 8/2016 | Merhi | |
| 2016/0296315 A1 | 10/2016 | Yachia | |
| 2016/0317288 A1 | 11/2016 | Rogers | |
| 2017/0035445 A1 | 2/2017 | Nguyen | |
| 2017/0056169 A1 | 3/2017 | Johnson | |
| 2017/0112514 A1 | 4/2017 | Marchand | |
| 2017/0238950 A1 | 8/2017 | Yang | |

(56) References Cited

U.S. PATENT DOCUMENTS

| | | |
|---|---|---|
| 2017/0259042 A1 | 9/2017 | Nguyen |
| 2018/0256177 A1 | 9/2018 | Cooper |
| 2019/0029692 A1 | 1/2019 | Ferrera |
| 2019/0125514 A1 | 5/2019 | Amone |
| 2019/0125534 A1 | 5/2019 | Arcaro |
| 2022/0023073 A1 | 1/2022 | Shirahama |

OTHER PUBLICATIONS

Alvarez-Tostado J.A., et al., "The brachial artery: A critical access for endovascular procedures", Journal of Vascular Surgery, 2009, vol. 49, pp. 378-385.

Brekenfeld C., et al., "Impact of retrievable stents on acute ischemic stroke treatment", AJNR Am J Neuroradiol, 2011, vol. 32, pp. 1269-1273.

Brekenfeld C., et al., "Mechanical thromoembolectomy for acute ischemic stroke: Comparison of the catch thrombectomy device and the merci retriever in vivo", Stroke, 2008, vol. 39, pp. 1213-1219, American Heart Association.

Choi S.W., et al., "Low power ultrasound delivered through a PTCA-Like guidewire: Preclinical feasibility and safety of a novel technology for intracoronary thrombolysis", Journal of Interventional Cardiology, 2006, vol. 19, pp. 87-92.

Cousins T.R., et al., "Arterial cannulation: A critical review", AANA Journal, 2004, vol. 72, pp. 267-271.

Di Mario C. Techniques to enhance guide catheter support. Catheter Cardiovasc Interv 2008;72:505-512.

Fitzsimmons B.-F.M., et al., "Rapid stent-supported revascularization in acute ischemic stroke", AJNR 2006, vol. 27, pp. 1132-1134.

Fry D.L., "Acute vascular endothelial changes associated with increased blood velocity gradients", Circulation Research, 1968, vol. 22, pp. 165-197.

Fujita S. Tamai H. Kyo E. et al. New technique for superior guiding catheter support during advancement of a balloon in coronary angioplasty: The anchor technique. Catheter Cardiovasc Interv 2003; 59:482-488.

Gobin Y.P., et al., "In vitro study of hemodynamics in a giant saccular aneurysm model: influence of flow dynamics in the parent vessel and effects of coil embolization", Neuroradiology. 1994, vol. 36, pp. 530-536.

Gralla J., et al., "Mechanical thrombectomy for acute ischemic stroke: Thrombous-device interaction, efficiency, and complications in vivo", Stroke, 2006, vol. 37, pp. 3019-3024.

Graves V.B., et al., "Intracranial arteriovenous malformations: Current imaging and treatment", Investigative Radiology, 1990, vol. 25, pp. 952-960.

Hademenos G., et al., "A biomathematical model of intracranial arteriovenous malformations based on electrical network analysis; Theory and Hemodynamics", Neurosurgery, 1996, vol. 38, pp. 1005-1015.

Hademenos G.J., et al., "The Physics of Cerebral Aneurysms", Physics Today, 1995, pp. 24-30, American Institute of Physics.

Hademenos G.J., et al., "Biophysical mechanisms of stroke", Stroke, 1997, vol. 28, pp. 2067-2077.

Hademenos G.J., et al., "The biophysics of stroke", The Scientific Research Society, 1997, pp. 1-14.

Mahmood, A. Applications of the Distal Anchoring Technique in Coronary and Peripheral Interventions Cath Lab Digest Oct. 2011 vol. 19—Issue 10.

Hart R.G., et al., "Hematologic disorders and ischemic stroke: A selective review", Stroke, 1990, vol. 21, pp. 1111-1121.

Hoffman M., et al., "A cell-based model of hemostasis", Thromb Haemost, 2001, vol. 85, pp. 958-965, Schattauer GmbH, Stuttgart.

Kalyanasundaram A., et al., "Comparison of revascularization procedures in coronary artery disease", Medscape, 2011, http://emedicine.medscape.com/article/164682.

Krajcer Z., et al., "Update on endovascular treatment of peripheral vascular disease", Texas Heart Institute Journal, 2000, pp. 369-385.

Levy E., et al., "Stent-assisted intracranial recanalization for acute stroke: Early Results", Neurosurgery, 2006, vol. 58, pp. 459-463.

Manchola I., et al., "Arteriovenous malformation hemodynamics: A transcranial doppler study", Neurosurgery, 1993, vol. 33, pp. 556-562.

Mehta R., et al., "Race/ethnic differences in the risk of hemorrhagic complications among patients with ischemic stroke receiving thrombolytic therapy", Stroke, 2014, vol. 45, pp. 2263-2269.

Meyers P., et al., "Current status of endovascular stroke treatment", Circulation, 2011, vol. 123, pp. 2591-2601.

Monroe D., et al., "Platelets and thrombin generation", Arteriosclerosis, Thrombosis, and Vascular Biology, Journal of the American Heart Association, 2002, vol. 22, pp. 1381-1389.

Mordasini P., et al., "In vivo evaluation of the first dedicated combined flow-restoration and mechanical thrombectomy device in a swine model of acute vessel occlusion", AJNR, 2011, vol. 32, pp. 294-300.

Mordasini P., et al., "Experimental evaluation of immediate recanalization effect and recanalization efficacy of a new thrombus retriever for acute stroke treatment in vivo", ANJR Am J Neuroradiol, 2013, vol. 354, pp. 153-158.

Mustard J.J., et al., "Factors influencing thrombus formation in vivo", American Journal of Medicine, 1962, vol. 33, pp. 621-647.

Nogueira R.G., et al., "Endovascular approaches to acute stroke. Part 1: Drugs, Devices, and Data", AJNR Am J Neuroradiol, 2009, vol. 30, pp. 649-661.

Nogueira R.G., et al., "Endovascular approaches to acute stroke, Part 2: A comprehensive review of studies and trials", AJNR Am J Neuroradiol, 2009, vol. 30, pp. 859-875.

Nogueira R.G., et al., "Trevo versus merci retrievers for thrombectomy revascularization of large vessel occlusions in acute ischemic stroke (TREVO 2): a randomized trial", Lancet, 2012, vol. 380, pp. 1231-1240.

Ouriel K., "A history of thrombolytic therapy", Ednovasc Ther, 2004, vol. 11, pp. 128-133.

Samaniego E.A., et al., "Stenting in the treatment of acute ischemic stroke: Literature review", Frontiers in Neurology, 2011, vol. 2, pp. 1-7.

Silverberg E., et al., Cancer Statistics, 1990, vol. 40, pp. 9-26.

Singh P., et al., "Endovascular treatment of acute ischemic stroke", Journal of Neurosciences in Rural Practice, 2013, vol. 4, pp. 298-303.

Smith W.S., et al. "Safety and efficacy of mechanical embolectomy in acute ischemic stroke", Stroke, 2005, vol. 36, pp. 1432-1440.

Stein P. D., et al., "Measured turbulence and its effect on thrombus formation" Circulation Research, 1974, vol. 35, pp. 608-614.

Stone G.W., et al., "Safety and efficacy of sirolimus and paclitaxel-eluting coronary stents", The New England Journal of Medicine, 2007, vol. 356, pp. 998-1008.

"The Penumbra Pivotal Stroke", Stroke, 2009, http://stroke.ahajournals.org/content.40/8/2761.full, Crossmark.

Wilkins R.H., "Natural history of intracranial vascular malformations: A review", Neurosurgery, 1985, vol. 16, pp. 421-430.

Wilkins R.H., "Cerebral vasospasm", Contemporary Neurosurgery, 1988, vol. 10, pp. 1-6.

Yamada S., et al., "Total blood flow to arteriovenous malformations", Neurological Research, 1993, vol. 15 pp. 383-389.

Zaidat O.O., et al., "Interventional acute ischemic stroke therapy with intracranial self-expanding stent", Stroke, 2008, vol. 39, pp. 2392-2395.

\* cited by examiner

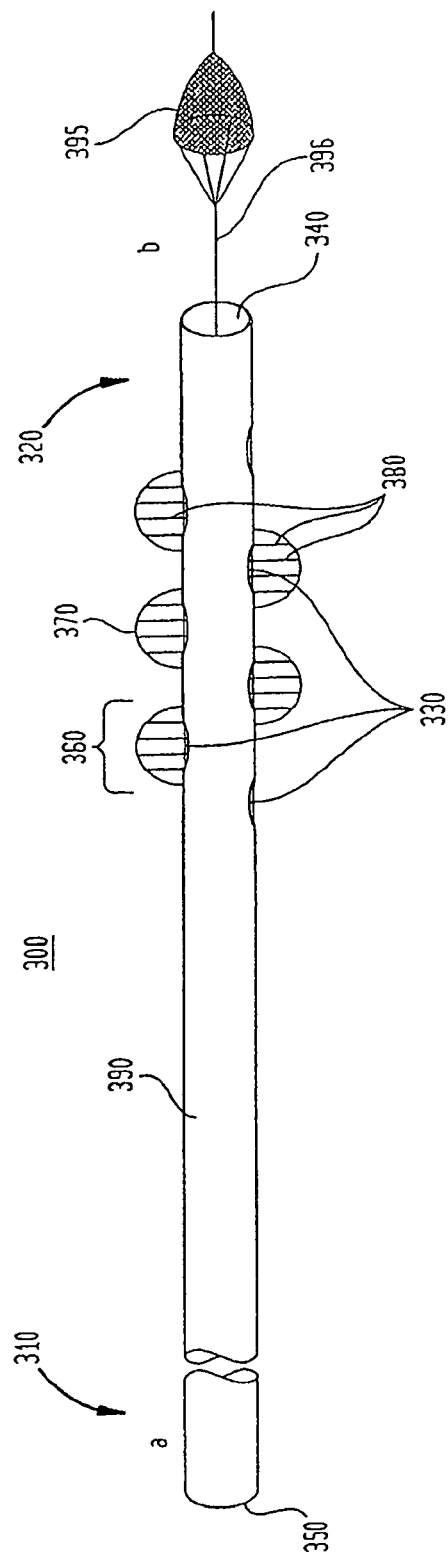

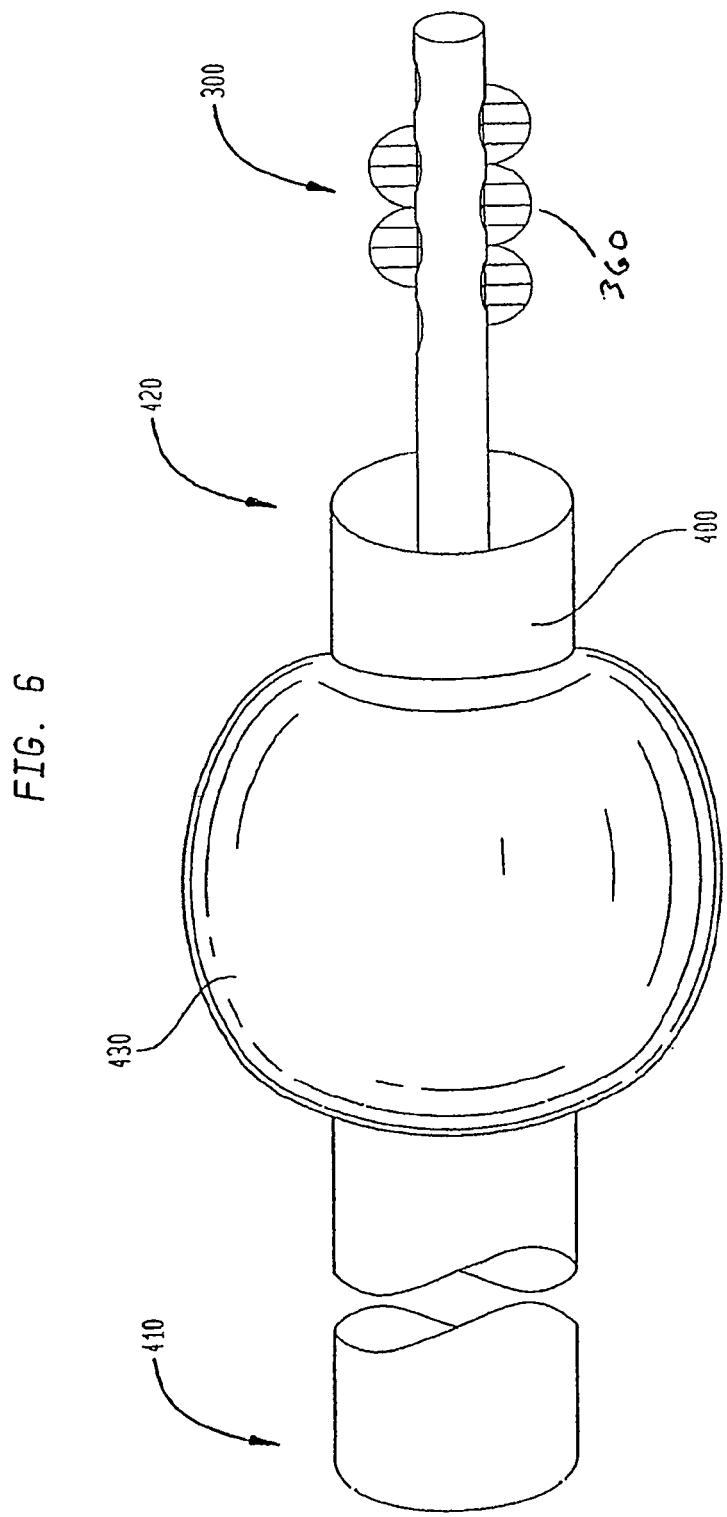

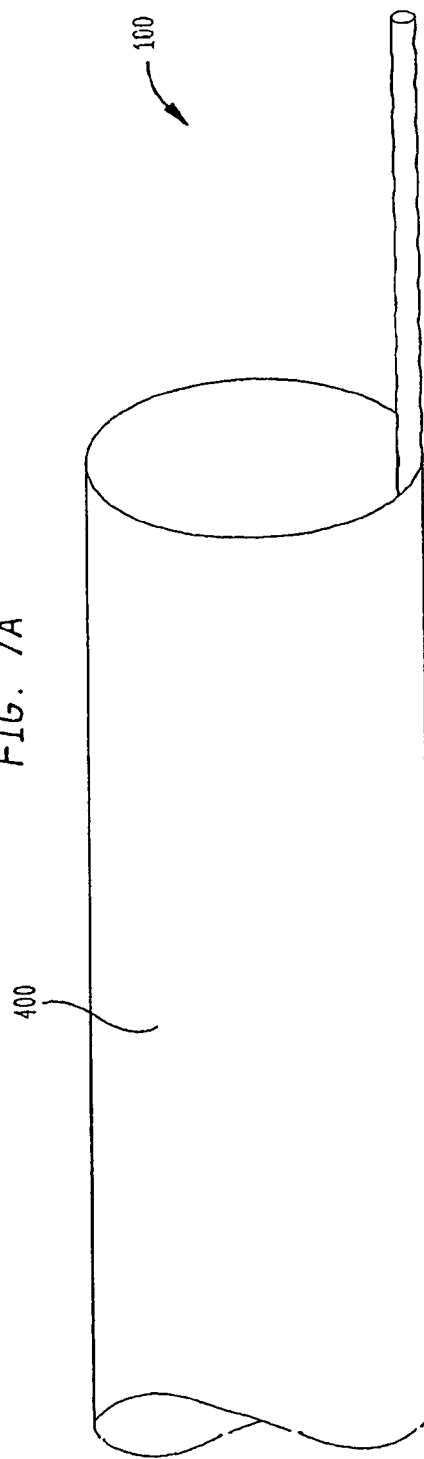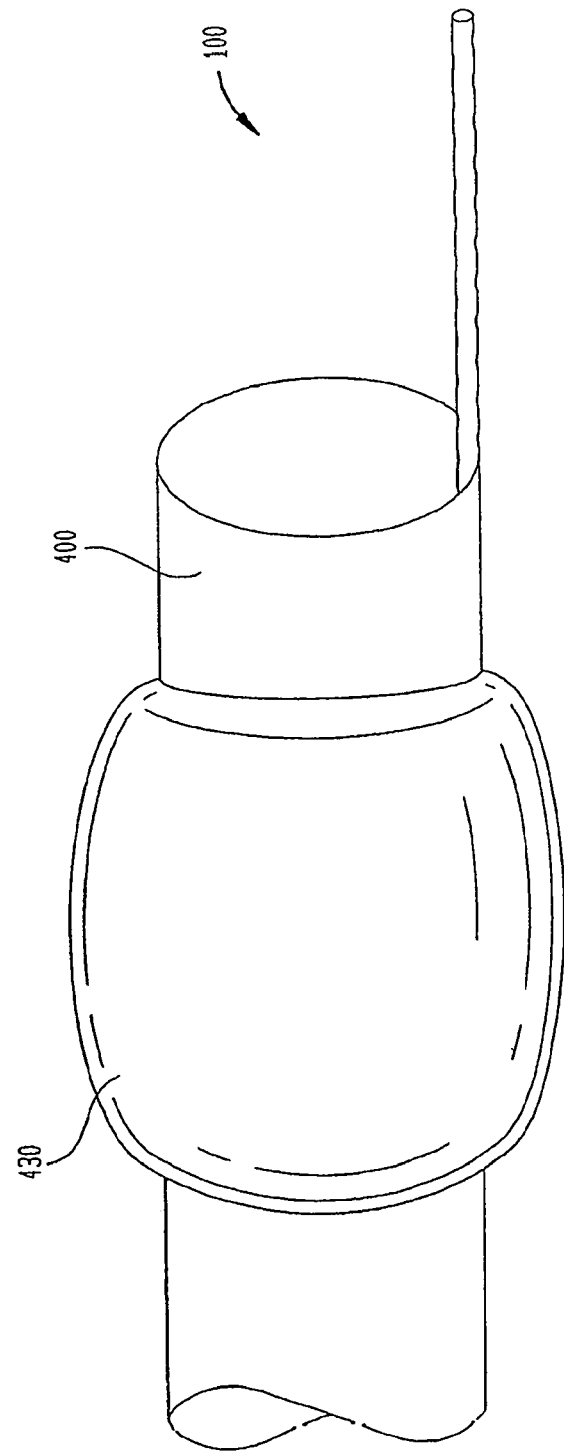

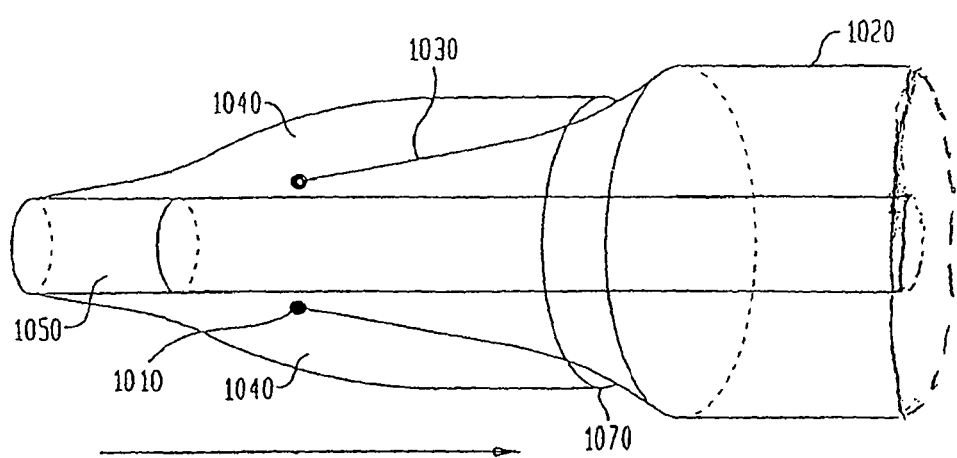
FIG. 8
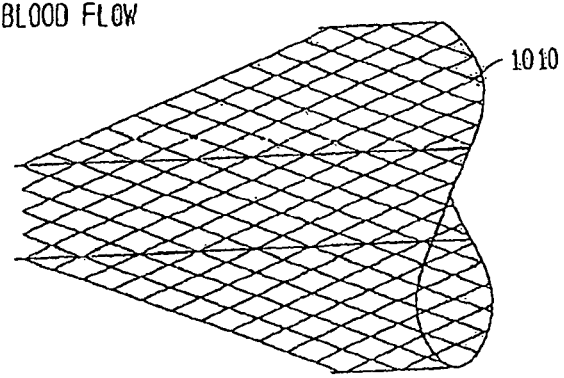
BLOOD FLOW

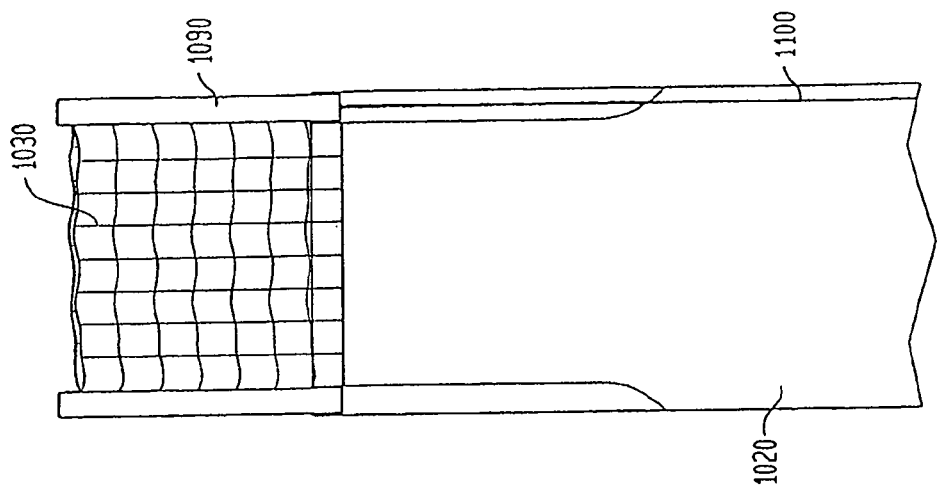
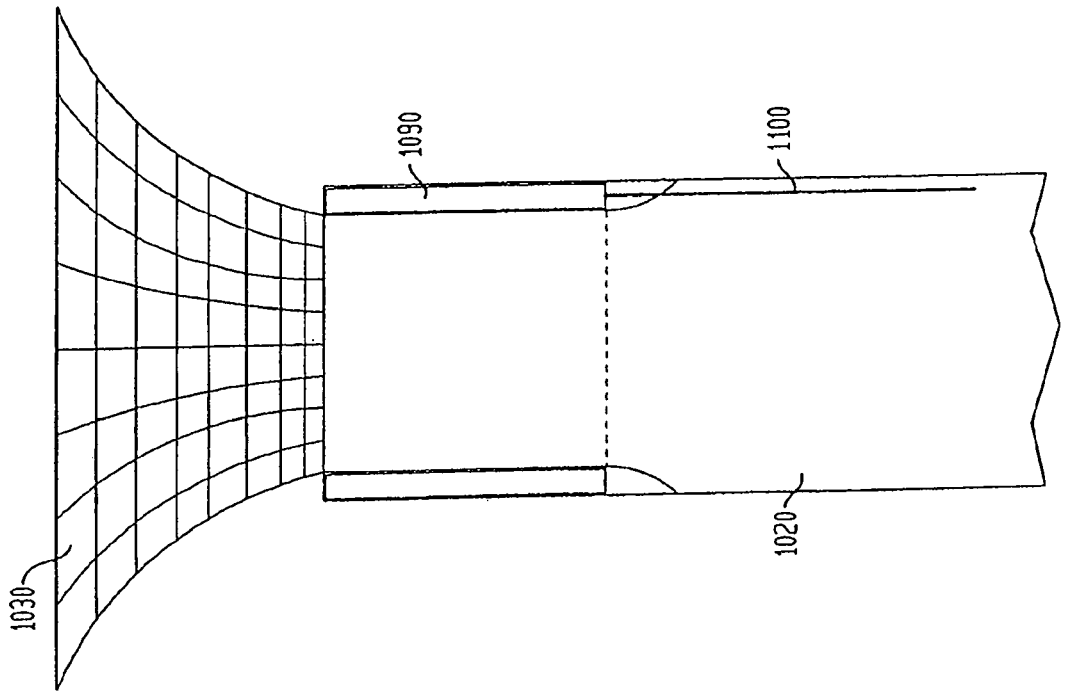

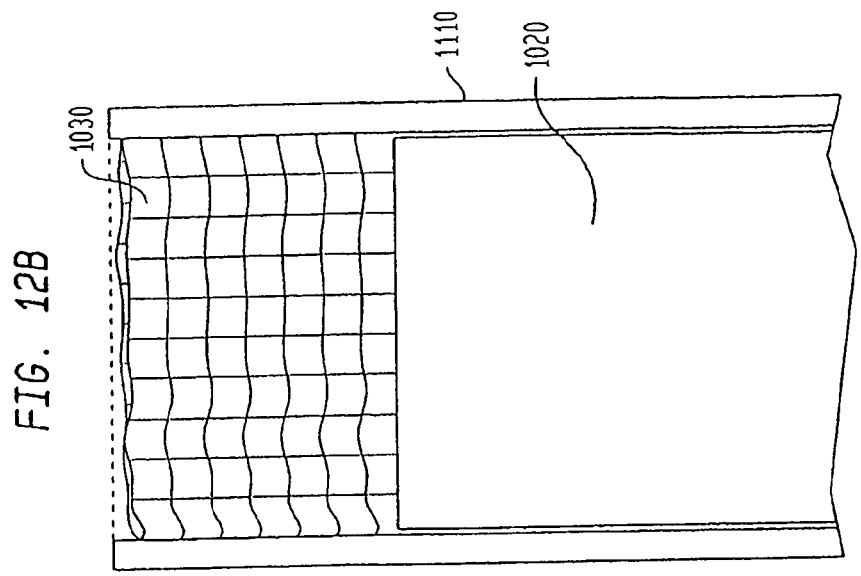
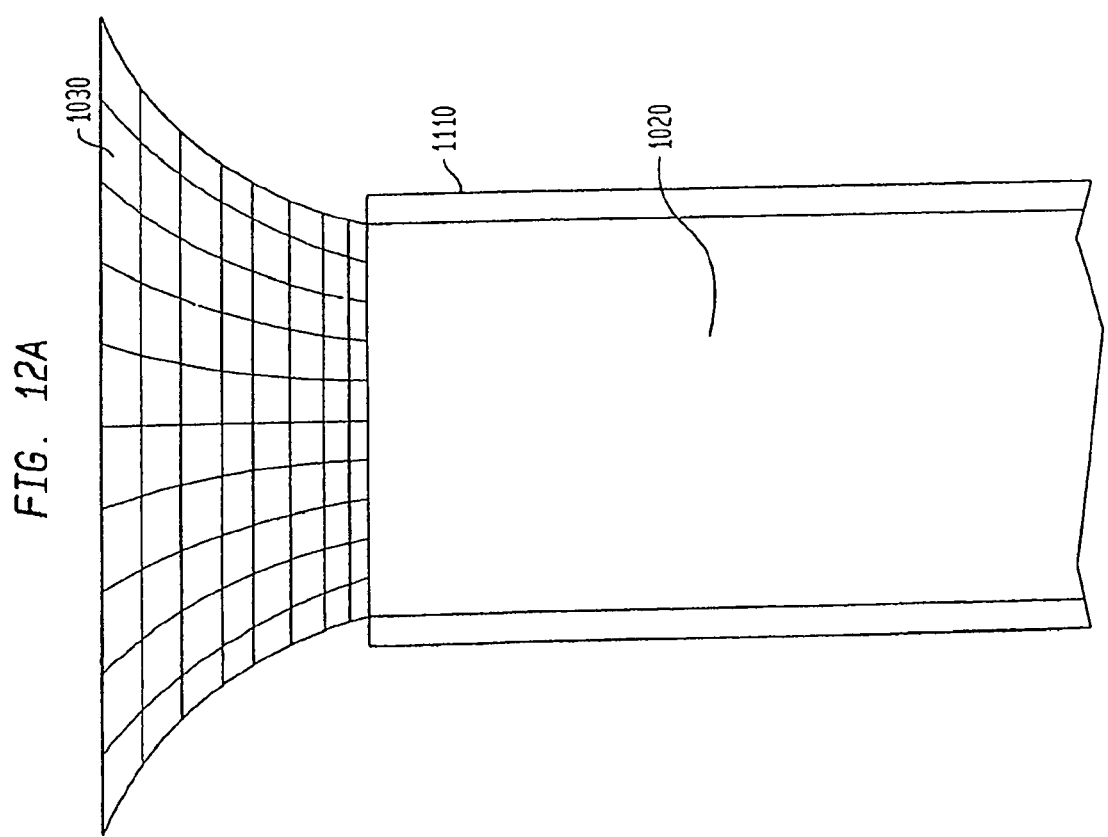

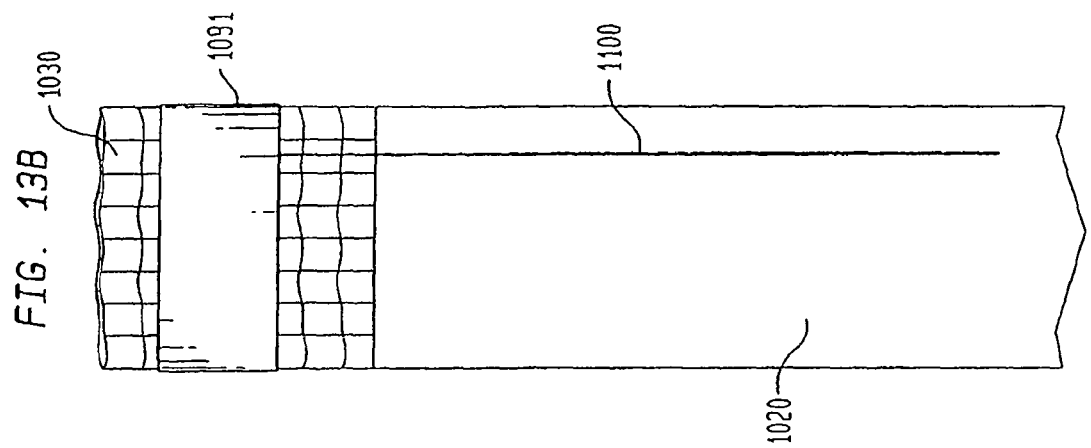
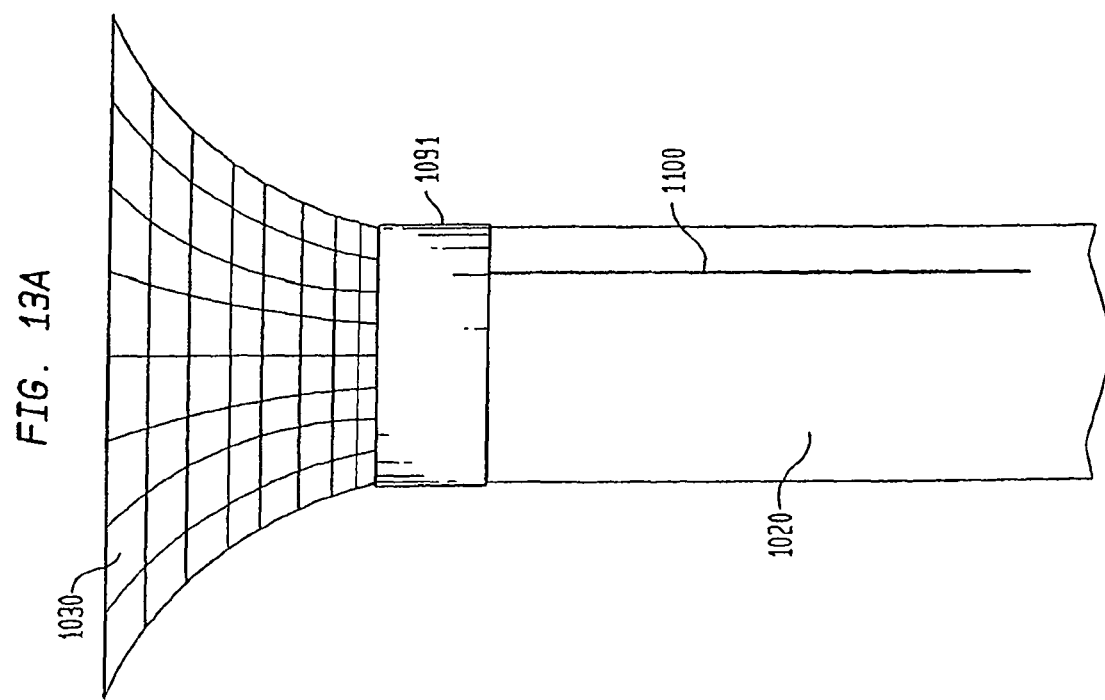

LASSO FILTER TIPPED MICROCATHETER FOR SIMULTANEOUS ROTATING SEPARATOR, IRRIGATOR FOR THROMBECTOMY AND METHOD FOR USE

CROSS-REFERENCE(S)

This application is a continuation of application Ser. No. 16/501,593, filed May 2, 2019, which is a continuation-in-part of application Ser. No. 16/125,691, filed Sep. 8, 2018, now U.S. Pat. No. 10,307,242, which is a continuation in part of application Ser. No. 15/731,478, filed Jun. 16, 2017, now U.S. Pat. No. 10,314,684, which is a continuation in part of application Ser. No. 15/530,898, filed Mar. 20, 2017, now U.S. Pat. No. 10,299,824, which is a continuation in part of application Ser. No. 15/258,877, filed Sep. 7, 2016. The entire contents of each of these applications are is incorporated herein by reference.

FIELD OF THE INVENTION

The present invention provides a medical device for use in vascular procedures. The device employs the simultaneous application of irrigating, aspirating and macerating for the purpose of safely and effectively performing thrombectomy or the like. More particularly, the present invention discloses a "string length adjustment mechanism" for a lasso, namely a mechanism to allow more lengths of string into "system", or alternatively to shorten the length of available string in the system, namely a ratchet, or a reel among others. Said system is part of a filter assembly that is openable and closeable while in use within a bodily vessel, by deployment of a string or wire arranged such that a lasso or drawstring type cincture is effected.

BACKGROUND OF THE INVENTION

Prior Art

Prior art is replete with documentation as the direct and indirect adverse health effects associated with the presence of solid matter within an individual's vascular system. One common example of said matter is a thrombus. A wide variety of techniques are known for removing said mater from a vascular system. Said techniques often use, independently, both electrical and mechanical thrombus maceration devices, irrigation devices or aspiration devices. Typically, said techniques attempt to dislodge said solid matter from the contours of the vascular system, if necessary, and then remove said solid matter from the vascular system by means of suction or the like or retrieval devices.

For purposes of thrombectomy some skilled persons (usually doctors) use one or more tools such as mechanical thrombus maceration devices, irrigation devices, clot retrieval devices and aspiration devices.

The application of irrigation alone into the clot would tend to propagate any loose pieces—whether they are existing loose pieces or lose pieces created by maceration. In Arterial clots in particular the irrigation alone would tend to propagate the loose pieces distally into the smaller arteries and capillary beds. Once they get that far distal, they will clog the capillary beds, cannot be retrieved, and will cause permanent ischemic injury to the tissues. By applying simultaneous proximal aspiration, while occluding the vessel with a wedged occlusive size catheter with or without a catheter with a balloon inflated on the tip, flow at the clot and the artery beyond will be reversed, and loose pieces will flow retrograde into the aspiration catheter and out of the body, rather than traveling downstream and making matters worse. With the flow reversed for safety the irrigation will prevent an empty vacuum where nothing will flow, and will prevent collapse of the artery from the vacuum that also would not allow flow.

In venous clots the same principles apply. Specifically, that the user must to prevent the showering of loose pieces of clot (emboli) to the capillary beds of the at-risk tissue, but the at-risk tissue is different—based on the direction of flow. In venous clots the at-risk tissue is in the heart and lungs—as the venous flow takes the blood back to the right side of the heart and then the lungs. So, in venous cases the key is to pick up the clot pieces before they hit the heart or lungs. Venous cases have a further disadvantage that the vessels with thrombus are typically much larger, so if continuous simultaneous aspiration was applied, the patient would have massive blood loss. On the other hand, venous cases have the advantage, in most cases, that they can be approached easily from either side of the clot—from below and above (further from the heart and closer to the heart). For example (non-limiting)—an iliac clot can be approached with an irrigating macerator, or a plain macerator, from below via the femoral vein. A novel filter aspirator described by the current invention can then be introduced into the internal jugular vein in the neck, advanced over a wire down through the right atrium of the heart and deployed in the inferior vena cava, above the clot—so all showered pieces end up in the filter, and not in the capillary beds of the heart and lungs (small pieces) or in the main pulmonary arteries (larger pieces)—which can cause life threatening hemodynamic instability (a classic large pulmonary embolus). The aspiration on the filter aspirator would only be turned on intermittently, to clear out the clot accumulating at the filter, so as to avoid the massive blood loss that would otherwise occur if the aspiration was on continuously in these cases. In an alternative setup the macerating tool could also be introduced through the filter aspirator. A similar application of this novel filter aspirator could be used to capture and remove emboli during a "declot" procedure for an obstructed dialysis arterio venous graft fistula. In this case the filter aspirator would more often be introduced via the femoral vein, and deployed in the axillary vein or the Subclavian vein. This is in contrast to the arterial example above—where blood flow to that arterial territory is intentionally occluded—so very little blood is aspirated-mostly clot and irrigation. Furthermore, in most arterial applications, even when there is back bleeding from collateral flow, the vessels are typically much smaller so flow rate of blood that can be lost is much lower.

In venous thrombectomy cases the described technique is currently not done because a filter aspirator does not exist. Additionally, If it did exist and aspiration was applied continuously, in many of these cases there could be massive, often life-threatening, blood loss.

In arterial thrombectomy cases irrigation is not used with the aspiration because in smaller arteries there is a technical/engineering challenges of making a device small enough to effectively irrigate through and macerate, while not functionally obstructing the aspiration catheter (if the device fills too much of the aspiration catheter, the effective diameter of the aspiration catheter is reduced tremendously. Flow is inversely proportional to the fourth power of diameter $$R = \frac{8L\eta}{\pi r^4}$$

where r=inside radius of the vessel, L=vessel length, and η=blood viscosity.

It is important to note that a small change in vessel radius will have a very large influence (4th power) on its resistance to flow; e.g., decreasing vessel diameter by 50% will increase its resistance to flow by approximately 16-fold.

More particularly, if one combines the preceding two equations into one expression, which is commonly known as the Poiseuille equation, it can be used to better approximate the factors that influence flow through a cylindrical vessel:

$$Q = \frac{\Delta P \pi r^4}{8L\eta}$$

Aspiration may lead to the collapse of a blood vessel.

Additionally, the art would lead a skilled person away from the present invention's simultaneous combination because the simultaneous use of an irrigation device and aspiration device are counter synergistic (i.e. they would cancel out each other's intended benefit). Consequently, the prior art teaches the use of the serial use of an irrigation device and then an aspiration device.

Accordingly, it would be desirable to provide a means of applying a simultaneous combination of irrigation, aspiration and maceration to a thrombus or similar material.

Blood Vessel Structure and Function

Blood vessels are dynamic structures that constrict, relax, pulsate, and proliferate. Within the body, blood vessels form a closed delivery system that begins and ends at the heart. There are three major types of blood vessels: (i) arteries; (ii) capillaries and (iii) veins. As the heart contracts, it forces blood into the large arteries leaving the ventricles. Blood then moves into smaller arteries successively, until finally reaching the smallest branches, the arterioles, which feed into the capillary beds of organs and tissues. Blood drains from the capillaries into venules, the smallest veins, and then into larger veins that merge and ultimately empty into the heart.

Arteries carry blood away from the heart and "branch" as they form smaller and smaller divisions. In contrast, veins carry blood toward the heart and "merge" into larger and larger vessels approaching the heart. In the systemic circulation, arteries carry oxygenated blood and veins carry oxygen-poor blood. In the pulmonary circulation, the opposite is true. The arteries (still defined as the vessels leading away from the heart), carry oxygen-poor blood to the lungs, and the veins carry oxygen-rich blood from the lungs to the heart.

The only blood vessels that have intimate contact with tissue cells in the human body are capillaries. In this way, capillaries help serve cellular needs. Exchanges between the blood and tissue cells occur primarily through the thin capillary walls.

The walls of most blood vessels (the exception being the smallest vessels, e.g., venules), have three layers, or tunics, that surround a central blood-containing space called the vessel lumen.

The innermost tunic (layer) is the tunica intima. The tunica intima contains the endothelium, the simple squamous epithelium that lines the lumen of all vessels. The endothelium is continuous with the endocardial lining of the heart, and its flat cells fit closely together, forming a slippery surface that minimizes friction so blood moves smoothly through the lumen. In vessels larger than 1 mm in diameter, a sub-endothelial layer, consisting of a basement membrane and loose connective tissue, supports the endothelium.

The middle tunic (layer), the tunica media, is mostly circularly arranged smooth muscle cells and sheets of elastin. The activity of the smooth muscle is regulated by sympathetic vasomotor nerve fibers of the autonomic nervous system. Depending on the body's needs at any given time, regulation causes either vasoconstriction (lumen diameter decreases) or vasodilation (lumen diameter increases). The activities of the tunica media are critical in regulating the circulatory system because small changes in vessel diameter greatly influence blood flow and blood pressure. Generally, the tunica media is the bulkiest layer in arteries, which bear the chief responsibility for maintaining blood pressure and proper circulation.

The outer layer of a blood vessel wall, the tunica externa, is primarily composed of collagen fibers that protect the vessel, reinforce the vessel, and anchor the vessel to surrounding structures. The tunica externa contains nerve fibers, lymphatic vessels, and elastic fibers (e.g., in large veins). In large vessels, the tunica externa contains a structure known as the vasa vasorum, which literally means "vessels of vessels". The vasa vasorum nourishes external tissues of the blood vessel wall. Interior layers of blood vessels receive nutrients directly from blood in the lumen (See, e.g., The Cardiovascular System at a Glance, 4th Edition, Philip I. Aaronson, Jeremy P. T. Ward, Michelle J. Connolly, November 2012, 2012, Wiley-Blackwell, Hoboken, N. J.).

Cerebral Arteries

FIGS. 1 and 2 show schematic illustrations of the brain's blood vessels. Each cerebral hemisphere is supplied by an internal carotid artery, which arises from a common carotid artery beneath the angle of the jaw, enters the cranium through the carotid foramen, traverses the cavernosus sinus (giving off the ophthalmic artery), penetrates the dura and divides into the anterior and middle cerebral arteries. The large surface branches of the anterior cerebral artery supply the cortex and white matter of the inferior frontal lobe, the medial surface of the frontal and parietal lobes and the anterior corpus callosum. Smaller penetrating branches supply the deeper cerebrum and diencephalon, including limbic structures, the head of the caudate, and the anterior limb of the internal capsule. The large surface branches of the middle cerebral artery supply most of the cortex and white matter of the hemisphere's convexity, including the frontal, parietal, temporal and occipital lobes, and the insula. Smaller penetrating branches supply the deep white matter and diencephalic structures such as the posterior limb of the internal capsule, the putamen, the outer globus pallidus, and the body of the caudate. After the internal carotid artery emerges from the cavernous sinus, it also gives off the anterior choroidal artery, which supplies the anterior hippocampus and, at a caudal level, the posterior limb of the internal capsule. Each vertebral artery arises from a subclavian artery, enters the cranium through the foramen magnum, and gives off an anterior spinal artery and a posterior inferior cerebellar artery. The vertebral arteries join at the junction of the pons and the medulla to form the basilar artery, which at the level of the pons gives off the anterior inferior cerebellar artery and the internal auditory artery, and, at the midbrain, the superior cerebellar artery. The basilar artery then divides into the two posterior cerebral arteries. The large surface branches of the posterior cerebral arteries supply the inferior temporal and medial occipital lobes and the posterior corpus callosum; the smaller penetrating branches of these arteries supply diencephalic structures, including the thalamus and the subthalamic nuclei, as well as part of the midbrain (see Principles of Neural Sciences, 2d Ed., Eric R. Kandel and James H. Schwartz, Elsevier Science Publishing Co., Inc., New York, pp. 854-56 (1985)).

Interconnections between blood vessels (anastomoses) protect the brain when part of its vascular supply is compromised. At the circle of Willis, the two anterior cerebral arteries are connected by the anterior communicating artery and the posterior cerebral arteries are connected to the internal carotid arteries by the posterior communicating arteries. Other important anastomoses include connections between the ophthalmic artery and branches of the external carotid artery through the orbit, and connections at the brain surface between branches of the middle, anterior, and posterior cerebral arteries (Principles of Neural Sciences, 2d Ed., Eric R. Kandel and James H. Schwartz, Elsevier Science Publishing Co., Inc., New York, pp. 854-56 (1985)).

Hemorrhage

Blood vessels are typically structurally adept to withstand the dynamic quantities required to maintain circulatory function. For reasons that are not entirely understood, the vessel wall can become fatigued and abnormally weak and possibly rupture. With vessel rupture, hemorrhage (meaning the escape of blood from a ruptured blood vessel) occurs with blood seeping into the surrounding brain tissue. As the blood accumulates within the brain, the displaced volume causes the blood, now thrombosed (clotted), to ultimately compress the surrounding vessels. The compression of vessels translates into a reduced vessel diameter and a corresponding reduction in flow to surrounding tissue, thereby enlarging the insult (See, e.g., Hademenos G. J. and Massoud T. F. Stroke 1997; 28: 2067-2077).

In the brain, hemorrhage may occur at the brain surface (extraparenchymal), for example, from the rupture of congenital aneurysms at the circle of Willis, causing subarachnoid hemorrhage (SAH). Hemorrhage also may be intraparenchymal, for example, from rupture of vessels damaged by long-standing hypertension, and may cause a blood clot (intracerebral hematoma) within the cerebral hemispheres, in the brain stem, or in the cerebellum. Hemorrhage may be accompanied by ischemia or infarction. The mass effect of an intracerebral hematoma may compromise the blood supply of adjacent brain tissue; or SAH may cause reactive vasospasm of cerebral surface vessels, leading to further ischemic brain damage. Infarcted tissue may also become secondarily hemorrhagic. Among the vascular lesions that can lead to hemorrhagic strokes are aneurysms and arteriovenous malformations (AVMs) (See, e.g., Hademenos G. J. and Massoud T. F. Stroke 1997; 28: 2067-2077).

Coagulation

Hemostasis is the cessation of blood loss from a damaged vessel. Platelets first adhere to macromolecules in the subendothelial regions of the injured blood vessel; they then aggregate to form a primary hemostatic plug. Platelets stimulate local activation of plasma coagulation factors, leading to generation of a fibrin clot that reinforces the platelet aggregate. Later, as wound healing occurs, the platelet aggregate and fibrin clot are degraded as wound healing, ensues (Goodman & Gilman's The Pharmacological Basis of Therapeutics, Joel G. Hardman and Lee E. Limbird, Eds, McGraw-Hill, 2001, p. 1519-20).

Coagulation involves a series of zymogen activation reactions. At each stage, a precursor protein, or zymogen, is converted to an active protease by cleavage of one or more peptide bonds in the precursor molecule. The components that can be involved at each stage include a protease from the preceding stage, a zymogen, a non-enzymatic protein cofactor, calcium ions, and an organizing surface that is provided by the damaged blood vessel and platelets in vivo. The final protease to be generated is thrombin (factor IIa).

Fibrinogen is a 330,000 dalton protein that consists of three pairs of polypeptide chains (designated $\alpha$, $\beta$ and $\gamma$) covalently linked by disulfide bonds. Thrombin converts fibrinogen to fibrin monomers (Factor IA) by cleaving fibrinopeptides A (16 amino acid residues) and B (14 amino acid residues) from the amino-terminal ends of the $\alpha$ and $\beta$ chains respectively. Removal of the fibrinopeptides allows the fibrin monomers to form a gel. Initially, the fibrin monomers are bound to each other non-covalently. Subsequently, factor XIIIa catalyzes an interchain transglutamination reaction that cross-links adjacent fibrin monomers to enhance the strength of the clot.

Fibrin participates in both the activation of Factor XIII by thrombin and activation of plasminogen activator (t-PA). It specifically binds the activated coagulation factors factor Xa and thrombin and entraps them in the network of fibers, thus functioning as a temporary inhibitor of these enzymes which stay active and can be released during fibrinolysis. Recent research comprises shown that fibrin plays a key role in the inflammatory response.

The protease zymogens involved in coagulation include factors II (prothrombin), VII, IX, X, XI, XII, and prekallikrein. Factors V and VIII are homologous 350,000 dalton proteins. Factor VIII circulates in plasma bound to von Willebrand factor, while factor V is present both free in plasma and as a component of platelets. Thrombin cleaves V and VIII to yield activated factors (Va and VIIIa) that have at least 50 times the coagulant activity of the precursor forms. Factors Va and VIIIa have no enzymatic activity themselves, but serve as cofactors that increase the proteolytic efficiency of Xa and IXa, respectively. Tissue factor (TF) is a non-enzymatic lipoprotein cofactor that greatly increases the proteolytic efficiency of VIIa. It is present on the surface of cells that are not normally in contact with blood and plasma (e.g. fibroblasts and smooth muscle cells) since they are abluminal to (meaning on the outer surface of a body part with an internal cavity or channel) the endothelium. TF is a key factor that initiates coagulation outside a broken blood vessel.

Two pathways of coagulation are recognized: the intrinsic coagulation pathway, so called because all of the components are intrinsic to plasma, and an extrinsic coagulation pathway. The extrinsic and intrinsic systems converge to activate the final common pathways causing fibrin formation. FIG. 1 shows an illustrative representation of the classic coagulation cascades. It generally is recognized that these systems are somewhat artificial distinctions and do not reflect accurately the coagulation cascades that occur in vivo. Hoffman, M., and Monroe, D. M. III, 'A Cell-based Model of Hemostasis," Thromb. Haemost. 85: 958-65 (2001). Tissue factor exposed by tissue injury, either traumatically, by disease or surgery, can activate sufficient factors X, IX and thrombin (II) to initiate coagulation.

The extrinsic system (tissue factor (TF) pathway) generates a thrombin burst and is initiated when tissue thromboplastin activates Factor VII. Upon vessel injury, TF is exposed to the blood and enzyme coagulation Factor VII (proconvertin) circulating in the blood. Once bound to TF, Factor VII is activated to Factor VIIa by different proteases, including thrombin (Factor IIa), Factor Xa, Factor IXa, Factor XIIa and the Factor VIIa-TF complex itself. The Factor VIIa-TF complex activates Factors IX and X. The activation of Factor Xa by Factor VIIa-TF almost immediately is inhibited by tissue factor pathway inhibitor (TFPI). Factor Xa and its cofactor Va form the prothrombinase complex which activates the conversion of prothrombin to thrombin. Thrombin then activates other components of the coagulation cascade, including Factor V and Factor VIII (which activates Factor XI, which, in turn, activates Factor IX), and activates and releases Factor VIII from being bound to vWF (von Willebrand Factor). Factor VIIa and Factor IXa together they form the "tenase" complex, which activates Factor X, and so the cycle continues.

The intrinsic system (contact activation pathway) is initiated when blood contacts any surface except normal endothelial and blood cells. The intrinsic system begins with formation of the primary complex on collagen by high-molecular weight kininogen (HMWK), prekallikrein, and FXII (Hageman factor). Prekallikrein is converted to kallikrein and Factor XII becomes Factor XIIa. Factor XIIa converts Factor XI into Factor XIa. Factor XIa activates Factor IX, which, with its co-factor Factor VIIIa form the tenase complex, which activates Factor X to Factor Xa.

The prevailing view of hemostasis remains that the protein coagulation factors direct and control the process with cells serving primarily to provide a phosphatidylserine containing surface on which the procoagulant complexes are assembled. In contrast, a model in which coagulation is regulated by properties of cell surfaces, which emphasized the importance of specific cellular receptors for the coagulation proteins, comprises been proposed. Hoffman, M., and Monroe, D. M. III, 'A Cell-based Model of Hemostasis," Thromb. Haemost. 85: 958-65 (2001). Thus, cells with similar phosphatidylserine content can play very different roles in hemostasis depending on their complement of surface receptors. These authors propose that coagulation occurs not as a "cascade", but in three overlapping stages: 1) initiation, which occurs on a tissue factor bearing cell; 2) amplification, in which platelets and cofactors are activated to set the stage for large scale thrombin generation; and 3) propagation, in which large amounts of thrombin are generated on the platelet surface. This cell-based model explains some aspects of hemostasis that a protein-centric model does not.

Modeling Hemostasis

As currently understood, coagulation in vivo is a 3-step process centered on cell surfaces. FIG. 2 shows an illustration of the cell-surface based model of coagulation in vivo (Monroe Arterioscler Thromb Vasc Biol. 2002; 22:1381-1389). In the first step, coagulation begins primarily by initiation with tissue factor (TF), which is present on the subendothelium, tissues not normally exposed to blood, activated monocytes and endothelium when activated by inflammation. Factors VII and VIIa bind to TF and adjacent collagen. The factor VIIa—tissue factor complex activates factor X and IX. Factor Xa activates factor V, forming a prothrombinase complex (factor Xa, Va and calcium) on the TF-expressing cell. In the second step, coagulation is amplified as platelets adhere to the site of injury in the blood vessel. Thrombin is activated by platelet adherence and then acts to fully activate platelets, enhance their adhesion and to release factor V from the platelet as granules. Thrombin on the surface of activated platelets activates factors V, VIII and XI, with subsequent activation of factor IX. The tenase complex (factors IXa, VIIIa and calcium) now is present on platelets where factor Xa can be produced and can generate another prothrombinase complex on the platelet so that there can be large-scale production of thrombin (also called the thrombin burst). Propagation, the third step, is a combination of activation of the prothrombinase complexes that allow large amounts of thrombin to be generated from prothrombin. More platelets can be recruited, as well as activation of fibrin polymers and factor XIII.

Natural Anticoagulant Mechanisms

Platelet activation and coagulation normally do not occur within an intact blood vessel. Thrombosis (meaning a pathological process in which a platelet aggregate and/or a fibrin clot occludes a blood vessel) is prevented by several regulatory mechanisms that require a normal vascular endothelium. Prostacyclin (PGI2), a metabolite of arachidonic acid synthesized by endothelial cells, inhibits platelet aggregation and secretion. Antithrombin is a plasma protein that inhibits coagulation factors of the intrinsic and common pathways. Heparan sulfate proteoglycans synthesized by endothelial cells stimulate the activity of antithrombin. Protein C is a plasma zymogen homologous to Factors II, VII, IX, and X. Activated protein C in combination with its nonenzymatic cofactor (Protein S) degrades cofactors Va and VIIIa and thereby greatly diminishes the rate of activation of prothrombin and factor X. Protein C is activated by thrombin only in the presence of thrombomodulin, an integral membrane protein of endothelial cells. Like antithrombin, protein C appears to exert an anticoagulant effect in the vicinity of intact endothelial cells. Tissue factor pathway inhibitor (TFPI), which is found in the lipoprotein fraction of plasma, when bound to factor Xa, inhibits factor Xa and the factor VIIa-tissue factor complex.

Thrombosis

Thrombosis refers to the formation of a thrombus, meaning a blood clot comprising platelets, fibrin, leukocytes, and red blood cells located within a vascular lumen (Rubin's Pathology, Raphael Rubin and David S. Strayer, ed., 5th Ed., Lippincott Williams & Wilkins: 2008, page 233). A thrombus is distinct from a typical blood clot. While a blood clot results from activation of the coagulation cascade, a thrombus also involves adherence and aggregation of platelets, participation of cellular elements of the immune system, and active participation of endothelial cells of the blood vessel (Id.).

Before injury to a blood vessel, circulating platelets are in a nonadherent state. Injury activates platelet adhesiveness, after which platelets bind to one another to form an aggregate of activated platelets (platelet thrombus) (Id. at 394). These platelet aggregates occlude injured small vessels and prevent leakage of blood. Once platelets are stimulated to adhere to the vessel wall, their granular contents are released, in part by contraction of the platelet cytoskeleton. In turn, these granules promote aggregation of other platelets. Platelet adhesion is enhanced by release of subendothelial von Willebrand factor, which is adhesive for Gp1b platelet membrane protein and for fibrinogen. Activated platelets also release ADP and thromboxane A2, a product of arachidonic acid metabolism, which recruit additional platelets to the process. The platelet membrane protein complex GpIIb-IIIc binds to fibrinogen, thereby forming fibrinogen bridges between platelets, enhancing aggregation, and stabilizing the nascent thrombus. Activated platelets in turn release factors that initiate coagulation, thus forming a complex thrombus on the vessel wall. Thrombin itself stimulates further release of platelet granules and subsequent recruitment of new platelets.

Arterial Thrombosis

The coronary, cerebral, mesenteric, and renal arteries, and arteries of the lower extremities, are the vessels most commonly involved in an arterial thrombosis due to atherosclerosis. Arterial thrombosis may also occur, however, as a result of other disorders, including inflammation of arteries (arteritis), trauma, and blood diseases. Thrombi are also common in aneurysms (localized-dilations of (lie lumen) of the aorta and its major branches, in which the distortion of blood flow, combined with intrinsic vascular disease, promotes thrombosis (Id. at 233).

Risk factors for thrombosis in the arterial system include, without limitation, immobilization after surgery or leg casting, obesity, advanced age, previous thrombosis, and cancer. The three factors that are commonly associated with development of thrombosis are: (1) damage to the endothelium, usually by atherosclerosis, which disturbs the anticoagulant properties of the vessel wall and serves as a site of origin for platelet aggregation and fibrin formation; (2) alteration in blood flow, whether from turbulence at the site of an aneurysm, sites of arterial bifurcation, or slowing of blood flow in narrowed arteries; and (3) increased coagulability of the blood.

Since most arterial thrombi occlude the vessel in which they occur, they often lead to ischemic necrosis of tissue supplied by that artery, i.e., an infarct. Infarction is the process by which coagulative necrosis develops in an area distal to the occlusion of an end-artery (Id. at 239). Thrombosis of a coronary or cerebral artery results in myocardial infarct (heart attack) or cerebral infarct (stroke), respectively (Id. at 234).

Myocardial infarcts can be transmural (through the entire wall) or subendocardial. While a transmural infarct results from complete occlusion of a major extramural coronary artery, a subendocardial infarction reflects prolonged ischemia caused by partially occluding lesions of the coronary arteries when the requirement for oxygen exceeds the supply (Id. at 241).

Thrombosis in the Heart

In a similar manner to the arterial system, thrombosis in the heart can develop on the endocardium. Endocardial injury and changes in blood flow in the heart may lead to a thrombus adhering to the underlying wall of the heart (mural thrombosis) (Id. at 234). Mural thrombosis may occur as a result of diseases such as myocardial infarction, atrial fibrillation, cardiomyopathy, and endocarditis. In myocardial infarction, adherent mural thrombi form in the left ventricular cavity over areas of myocardial infarction due to damaged endocardium and alterations in blood flow associated with a poorly functional or a dynamic segment of the myocardium. In atrial fibrillation, disordered atrial rhythm leads to slower blood flow and impaired left atrial contractility, which predisposes to formation of mural thrombi in atria. In cardiomyopathy, primary myocardial diseases are associated with mural thrombi in the left ventricle, due to, e.g., endocardial injury and altered hemodynamics associated with poor myocardial contractility. In endocarditis, small thrombi may also develop on cardiac valves, usually mitral or aortic, that are damaged by a bacterial infection. Occasionally these small thrombi form in the absence of valve infections on a mitral or tricuspid valve (for example, injured by systemic lupus erythrematosis, SLE). In chronic wasting states, large friable small thrombi may appear on cardiac valves, possibly reflecting a hypercoagulable state. A major complication of thrombosis in the heart occurs when fragments of the thrombus detach and become lodged in blood vessels at distant sites (embolization) (Id at 234).

Venous Thrombosis

Deep venous thrombosis, which occurs when a thrombus becomes lodged in one of the deep venous systems of the leg, often results from one or more of the same causative factors that favor arterial and cardiac thrombosis. Those factors are endothelial injury (e.g., trauma, surgery, childbirth), stasis (e.g., heart failure, chronic venous insufficiency, post-operative immobilization, prolonged bed rest) and a hypercoagulable state (e.g., oral contraceptives, late pregnancy, cancer, inherited thrombophilic disorders, advanced age, venous varicosities, phlebosclerosis) (Id. at 234-235).

Greater than 90% of venous thrombosis occur in deep veins of the legs, and have several potential fates. They may remain small and eventually become lysed, posing no further threat to health. Many become organized, whereby a small organization of venous thrombi may be incorporated into the vessel wall, and larger ones may undergo canalization, with partial restoration of venous drainage. Venous thrombi may also result in propagation, whereby they serve as a site of origination for further thrombosis and propagate proximally to involve the larger iliofemoral veins. Those venous thrombi that are large or those that have propagated proximally are a significant hazard to life, since they may dislodge and be carried to the lungs as pulmonary emboli (Id).

Thrombosis in the Brain

Thrombosis of a cerebral artery results in cerebral infarct, also referred to as a stroke. the most common type of cerebral infarct is the ischemic stroke, which may occur as a result of the blockage of an artery vein (Gomes et al., Handbook of Clinical Nutrition and Stroke (2013) Chapter 2, page 17). The term "stroke in evolution" as used herein reflects propagation of a thrombus in the carotid or basilar arteries, and describes the progression of neurologic symptoms while the patient is under observation. The term "completed stroke" as used herein refers to a stable neurologic deficit resulting from a cerebral infarct (Rubin's Pathology, Raphael Rubin and David S. Strayer, ed., 5th Ed., Lippincott Williams & Wilkins: 2008, page 1192).

The occlusion of different cerebral vessels results in diverse neurologic deficits caused by stroke. For example, occlusion or stenosis of an internal carotid artery affects the ipsilateral hemisphere, but this can be offset by the variable collateral circulation through the anterior and posterior communicating arteries. Most often, occlusion of a carotid artery produces infarcts restricted to all or some portion of the distribution of the middle cerebral artery. The consequences of occlusion of the various branches of the circle of Willis depend on the configuration of the circle. For example, occlusion at the trifurcation of the middle cerebral artery deprives the parietal cortex of circulation and produces motor and sensory deficits. When the dominant hemisphere is involved, these lesions are commonly accompanied by apcomprisesia. An infarct of the lengthy and slender striate arteries, which originate from the proximal middle cerebral artery, often transects the internal capsule and produces hemiparesis or hemiplegia (Id.).

Infarction of the cerebral arteries may result from local ischemia or a generalized reduction in blood flow. The latter often results from systemic hypotension (e.g., shock), and produces infarction in the border zones between the distributions of the major cerebral arteries. If prolonged, severe hypotension can cause widespread brain necrosis. The occlusion of a single vessel in the brain (e.g., after an embolus comprises lodged) causes ischemia and necrosis in a well-defined area. The occlusion of a large artery produces a wide area of necrosis.

Cerebral Venous Sinus Thrombosis

The cerebral veins empty into large venous sinuses, the most prominent of which is the sagittal sinus which accommodates the venous drainage from the superior portions of the cerebral hemispheres. If a patient develops a blood clot in a superficial or deep cerebral vein or venous sinus, hydrostatic pressure will increase upstream of the venous side of the capillary bed until ultimately water is forced through the capillary walls and into the interstitium of adjacent brain tissue reliant on the affected vein for normal fluid balance. This will eventually lead to hemorrhagic necrosis and vasogenic edema in the affected area. Venous sinus thrombosis in the brain is a potentially lethal complication of systemic dehydration, phlebitis, obstruction by a neoplasm, or sickle cell disease. Because venous obstruction causes stagnation upstream, abrupt thrombosis of the sagittal sinus results in bilateral hemorrhagic infarctions of the frontal lobe regions. A more indolent occlusion of the sinus (e.g., due to invasion by a meningioma) permits the recruitment of collateral circulation through the inferior sagittal sinus (Id. at 1194).

Fibrinolytic Agents

One method of treating a thrombosis is with a thrombolytic agent that breaks down the fibrinogen and fibrin comprising the thrombus. These fibrinolytic agents (also referred to as plasminogen activators) can be broadly classified into two groups: fibrin-specific agents; and non-fibrin specific agents. Fibrin-specific agents include drugs such as alteplase (tPA), reteplase (recombinant plasminogen activator; r-PA), and tenecteplase, which produce limited plasminogen conversion in the absence of fibrin (Ouriel K. A history of thrombolytic therapy. J Endovasc Ther. 2004 Dec. 11 Suppl 2:11128-133). Non-fibrin specific agents, including agents such as streptokinase, catalyze systemic fibrinolysis.

Fibrinolytic agents can be administered systemically or directly to the area of the thrombus. Treatment of acute myocardial infarction and acute ischemic stroke typically involves systemic delivery of the fibrinolytic agents (Hoffman R, Benz E J, Shattil S J, et al. Antithrombotic Drugs. In: Hematology: Basic Principles and Practice. 5th ed. Philadelphia, Pa.: Churchill Livingston Elsevier; 2008. chap 137).

Fibrinolytic agents can be used to treat several types of vascular obstruction conditions such as acute myocardial infarction, pulmonary embolism, deep vein thrombosis, acute ischemic stroke, and peripheral arterial disease. However, the use of fibrinolytic therapy comprises many drawbacks, including, without limitation, allergic reactions, embolism, stroke, and reperfusion arrhythmias, among others. One of the more serious complications is hemorrhage, such as intracranial hemorrhage (ICH) (See, Mehta R H, Cox M, Smith E E, et al., Race/Ethnic differences in the risk of hemorrhagic complications among patients with ischemic stroke receiving thrombolytic therapy. Stroke. 2014 August 45 (8):2263-9).

In addition, fibrinolytic agents have limited efficacy in certain conditions. For example, although tPA is an accepted treatment for treatment of acute ischemic stroke, the drug's ability to recanalize a vessel is poor in some cases. In proximal occlusions, for example, low recanalization rates are observed (8% recanalization in ICA occlusions), while in more distal occlusions higher rates of recanalization are observed (26% in M1 occlusions, 35% in M2 occlusions, and 40% in M3 occlusions) (Holodinsky, J. K. et al., Curr Neurol Neurosci Rep (2016) 16:42). Studies have shown that tPA is relatively ineffective for occlusions in the proximal anterior circulation, such as carotid T occlusions, carotid L occlusions, and M1/M2 occlusions of the MCA, which account for about one third of cases of acute ischemic stroke (Id.). Furthermore, the effectiveness of fibrinolytic agents, such as tPA, is dependent upon early administration. For example, a meta-analysis of several randomized trials of tPA administration after stroke onset revealed that a treatment delay of more than 4.5 hours resulted in no difference between tPA treatment and placebo treatment. This result may be due, in part, to a reduced chance of thrombus resolution as time passes and fibrin crosslinking occurs within the thrombus (Id.).

In some instances, fibrinolytic agents cannot be used at all. For example, the presence of active internal bleeding, recent intracranial or intraspinal trauma, a past or present bleeding disorder, uncontrolled hypertension, and pregnancy are all absolute contraindications of fibrinolytic agents.

Mechanical Endovascular Intervention

The current standard for therapeutic recanalization and reperfusion in vascular disease and acute stroke is to perform mechanical endovascular interventions via a transfemoral approach, meaning, starting a catheter in the femoral artery at the groin, proceeding through the aorta and carotid artery to the affected blood vessel. All existing devices are designed to be used from this starting point and surgeons are most familiar and comfortable with this route.

Mechanical Endovascular Intervention in Coronary Artery Disease (CAD)

Percutaneous Coronary Intervention (PCI)

Percutaneous coronary intervention (PCI) is a nonsurgical method for coronary artery revascularization. PCI methods include balloon angioplasty, coronary stenting, atherectomy (devices that ablate plaque), thrombectomy (devices that remove clots from blood vessels) and embolic protection (devices that capture and remove embolic debris).

Balloon Angioplasty

Balloon angioplasty involves advancing a balloon-tipped catheter to an area of coronary narrowing, inflating the balloon, and then removing the catheter after deflation. Balloon angioplasty can reduce the severity of coronary stenosis, improve coronary flow, and diminish or eliminate objective and subjective manifestations of ischemia (Losordo D. W. et al. Circulation 1992 December 86(6): 1845-58). The mechanism of balloon angioplasty action involves three events: plaque fracture, compression of the plaque, and stretching of the vessel wall. These lead to expansion of the external elastic lumina and axial plaque redistribution along the length of the vessel (Losordo D. W. et al. Circulation 1992 December 86(6):1845-58).

Coronary Stenting

Coronary stents are metallic scaffolds that are deployed within a diseased coronary artery segment to maintain wide luminal patency. They were devised as permanent endoluminal prostheses that could seal dissections, create a predictably large initial lumen, and prevent early recoil and late vascular remodeling (Krajcer Z. and Howell M. H. Tex Heart Inst J. 2000; 27(4): 369-385).

Drug-eluting stents (DESs) elute medication to reduce restenosis (the recurrence of abnormal narrowing of a blood vessel) within the stents. Local release of rapamycin and its derivatives or of paclitaxel from a polymer matrix on the stent during the 30 days after implantation comprises been shown to reduce inflammation and smooth muscle cell proliferation within the stent, decreasing in-stent late loss of luminal diameter from the usual 1 mm to as little as 0.2 mm (Stone G. W. et al. N Engl J Med. 2007 Mar. 8. 356(10): 998-1008). This dramatically lowers the restenosis rate after initial stent implantation or after secondary implantation of a DES for an in-stent restenosis (Stone G. W. et al. N Engl J Med. 2007 Mar. 8. 356(10):998-1008).

Coronary stents are used in about 90% of interventional procedures. Stent-assisted coronary intervention comprises replaced coronary artery bypass graft (CABG) as the most common revascularization procedure in patients with coronary artery disease (CAD) and is used in patients with multi-vessel disease and complex coronary anatomy (Kalyanasundaram A. et al. Medscape Dec. 16, 2014; article 164682; emedicine.medscape.com/article/164682-overview#a3).

Atherectomy

The directional coronary atherectomy (DCA) catheter was first used in human peripheral vessels in 1985 and in coronary arteries in 1986. In this procedure, a low-pressure positioning balloon presses a windowed steel housing against a lesion; any plaque that protrudes into the window is shaved from the lesion by a spinning cup-shaped cutter and trapped in the device's nose cone (Hinohara T. et al. Circulation 1990 March 81(3 Suppl): IV79-91).

Rotational atherectomy uses a high-speed mechanical rotational stainless-steel burr with a diamond chip-embedded surface. The burr is attached to a hollow flexible drive shaft that permits it to be advanced over a steerable guide wire with a platinum coil tip. The drive shaft is encased within a Teflon® sheath through which a flush solution is pumped to lubricate and cool the drive shaft and burr. A compressed air turbine rotates the drive shaft at 140,000-200,000 rpm during advancement across a lesion (Hinohara T. et al. Circulation 1990 March 81(3 Suppl): IV79-91).

Laser Ablation

In laser ablation, an intense light beam travels via optical fibers within a catheter and enters the coronary lumen. After the target lesion is crossed with the guide wire, the laser catheter is advanced to the proximal end of the lesion. Blood and contrast medium are removed from the target vessel by flushing with saline before activating the laser (Kalyanasundaram A. et al. Medscape Dec. 16, 2014; article 164682; emedicine.medscape.com/article/164682-overview#a3).

Mechanical Thrombectomy

Intracoronary thrombi may be treated with mechanical thrombectomy devices. These include rheolytic, suction and ultrasonic thrombectomy devices.

In rheolytic thrombectomy, high-speed water jets create suction via the Bernoulli-Venturi effect. The jets exit orifices near the catheter tip and spray back into the mouth of the catheter, creating a low-pressure region and intense suction. This suction pulls surrounding blood, thrombus, and saline into the tip opening and propels particles proximally through the catheter lumen and out of the body (Kalyanasundaram A. et al. Medscape Dec. 16, 2014; article 164682; emedicine.medscape.com/article/164682-overview#a3).

The catheters used for suction thrombectomy act via manual aspiration. These catheters are advanced over a wire to the intracoronary thrombus then passed through the thrombus while suction is applied to a hole in the catheter tip. Large intact thrombus fragments can be removed by means of this technique (Kalyanasundaram A. et al. Medscape Dec. 16, 2014; article 164682; emedicine.medscape.com/article/164682-overview#a3).

Ultrasonic thrombectomy involves the use of ultrasonic vibration to induce cavitation that can fragment a thrombus into smaller components (Choi S. W. et al. J. Intery Cardiol. 2006 Feb. 19(1): 87-92).

Embolization Protection

Embolization (the passage of an embolus (blood clot) within the blood stream) can be caused by the manipulation of guidewires, balloons, and stents across complex atherosclerotic carotid artery lesions (Krajcer Z. and Howell M. H. Tex Heart Inst J. 2000; 27(4): 369-385). Several devices have been developed to trap such embolic material and remove it from the circulation.

The PercuSurge Guardwire is a device that consists of a 0.014- or 0.018-inch angioplasty guidewire constructed of a hollow nitinol hypotube. Incorporated into the distal wire segment is an inflatable balloon capable of occluding vessel flow. The proximal end of the wire incorporates a Microseal™ that allows inflation and deflation of the distal occlusion balloon. When the Microseal adapter is detached, the occlusion balloon remains inflated, at which time angioplasty and stenting are performed. An aspiration catheter can be advanced over the wire into the vessel, and manual suction is applied to retrieve particulate debris (Krajcer Z. and Howell M. H. Tex Heart Inst J. 2000; 27(4): 369-385).

The Medicorp device consists of a protection balloon and a dilation balloon that can be used over a 0.014-inch coronary guidewire. Occlusion above the lesion and below the lesion creates a dilation zone without a flow, which is aspirated and cleared of atherosclerotic debris (Krajcer Z. and Howell M. H. Tex Heart Inst J. 2000; 27(4): 369-385).

Endovascular Treatment of Abdominal Aortic Aneurysms (AAA)

Two endoluminal AAA exclusion stent graft systems have received FDA approval: (i) the Ancure™ Endograft System (Guidant/EVT; Menlo Park, Calif.); and (ii) the AneuRx™ device (Medtronic AVE; Santa Rosa, Calif.) (Krajcer Z. and Howell M. H. Tex Heart Inst J. 2000; 27(4): 369-385). Both are over-the-wire systems that require bilateral femoral artery access.

The Ancure™ stent graft is an unsupported, single piece of woven Dacron® fabric. The graft is bifurcated and comprises no intra-graft junctions. The main device is delivered through a 24-Fr introducer sheath; a 12-Fr sheath is required to facilitate the deployment of the contralateral iliac limb. The graft is attached via a series of hooks that are located at the proximal aortic end and at both iliac ends. The hooks are seated transmurally (passing through the vessel wall) in the aorta and the iliac arteries, initially by minimal radial force, and then affixed by low-pressure balloon dilation. Radiopaque markers are located on the body of the graft for correct alignment and positioning (Krajcer Z. and Howell M. H. Tex Heart Inst J. 2000; 27(4): 369-385).

The AneuRx™ device is a modular 2-piece system composed of a main bifurcation segment and a contralateral iliac limb. The graft is made of thin-walled woven polyester that is fully supported by a self-expanding nitinol exoskeleton. Attachment is accomplished by radial force at the attachment sites, which causes a frictional seal. The main bifurcated body is delivered through a 21-Fr sheath, and the contralateral limb requires a 16-Fr sheath. The body of the graft comprises radiopaque markers that facilitate correct alignment and positioning (Krajcer Z. and Howell M. H. Tex Heart Inst J. 2000; 27(4): 369-385).

Mechanical Endovascular Neurointervention

Mechanical Thrombectomy

Mechanical thrombectomy (excision of a clot from a blood vessel) devices remove occluding thrombi (blood clots) from the target vessel by a catheter. Subgroups include: (1) suction thrombectomy devices that remove occlusions from the cerebral vessels by aspiration (Proximal Thrombectomy) and (2) clot removal devices that physically seize cerebral thrombi and drag them out of the cerebral vessels (Distal Thrombectomy) (Gralla J. et al. Stroke 2006; 37: 3019-24; Brekenfeld C. et al. Stroke 2008; 39: 1213-9).

Proximal Endovascular Thrombectomy

Manual suction thrombectomy is performed by moving forward an aspiration catheter at the proximal surface of the thrombus (Singh P. et al. J Neurosci Rural Pract. 2013 July-September; 4(3): 298-303). Manual aspiration is then carried out and the aspiration catheter is taken back under continuous negative pressure. The Penumbra System™ (Penumbra, Almeda, Calif. USA), a variation of the manual proximal aspiration method, comprises a dedicated reperfusion catheter attached to a pumping system applying constant aspiration. A second retriever device is similar to a stent and is utilized to take out the resistant clot (Singh P. et al. J Neurosci Rural Pract. 2013 July-September; 4(3): 298-303). The time window for neuroradiological intervention is 8 hours after stroke onset in patients not eligible for intravenous thrombolysis or in patients where intravenous thrombolysis was unsuccessful (Singh P. et al. J Neurosci Rural Pract. 2013 July-September; 4(3): 298-303).

The Penumbra System™ comprises been examined in a number of clinical trials. The Penumbra Pivotal Stroke Trial was a prospective, single-arm, multicenter study that recruited 125 stroke patients (mean NIHSS 18) within 8 hours of symptom onset and was successful in 81.6% of treated vessels (Penumbra Pivotal Stroke Trial Investigators: The Penumbra pivotal stroke trial: Safety and effectiveness of a new generation of mechanical devices for clot removal in intracranial large vessel occlusive disease. Stroke 2009; 40: 2761-8). However, a good clinical outcome at 90 days was attained in only 25% of patients and in 29% of patients with successful recanalization (the process of restoring flow to or reuniting an interrupted channel such as a blood vessel) of the target vessel (Penumbra Pivotal Stroke Trial Investigators: The penumbra pivotal stroke trial: Safety and effectiveness of a new generation of mechanical devices for clot removal in intracranial large vessel occlusive disease. Stroke. 2009; 40: 2761-8). Poor clinical results occurred despite comparatively better recanalization rates as evidenced by a mortality rate of 32.8% and the occurrence of symptomatic intracerebral hemorrhage (ICH) in 11.2% (Penumbra Pivotal Stroke Trial Investigators: The penumbra pivotal stroke trial: Safety and effectiveness of a new generation of mechanical devices for clot removal in intracranial large vessel occlusive disease. Stroke. 2009; 40: 2761-8).

Distal Endovascular Thrombectomy

Distal thrombectomy is a technically difficult procedure (Singh P. et al. J Neurosci Rural Pract. 2013 July-September; 4(3): 298-303). A number of clinical studies have been carried out using the MERCI (Mechanical Embolus Removal in Cerebral Ischemia) Retriever® device (Concentric Medical, Mountain View, USA), which was the earliest distal thrombectomy device approved by the United States Food and Drug Administration (FDA) (Singh P. et al. J Neurosci Rural Pract. 2013 July-September; 4(3): 298-303). In the initial stage of the procedure, the occlusion site must be traversed with a microcatheter so as to deploy the device beyond the thrombus. The MERCI Retriever® device is pulled back into the thrombus and positioned within the clot. Next, the MERCI Retriever® and the trapped clot are withdrawn, initially into the positioning catheter and then out of the patient's body (Singh P. et al. J Neurosci Rural Pract. 2013 July-September; 4(3): 298-303). Proximal balloon occlusion by means of a balloon guide catheter and aspiration during retrieval of the Merci device is done for the majority of cases in order to prevent thromboembolic complications (Nogueira R. G. et al. Am J Neuroradiol. 2009; 30: 649-61; Nogueira R. G. et al. Am J Neuroradiol. 2009; 30: 859-7). During in vivo experimental studies, the distal technique was shown to be more efficient than proximal manual aspiration (Gralla J. et al. Stroke 2006; 37: 3019-24).

The MERCI Retriever® clinical trial was a 25-site, uncontrolled, technical efficacy trial (Smith W. S. et al. Stroke 2005; 36: 1432-8). The trial incorporated 151 patients with occlusion of the internal carotid artery or vertebral and basilar arteries, who did not qualify for intra-arterial therapy (IAT) within 8 hours of symptom onset (Smith W. S. et al. Stroke 2005; 36: 1432-8). Successful recanalization was accomplished in 46%, with excellent clinical outcome in 27.7% of patients (Smith W. S. et al. Stroke 2005; 36: 1432-8). Successful recanalization was linked with distinctly better clinical outcomes. Average procedure time was 2.1 hours, with clinically noteworthy procedural complications occurring in 7.1% and a rate of symptomatic intracranial hemorrhage (ICH) occurring in 7.8% of patients (Smith W. S. et al. Stroke 2005; 36: 1432-8). Despite good clinical outcome, limitations of this device include operator learning curve, the need to traverse the occluded artery to deploy the device distal to the occlusion, the duration required to perform multiple passes with the device, clot fragmentation and passage of an embolus within the bloodstream (Meyers P. M. et al. Circulation 2011; 123: 2591-2601).

Self-Expanding Stents

Until recently, intracranial stenting was restricted to off-label use of balloon-mounted stents intended for cardiac circulation (Singh P. et al. J Neurosci Rural Pract. 2013 July-September; 4(3): 298-303). These stents are not ideal for treating intracranial disease due to their rigidity which makes navigation in the convoluted intracranial vessels difficult (Singh P. et al. J Neurosci Rural Pract. 2013 July-September; 4(3): 298-303). Self-expanding intracranial stents permit stenting in acute stroke that is unmanageable with conventional treatment regimens. The clot occluding the vessel is outwardly displaced by the side of the vessel wall and becomes trapped in the interstices of a self-expanding stent (SES). Wingspan™ (Stryker), Neuroform® (Stryker, Kalamazoo, Mich.), and Cordis Enterprise™ (Cordis Neurovascular, Fremont, Calif.) self-expanding stenting systems have improved steering, cause a reduced amount of vasospasm, and cause a reduced amount of side-branch occlusions as compared to balloon-inflated stents (Singh P. et al. J Neurosci Rural Pract. 2013 July-September; 4(3): 298-303). Drawbacks of this method include delayed in-stent thrombosis, the use of platelet inhibitors which may cause intracerebral hemorrhage (ICH) and perforator occlusion from relocation of the thrombus after stent placement (Samaniego E. A. et al Front Neurol. 2011; 2: 1-7; Fitzsimmons B. F. et al. Am J Neuroradiol. 2006; 27: 1132-4; Levy E. I. et al. Neurosurgery 2006; 58: 458-63; Zaidat O. O. et al. Stroke 2008; 39: 2392-5).

Retrievable Thrombectomy Stents

Retrievable thrombectomy stents are self-expandable, re-sheathable, and re-constrainable stent-like thrombectomy devices which combine the advantages of intracranial stent deployment with immediate reperfusion and subsequent retrieval with definitive clot removal from the occluded artery (Singh P. et al. J Neurosci Rural Pract. 2013 July- September; 4(3): 298-303). Removal of the device circumvents the drawbacks associated with permanent stent implantation. These include the requirement for double anti-platelet medication, which potentially adds to the risk of hemorrhagic complications, and the risk of in-stent thrombosis or stenosis. The application of retrievable thrombectomy stents is analogous to that of intracranial stents. Under general anesthesia, using a transfemoral approach, a guide catheter is positioned in the proximal internal carotid artery. A guide wire is advanced coaxially over a microcatheter within the blocked intracranial vessel and navigated past the thrombus. The microcatheter is then advanced over the wire through the clot, and the guide wire is substituted for the embolectomy device (Id.). The revascularization device is placed with the middle third of the device residing within the thrombus formation. The radial force of the stent retriever is able to create a channel by squeezing the thrombus and is able to partially restore blood flow to the distal territory in the majority of cases, producing a channel for a temporary bypass (Id). The device is usually left in place for an embedding time of up to 10 minutes, permitting entrapment of the thrombus within the stent struts. To extract the thrombus, the unfolded stent and the microcatheter are slowly dragged into the guide catheter with flow reversal by continuous aspiration with a 50-ml syringe from the guide catheter (Id.). The designs of these stents differ in terms of radial strength, design of the proximal and distal stent aperture, stent cell design, material and supplementary intraluminal struts (Mordasini P. et al. Am J Neuroradiol 2011; 32: 294-300; Brekenfeld C. et al. Am J Neuroradiol. 201; 2: 1269-73; Mordasini P. et al. Am J Neuroradiol. 2013; 34: 153-8).

Blood Vessels Used for Mechanical Intervention Femoral Artery

The femoral artery is the main artery that provides oxygenated blood to the tissues of the leg. It passes through the deep tissues of the femoral (or thigh) region of the leg parallel to the femur.

The common femoral artery is the largest artery found in the femoral (thigh) region of the body. It begins as a continuation of the external iliac artery at the inguinal ligament which serves as the dividing line between the pelvis and the leg. From the inguinal ligament, the femoral artery follows the medial side of the head and neck of the femur inferiorly and laterally before splitting into the deep femoral artery and the superficial femoral artery.

The superficial femoral artery flexes to follow the femur inferiorly and medially. At its distal end, it flexes again and descends posterior to the femur before forming the popliteal artery of the posterior knee and continuing on into the lower leg and foot. Several smaller arteries branch off from the superficial femoral artery to provide blood to the skin and superficial muscles of the thigh.

The deep femoral artery follows the same path as the superficial branch, but follows a deeper path through the tissues of the thigh, closer to the femur. It branches off into the lateral and medial circumflex arteries and the perforating arteries that wrap around the femur and deliver blood to the femur and deep muscles of the thigh. Unlike the superficial femoral artery, none of the branches of the deep femoral artery continue into the lower leg or foot.

Like most blood vessels, the femoral artery is made of several distinct tissue layers that help it to deliver blood to the tissues of the leg. The innermost layer, known as the endothelium or tunica intima, is made of thin, simple squamous epithelium that holds the blood inside the hollow lumen of the blood vessel and prevents platelets from sticking to the surface and forming blood clots. Surrounding the tunica intima is a thicker middle layer of connective tissues known as the tunica media. The tunica media contains many elastic and collagen fibers that give the femoral artery its strength and elasticity to withstand the force of blood pressure inside the vessel. Visceral muscle in the tunica media may contract or relax to help regulate the amount of blood flow. Finally, the tunica externa is the outermost layer of the femoral artery that contains many collagen fibers to reinforce the artery and anchor it to the surrounding tissues so that it remains stationary.

The femoral artery is classified as an elastic artery, meaning that it contains many elastic fibers that allow it to stretch in response to blood pressure. Every contraction of the heart causes a sudden increase in the blood pressure in the femoral artery, and the artery wall expands to accommodate the blood. This property allows the femoral artery to be used to detect a person's pulse through the skin (See, e.g., The Cardiovascular System at a Glance, 4th Edition, Philip I. Aaronson, Jeremy P. T. Ward, Michelle J. Connolly, November 2012, © 2012, Wiley-Blackwell, Hoboken, N. J.).

Use of the Femoral Artery for Endovascular Procedures

Endovascular diagnostic and therapeutic procedures are generally performed through the femoral artery. Some of the reasons for this generalized approach include its location, easy approach for puncture and hemostasis, low rate of complications, technical ease, wide applicability and relative patient comfort (Alvarez-Tostado J. A. et al. Journal of Vascular Surgery 2009; 49(2): 378-385). Femoral puncture also allows access to virtually all of the arterial territories and affords favorable ergonomics for the operator in most instances (Alvarez-Tostado J. A. et al. Journal of Vascular Surgery 2009; 49(2): 378-385).

Brachial Artery

The brachial artery is a major blood vessel located in the upper arm and is the main supplier of blood to the arm and hand. It continues from the axillary artery at the shoulder and travels down the underside of the arm. Along with the medial cubital vein and bicep tendon, it forms the cubital fossa, a triangular pit on the inside of the elbow. Below the cubital fossa, the brachial artery divides into two arteries running down the forearm: the ulnar and the radial; the two main branches of the brachial artery. Other branches of the brachial artery include the inferior ulnar collateral, profunda brachii, and superior ulnar arteries (See, e.g., The Cardiovascular System at a Glance, 4th Edition, Philip I. Aaronson, Jeremy P. T. Ward, Michelle J. Connolly, November 2012, © 2012, Wiley-Blackwell, Hoboken, N. J.).

Use of the Brachial Artery for Endovascular Procedures

Brachial artery access is a critical component of complex endovascular procedures, especially in instances where femoral access is difficult or contraindicated, such as the absence of palpable femoral pulses, severe common femoral occlusive disease, recent femoral intervention or surgery or femoral aneurysms/pseudoaneurysms. It is a straightforward procedure with a high success rate for percutaneous cannulation (Alvarez-Tostado J. A. et al. Journal of Vascular Surgery 2009; 49(2): 378-385). However, there is a general reluctance to puncture the right brachial artery due to the need to navigate through the innominate artery and arch and due to the risk for complications such as direct nerve trauma and ischemic occlusion resulting in long-term disability (Alvarez-Tostado J. A. et al. Journal of Vascular Surgery 2009; 49(2): 378-385; Cousins T. R. and O'Donnell J. M. AANA Journal 2004; 72(4): 267-271).

Need for New Endovascular Thrombectomy Devices

Mechanical endovascular neurointerventions are the current standard for the treatment of acute stroke. Several independent clinical trials have, however, identified significantly different clinical outcomes in patients when treated with different endovascular techniques and thrombectomy devices (Papanagiotou, P., and White, C. J., Endovascular Reperfusion Strategies for Acute Stroke, JACC: Cardiovascular Interventions, 2016, Vol. 9, No. 4, pg 307). For example, stent retriever devices generally have been identified as providing higher recanalization rates with a reduced recanalization time and lower complication rates when compared to first generation mechanical recanalization devices such as the Merci device and the Penumbra aspiration system (Id. at 315).

Despite the potential to diminish procedure time and to improve recanalization rates, drawbacks to using these devices remain. For example, the TREVO 2 study (Thrombectomy Revascularisation of Large Vessel Occlusions in AIS) was an open label, multi-center trial evaluating the efficacy of the Trevo Pro retriever (Stryker Neurovascular, Fremont, USA) with the Merci device in patients with large vessel ischemic stroke (Nogueira R. G. et al. Lancet 2012; 380: 1231-40). Symptomatic intra cranial hemorrhage (ICH) occurred in 6.8% in the Trevo group and in 8.9% of the Merci group, with mortality rates of 33% and 24% respectively. The outcome of this trial suggests that there are unique mechanical mechanisms of action and consequently dissimilar success and efficacy rates depending on the thrombectomy approaches applied (Singh P. et al. J Neurosci Rural Pract. 2013 July-September; 4(3): 298-303).

Furthermore, some blood vessel occlusions are resistant to recanalization by a particular thrombectomy device due to the characteristics of the thrombus (e.g. a "hard" thrombus) and the particular blood vessel where the occlusion is located (Papanagiotou, P., and White, C. J., Endovascular Reperfusion Strategies for Acute Stroke, JACC: Cardiovascular Interventions, 2016, Vol. 9, No. 4, pg. 315).

Thus, at present, there does not appear to be a universally superior mechanical thrombectomy device that provides sufficient aspiration force without obstructing aspiration, is manageable in terms of size and flexibility, and is quick/easy to remove while preventing emboli from going to end organs. There thus remains a need for mechanical thrombectomy devices and strategies. The disclosed invention addresses this unmet need.

SUMMARY OF THE INVENTION

The present invention is an element is a devise which provides a safe and reliable means of applying a simultaneous combination of irrigation, aspiration and maceration to a thrombi or similar material. In order further the device's purpose of safely and effectively performing thrombectomy or the like. More particularly, the present invention discloses a "string length adjustment mechanism" for a lasso, namely a mechanism to allow more lengths of string into "system", or alternatively to shorten the length of available string in the system, namely a ratchet, or a reel among others. Said system is part of a filter assembly that is openable and closeable while in use within a bodily vessel, by deployment of a string or wire arranged such that a lasso or drawstring type cincture is affected According to one aspect, the described invention provides an endovascular device including a semi-permeable flared filter or filtered-tipped catheter for capturing emboli while allowing passage therethrough of blood cells and serum, wherein the flared opening of the filter may be opened or closed by the user while deployed within a vessel. The present invention comprises a staffed conical filter having at least one string or wire capable of opening or collapsing said filter in the manner of a lasso or drawstring, with a string that communicates from an attachment point around the circumference of the filter opening, disposed within at least one channel or set of hoops about the rim of the filter, and down catheter element, and out a side hole. Alternatively, the string may have a small loop through which the wire subsequently passes after said wire goes around the entire circumference of the distal segment of the filter, in the manner of a typical lasso. The string or wire is expanded or contracted via a reeling or ratcheting mechanism through which it passes to outside a patient's body. A number of variant embodiments are disclosed, each implementing the lasso principle.

For disclosure purposes the term rim of the filter is a zone on a segment of the present invention's filter element which is capable of expanding maximally to abut the walls of a target vessel. The term attachment point means a zone on a region on the catheter around the circumference of the filter opening, at the base of the cone of the filter, at which the filter is adhered circumferentially to the catheter. The size of said segment and the size of said rim depend upon the size of the device of the present invention. In the preferred embodiment, the attachment point is a circular area of approximately 0.01 mm to 3 cm in length, diameter and the rim is a cylindrical area of 0.01 mm to 6 cm in length and a diameter of 0.5 mm-7 cm when the filter is fully expanded. The only limitation in location or size of either the rim or point, is mechanical. Said size or location must not prevent the filter element of the present invention from expanding or collapsing.

The present invention has numerous embodiments. These include a flared, semi-permeable filters, filtered-tipped catheters, reverse-flared filters, internal lumens, external lumens, among others. However, the present invention is simply the use of a lasso-type mechanism to open and close a catheter filter.

More particularly, the present invention has the following novel characteristics: combining the simultaneous irrigation, aspiration, and maceration; combining the simultaneous irrigation and aspiration to reverse flow, independent of maceration; combining the simultaneous irrigation and aspiration to reverse flow, independent of maceration, and retrieving clots by removing the bulk of the clot, and the induced flow reversal by the combination of simultaneous irrigation and aspiration make sure any clot pieces that break free are removed from the body via the aspiration, rather than embolizing distally and causing permanent tissue ischemia; using a balloon mounted aspiration catheter, designed to use at the face of an arterial thrombus, to occlude a vessel and facilitate flow reversal via aspiration and simultaneous distal irrigation; using a filter-tip aspiration catheter—for use in most venous and dialysis av graft de-clot cases; using the present with addition of IVUS to monitor flow and clot build-up at the tip of the catheter (particularly the preferred embodiment of the present invention, at the catheter tip in the filter-tip aspiration catheter version); using the present invention (particularly in the aspiration catheter, balloon mounted, and/or filter-tip aspiration catheter) with the addition of a vibrational wire in or distal to the catheter, to break up the clot to avoid the aspirating catheter becoming clogged with large pieces of clot; and using the sinusoidal hypo-tube embodiment of the present invention that has an eggbeater like-maceration effect, while simultaneously irrigating into and beyond the clot and aspirating to remove the clot. The present invention's vibrational wire may be used with any aspiration catheter and/or balloon mounted aspiration catheter as well.

The present invention's filter-tip aspirator catheter can also be used in select cases of peripheral arterial thrombectomies. The prerequisite in such cases is the ability to access the artery downstream from a clot. This is usually not possible for arterial emboli in the brain, but may be possible for arteries in arms and legs. A non-limiting example is an axillary artery embolus/thrombus, where a person of ordinary skill can obtain access proximal to the clot from femoral access, and/or a person of ordinary skill can also access distally (downstream) via a brachial or radial artery approach.

A medical device according to the present invention generally includes a combination of three elements from the prior art, namely irrigation, aspiration and maceration for the purpose of safely and effectively performing thrombectomy, usually involving removal of thrombi (blood clots). More particularly, in preferred embodiment the present invention has a single switch that simultaneously starts a pump for irrigation, a vacuum for aspiration, and a rotational element for rotational maceration. Alternatively, if the present invention is used in an interventional suite or other environment which already has a "power injector" that can inject irrigation, then the preferred embodiment of the present invention would include a remote-control element to allow existing irrigation devices to be activated and deactivated simultaneously with the aspiration and maceration elements of the present invention. Additionally, the present invention may optionally be equipped to allow sequential/stepwise activation of each of the irrigation, aspiration and maceration features of the current invention.

To clarify, the present invention is a device and a method for using said device to overcome the medical difficulties associated with vessel collapse during a clot removal procedure. More particularly, the present invention introduces fluids such as a saline solution to a target clot simultaneously with the remove of parts of said target clot to maintain pressure inside a vessel from which said target clot is removed.

More specifically, removing target clots from a vessel is best done without damaging said vessel. Optimal devices and method remove said target clots by using existing access to said vessels, particularly other existing vessels. Removing said target clots using said optimal devices and methods have three significant difficulties. First said target clots are too large to use existing vessels as exit passages. The current invention, like other elements of prior art, uses mechanical means to reduce said target clots into two or more elements so as to allow the existing vessels to be used as exit passages.

This process results in the second significant difficulty, which is said two or more elements when separated from said target move in said existing vessels to cause difficulties elsewhere in body connected to said vessel. This second difficulty has been ameliorated by aspirating the said two or more elements. The current invention, like other elements of prior art, uses aspiration to ameliorate said second difficulty.

Said aspirating causes a third difficulty which is the collapse of said vessel. The present invention unlikely any prior are prevents said vessel collapse by replacing the mass of the target clot with material such as saline solution while simultaneously which removing said mass of the target clot.

More particularly, the present invention simultaneously irrigates aspirates and cuts clots. The irrigation both expands the vessel surrounding a targeted clot and replaces material removed by the present inventions rotating cutting element. The aspiration element removes both clot elements and excess fluid to prevent the vessel from exploding.

BRIEF DESCRIPTION OF THE DRAWINGS

FIG. 5A shows an illustration of a side view of one aspect of the endovascular device of the described invention.

FIG. 6 shows an illustration of a side view of one embodiment of the endovascular device of the described invention.

FIG. 7A shows an illustration of a side view of one embodiment of the endovascular device of the described invention.

FIG. 7B shows an illustration of a side view of one embodiment of the endovascular device of the described invention.

FIG. 8 show a cross-sectional view of one embodiment of the endovascular device of the described invention.

FIG. 11A shows a cross section side view of one embodiment of the endovascular device of the described invention.

FIG. 11B shows a cross section side view of one embodiment of the endovascular device of the described invention.

FIG. 12A shows a cross section side view of one embodiment of the endovascular device of the described invention.

FIG. 12B shows a cross section side view of one embodiment of the endovascular device of the described invention.

FIG. 13A shows a cross section side view of one embodiment of the endovascular device of the described invention.

FIG. 13B shows a cross section side view of one embodiment of the endovascular device of the described invention.

DETAILED DESCRIPTION OF THE INVENTION

Anatomical Terms

Figure 1:
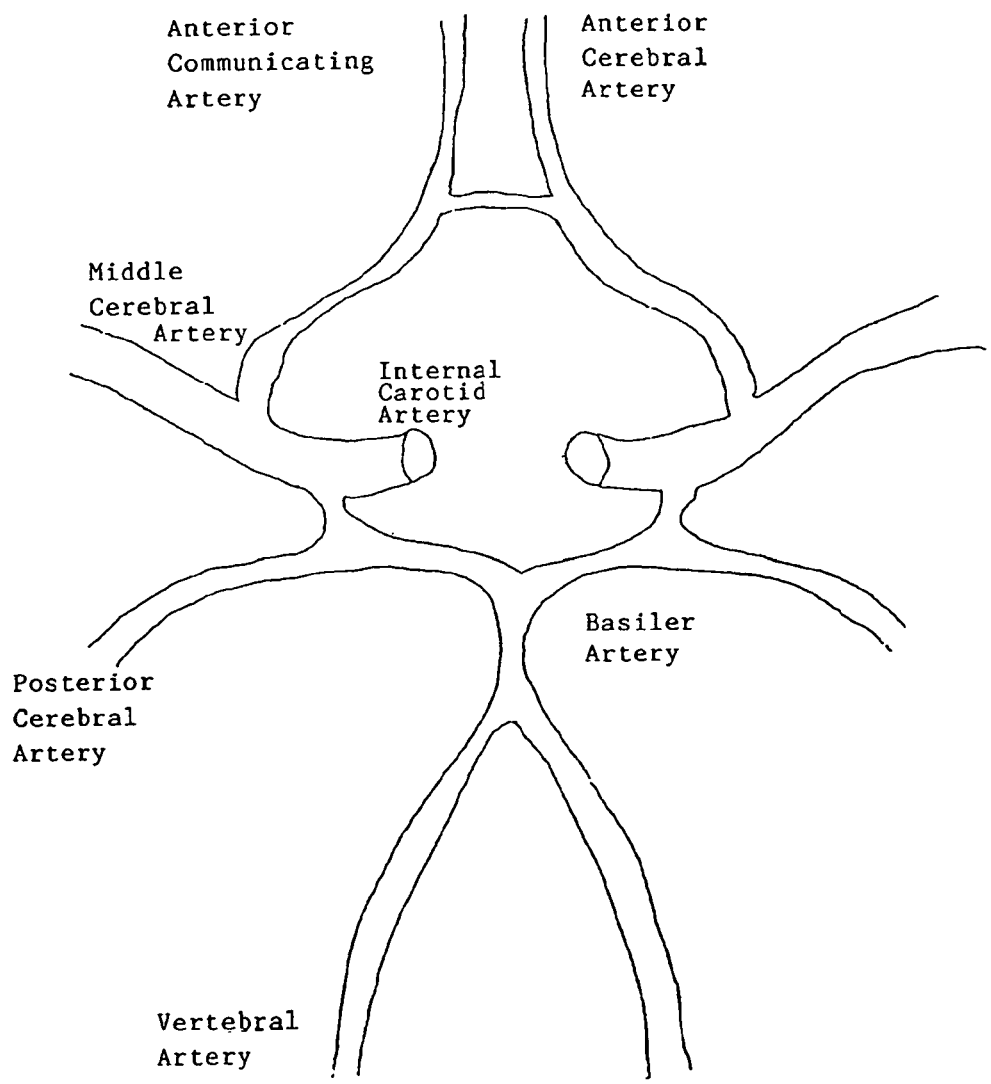
FIG. 1 shows an illustrative view of the cerebral arteries.
Figure 2:
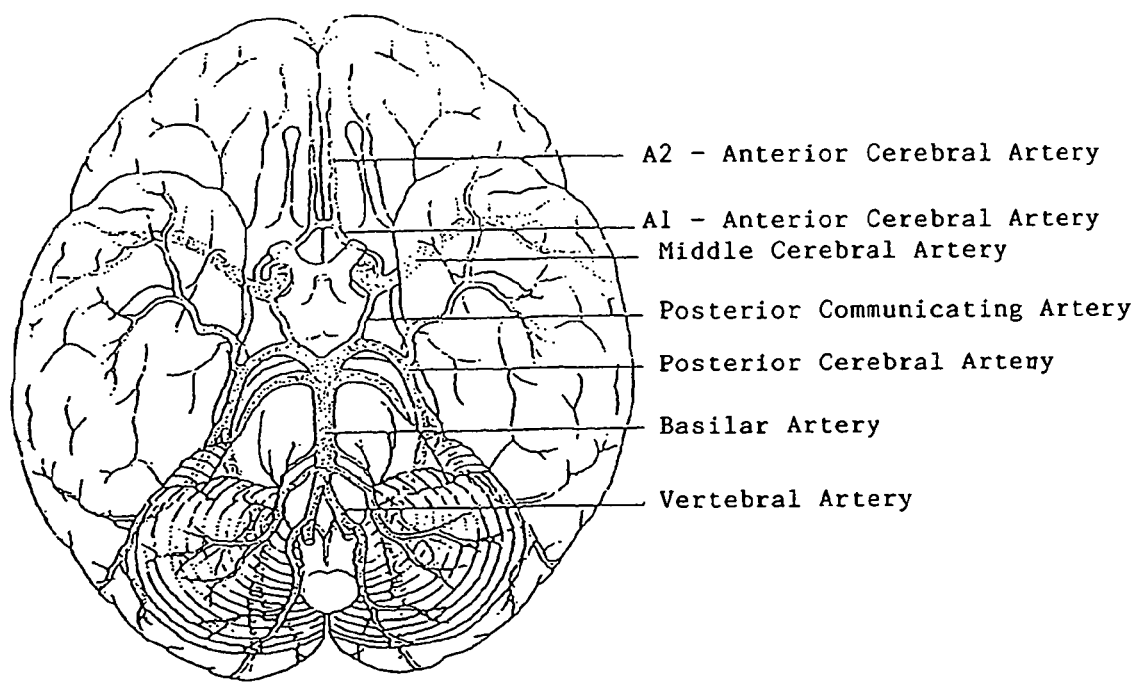
FIG. 2 shows an illustrative view of the cerebral arteries. (from Netter F H. The CIBA Collection of Medical Illustrations: Volumes 1, Nervous System. Vol. 1. Part I. CIBA: USA. 1986. pp. 256).

When referring to animals that typically have one end with a head and mouth, with the opposite end often having the anus and tail, the head end is referred to as the cranial end, while the tail end is referred to as the caudal end. Within the head itself, rostral refers to the direction toward the end of the nose, and caudal is used to refer to the tail direction. The surface or side of an animal's body that is normally oriented upwards, away from the pull of gravity, is the dorsal side; the opposite side, typically the one closest to the ground when walking on all legs, swimming or flying, is the ventral side. On the limbs or other appendages, a point closer to the main body is "proximal"; a point farther away is "distal". Three basic reference planes are used in zoological anatomy. A "sagittal" plane divides the body into left and right portions. The "midsagittal" plane is in the midline, i.e. it would pass through midline structures such as the spine, and all other sagittal planes are parallel to it. A "coronal" plane divides the body into dorsal and ventral portions. A "transverse" plane divides the body into cranial and caudal portions.

When referring to humans, the body and its parts are always described using the assumption that the body is standing upright. Portions of the body which are closer to the head end are "superior" (corresponding to cranial in animals), while those farther away are "inferior" (corresponding to caudal in animals). Objects near the front of the body are referred to as "anterior" (corresponding to ventral in animals); those near the rear of the body are referred to as "posterior" (corresponding to dorsal in animals). A transverse, axial, or horizontal plane is an X-Y plane, parallel to the ground, which separates the superior/head from the inferior/feet. A coronal or frontal plane is a Y-Z plane, perpendicular to the ground, which separates the anterior from the posterior. A sagittal plane is an X-Z plane, perpendicular to the ground and to the coronal plane, which separates left from right. The midsagittal plane is the specific sagittal plane that is exactly in the middle of the body.

Structures near the midline are called medial and those near the sides of animals are called lateral. Therefore, medial structures are closer to the midsagittal plane, lateral structures are further from the midsagittal plane. Structures in the midline of the body are median. For example, the tip of a human subject's nose is in the median line.

Ipsilateral means on the same side, contralateral means on the other side and bilateral means on both sides. Structures that are close to the center of the body are proximal or central, while ones more distant are distal or peripheral. For example, the hands are at the distal end of the arms, while the shoulders are at the proximal ends.

The term "aneurysm", as used herein, refers to a localized widening (dilatation) of an artery, a vein, or the heart. At the point of an aneurysm, there is typically a bulge, where the wall of the blood vessel or organ is weakened and may rupture.

Blood flow in most aneurysms is regular and predictable primarily according to the geometric relationship between the aneurysm and its parent artery. As blood flows within the parent artery with an aneurysm, divergence of blood flow, as occurs at the inlet of the aneurysm, leads to dynamic disturbances, producing increased lateral pressure and retrograde vortices that are easily converted to turbulence. Blood flow proceeds from the parent vessel into the aneurysm at the distal or downstream extent of the aneurysm neck (i.e., the transition from the sac to the parent artery), circulates around the periphery along the aneurysm wall from the neck to the top of the fundus (i.e., aneurysm sac) (downstream to upstream), returning in a type of "isotropic shower" along the aneurysm wall toward the neck region, and exits the closest extent of the aneurysm neck into the parent vessel (See, e.g., Strother C. M. Neuroradiology 1994; 36: 530-536; Moulder P. V. Physiology and biomechanics of aneurysms. In: Kerstein M D, Moulder P V, Webb W R, eds. *Aneurysms*. Baltimore, Md.: Williams & Wilkins; 1983:20).

As flow persists, areas of stagnation or vortices develop within a central zone of the aneurysm. These rotating vortices, formed at the entrance to the aneurysm at each systole (i.e., ventricle contraction) and then circulated around the aneurysm, are caused by the slipstreams or regions of recirculating flow rolling upon themselves when they enter the aneurysm at its downstream wall during systole. The stagnant vortex zone occurs in the center and at the fundus or upper portion of the aneurysm and becomes more pronounced in larger aneurysms. It is this stagnant zone that is believed to promote the formation of thrombi or blood clots, particularly in giant aneurysms (See, e.g., Gobin Y. P. et al. Neuroradiology 1994; 36: 530-536; Hademenos G. J. and Massoud T. F. Stroke 1997; 28: 2067-2077).

The term "abdominal aortic aneurysm" or "AAA", as used herein refers to an aortic diameter at least one and one-half times the normal diameter at the level of the renal arteries, which is approximately 2.0 cm. Generally, a segment of abdominal aorta with a diameter of greater than 3.0 cm is considered an aortic aneurysm. Aortic aneurysms constitute the 14th leading cause of death in the United States. Risk factors associated with AAA include age, sex, ethnicity, smoking, hypertension and atherosclerosis, among others (See, e.g., Aggarwal S. et al. Exp Clin Cardiol. 2011; 16(1): 11-15; Ouriel K. et al. J Vasc Surg. 1992; 15: 12-18; Silverberg E. et al. C A Cancer J Clin. 1990; 40: 9-26).

The term "arteriovenous malformation" ("AVM"), as used herein, refers to a tangle of abnormal and poorly formed blood vessels (e.g., arteries and veins) which have a higher than normal rate of bleeding compared to normal blood vessels.

AVMs are congenital vascular lesions that occur as a result of capillary mal-development between the arterial and venous systems. Approximately 0.14% of the United States population comprises an intracranial AVM that poses a significant risk and represents a major life threat, particularly to persons under the age of 50 years. The vessels constituting the AVM are weak and enlarged and serve as direct shunts for blood flow between the high-pressure arterial system and the low-pressure venous system, corresponding to a large pressure gradient and small vascular resistance. The abnormal low-resistance, high-flow shunting of blood within the brain AVM without an intervening capillary bed causes the fragile dilated vessels in the nidus (i.e., tangle of blood vessels) to become structurally abnormal and fatigued, to further enlarge, and to rupture (See, e.g., Wilkins R. H. Neurosurgery 1985; 16:421-430; Graves V. B. et al. Invest Radiol. 1990; 25: 952-960; Hademenos G. J. et al., Neurosurgery 1996; 38: 1005-1015).

The abnormal microvessels of an AVM serve as passive conduits for blood flow from the arterial circulation directly to the venous circulation, by-passing their normal physiological function of brain tissue perfusion. The hemodynamic consequences of an AVM occur as a result of two interdependent circulatory mechanisms involved in the shunting of blood between artery and vein (See, e.g., Hademenos G. J. and Massoud T. F. Stroke 1996; 27: 1072-1083).

In the normal cerebral circulation, blood flows under a high cerebrovascular resistance and high cerebral perfusion pressure. However, the presence of a brain AVM in the normal circulation introduces a second abnormal circuit of cerebral blood flow where the blood flow is continuously shunted under a high perfusion pressure through the AVM, possessing a low cerebrovascular resistance and low venous pressure. The clinical consequence of the abnormal shunt is a significant increase in blood returning to the heart (approximately 4 to 5 times the original amount, depending on the diameter and size of the shunt), resulting in a dangerous overload of the heart and cardiac failure. Volumetric blood flow through an AVM ranges from 200 mL/min to 800 mL/min and increases according to nidus size (See, e.g., Yamada S. Neurol Res. 1993; 15: 379-383).

The abnormal shunting of blood flow by brain AVMs rapidly removes or "steals" blood from the normal cerebral circulation and substantially reduces the volume of blood reaching the surrounding normal brain tissue. This phenomenon, known as cerebrovascular steal, depends on the size of the AVM and is the most plausible explanation for the development of progressive neurological deficits. Cerebrovascular steal could translate into additional neurological complications developed as a result of cerebral ischemia or stroke in neuronal territories adjacent to an AVM (See, e.g., Manchola I. F. et al. Neurosurgery 1993; 33: 556-562; Hademenos G. J. and Massoud T. F. Stroke 1997; 28: 2067-2077).

The term "arterial thrombosis", as used herein, refers to a thrombus that develops in an artery. Depending on where the clot forms, arterial thrombosis can cause one or more of myocardial infarction, stroke, and peripheral arterial disease.

The term "aspirate" and its grammatical forms as used herein refers to removal of a substance from a body cavity using suction.

The term "atherectomy", as used herein, refers to a minimally invasive endovascular surgery technique for removing atherosclerosis from blood vessels within the body by cutting plaque from the walls of a blood vessel.

The term "atherosclerosis" (also known as "hardening of the arteries") as used herein refers to a pathological process in which calcified lipid or fatty deposits from flowing blood accumulate along the innermost intimal layer of a vessel wall. Atherosclerotic plaques are found almost exclusively at the outer wall of one or both daughter vessels at major arterial bifurcations, including the carotid. Atherosclerosis and the development of arterial plaques are the products of a host of independent biochemical processes including the oxidation of low-density lipoproteins, formation of fatty streaks, and the proliferation of smooth muscle cells. As the plaques form, the walls become thick, fibrotic, and calcified. As a result, the lumen narrows, reducing the flow of blood to the tissues supplied by the artery (See, e.g., Hademenos G. J. and Massoud T. F. Stroke 1997; 28: 2067-2077;

Hademenos G. J. Am Scientist 1997; 85: 226-235; Woolf N., Davies M. J. Sci Am Science & Medicine 1994; 1: 38-47).

Atherosclerotic deposits promote the development of blood clots or the process of thrombosis, due in part, to flow obstruction and to high shear stresses exerted on the vessel wall by the blood. High wall shear stress mechanically damages the inner wall of the artery, initiating a lesion. Low wall shear stress encourages the deposition of particles on the artery wall, promoting the accumulation of plaque. Turbulence comprises also been implicated in atherosclerotic disease because it can increase the kinetic energy deposited in the vessel walls and because it can lead to areas of stasis, or stagnant blood flow, that promote clotting. The presence of atherosclerotic lesions introduces an irregular vessel surface, resulting in turbulent blood flow, thus causing the dislodgment of plaques of varying size into the bloodstream. Subsequently, the dislodged plaque lodges into a vessel of smaller size, preventing further passage of blood flow (See, e.g., Hademenos G. J. and Massoud T. F. Stroke 1997; 28: 2067-2077).

The term "atresia", as used herein, refers to the absence or abnormal narrowing of an opening or passage in the body. For example, aortic atresia refers to a rare congenital anomaly in which the aortic orifice is absent or closed.

The term "atrial fibrillation", as used herein, refers to an irregular and often fast heart rate which may cause symptoms such as heart palpitations, fatigue, and shortness of breath. Atrial fibrillation weakens the cardiac wall and introduces abnormalities in the physiological function of the heartbeat, which ultimately result in reduced systemic pressure, conditions of ischemia and stroke.

The term "blockage", as used herein, refers to an obstruction that makes the movement or flow of blood difficult or impossible. Non-limiting examples of material that comprises a blockage includes cell debris, cholesterol and fatty deposits, platelets or other cell types, and emboli.

The term "brachiocephalic trunk", also known as "innominate artery", as used herein, refers to a major vessel that supplies the head, neck and right arm. It is the first of three main branches of the aortic arch, which originates from the upward convexity. After arising in the midline, it courses upwards to the right, crossing the trachea, and bifurcates posteriorly to the right sternoclavicular joint into the right subclavian and right common carotid arteries. It typically measures 4-5 cm in length with a diameter of approximately 12 mm.

The term "brain aneurysm", as used herein, refers to a cerebrovascular disease that manifests as a pouching or ballooning of the vessel wall (i.e., vascular dilation). The vascular dilatation develops at a diseased site along the arterial wall into a distended sac of stressed and thinned arterial tissue. The fully developed cerebral aneurysm typically ranges in size from a few millimeters to 15 mm but can attain sizes greater than 2.5 cm. If left untreated, the aneurysm may continue to expand until it ruptures, causing hemorrhage, severe neurological complications and deficits, and possibly death (Hademenos G. J. and Massoud T. F. Stroke 1997; 28: 2067-2077; Hademenos G. J. Phys Today 1995; 48: 24-30).

The two main treatment options for a patient suffering from a brain aneurysm are (i) surgical clipping; and (ii) endovascular coiling. Surgical clipping is an intracranial procedure in which a small metallic clip is placed along the neck of the aneurysm. The clip prevents blood from entering into the aneurysm sac so that it no longer poses a risk for bleeding. The clip remains in place, causing the aneurysm to shrink and permanently scar. Endovascular coiling is a minimally invasive technique in which a catheter is inserted into the femoral artery and navigated through the blood vessels to the vessels of the brain and into the aneurysm. Coils are then packed into the aneurysm to the point where it arises from the blood vessel, thus preventing blood flow from entering the aneurysm. Additional devices, such as a stent or balloon, for example, may be needed to keep the coils in place.

The term "branch", as used herein, refers to something that extends from or enters into a main body or source; a division or offshoot from a main stem (e.g., blood vessels); one of the primary divisions of a blood vessel.

The term "cerebral venous sinus thrombosis" as used herein, refers to a blood clot that forms in the brain's venous sinuses, preventing blood from draining out of the brain.

The term "coarctation" or "coarctation of the aorta", as used herein, refers to a congenital narrowing of a short section of the aorta.

The terms "compound curves" and "multi-curves" are used interchangeably herein to refer to multiple deflection points along the length of a catheter. By way of example, two deflection points allow a catheter to be deflected into an "S" shape or the shape of a shepherd's hook.

The term "curve diameter", as used herein, refers to the furthest distance a catheter moves from its straight axis as it is being deflected. The curve diameter does not always remain constant during deflection and does not necessarily indicate the location of the catheter tip.

The term "deflection", as used herein, refers to movement of a catheter tip independent of the rest of the catheter.

The term "deep vein thrombosis", as used herein, refers to a blood clot in a vein deep in the body, usually in a lower leg, thigh, pelvis, or arm.

The term "dyscrasia", as used herein, refers to an abnormal or disordered state of the body or a bodily part. The term "blood dyscrasia", as used herein, refers to an abnormality of blood cells or of clotting elements.

The term "embolus" (plural "emboli"), as used herein, refers to a gaseous or particulate matter that acts as a traveling "clot". A common example of an embolus is a platelet aggregate dislodged from an atherosclerotic lesion. The dislodged platelet aggregate is transported by the bloodstream through the cerebrovasculature until it reaches a vessel too small for further propagation. The clot remains there, clogging the vessel and preventing blood flow from entering the distal vasculature. Emboli can originate from distant sources such as the heart, lungs, and peripheral circulation, which may eventually travel within the cerebral blood vessels, obstructing flow and causing stroke. Other sources of emboli include atrial fibrillation and valvular disease. The severity of stroke depends on the size of the embolus and the location of the obstruction. The bigger the embolus and the larger the vessel obstruction, the larger the territory of brain at risk (Hademenos G. J. and Massoud T. F. Stroke 1997; 28: 2067-2077). The term "endoluminal", as used herein, refers to the state of being within a tubular organ or structure (e.g., blood vessel, duct, gastrointestinal tract, etc.) or within a lumen.

The term "endovascular thrombectomy" or "mechanical thrombectomy", as used herein, refers to a procedure that physically removes a thrombus from a blood vessel. The procedure may involve a long catheter with suction, rotating device, high-speed fluid jet, or ultrasound device that is used to physically break up and/or remove a thrombus in the blood vessel. Subgroups of this procedure include "proximal endovascular thrombectomy," wherein suction thrombectomy devices remove occlusive material from the blood vessel by aspiration, and "distal endovascular thrombectomy," wherein clot removal devices physically seize occlusive material and drag it out of the blood vessel (Singh P., et al., Endovascular treatment of acute ischemic stroke, J Neurosci Rural Pract. 2013 July-September; 4(3): 298-303). During proximal endovascular thrombectomy, manual suction is done by moving forward an aspiration catheter at the proximal surface of the thrombus. Manual aspiration is then carried out and the aspiration catheter is taken back under continuous negative pressure. A variation of the proximal endovascular thrombectomy method comprises a dedicated reperfusion catheter attached to a pumping system applying constant aspiration. In contrast, in distal endovascular thrombectomy, the occlusion site comprises to be traversed with a microcatheter so as to deploy the device beyond the thrombus. The device is then pulled back into the thrombus and positioned within the clot, followed by withdrawal of the clot and the device out of the patient's body (See. e.g., Singh P., et al., Endovascular treatment of acute ischemic stroke, J Neurosci Rural Pract. 2013 July-September; 4(3): 298-303).

The term "French" (abbreviated "Fr" or "F" or "Fg" or "Ga" or "CH" or "Ch"), as used herein, is a system used to measure the diameter of a catheter. The French unit of measure is equivalent to three times the diameter in millimeters (mm). For example, 9 Fr is equivalent to a diameter of 3 mm.

The term "hypotube" as used herein refers to a small, micro or nanoradius tube of any length with micro-engineered features along its length.

The term "introducer", as used herein, refers to an instrument such as a tube or a sheath that is placed within a vein or artery for introduction of a flexible device, for example, a catheter, needle, wire, etc.

The terms "ischemic" and "ischemia", as used herein, refer to deficient supply of blood to a body part generally due to obstruction of the inflow of arterial blood (e.g., by the narrowing of arteries, spasm or disease).

The term "lumen", as used herein, refers to the inner open space or cavity of a tubular structure.

The term "macerate" and its other grammatical forms as used herein refers to causing to separate into smaller parts.

The term "myocardial infarction", as used herein, refers to death of cells of an area of heart muscle as a result of oxygen deprivation, which in turn is caused by obstruction of the blood supply; commonly referred to as a "heart attack". The most common cause is thrombosis of an atherosclerotic coronary artery or a spasm. Less common causes included coronary artery abnormalities and vasculitis (inflammation of blood vessels).

The term "myocardial infarction with thrombus", as used herein, refers to an acute myocardial infarction caused by rupture of an atherosclerotic plaque that initiates blood clot (thrombus) formation, which totally or partially occludes a coronary artery.

The term "percutaneous coronary intervention" (PCI), as used herein, refers to a procedure that uses a catheter to place a stent at the site of an occlusion to open up blood vessels in the heart that have been narrowed by plaque buildup.

The term "recanalization", as used herein, refers to the process of restoring flow to or reuniting an interrupted channel of a bodily tube (e.g., a blood vessel).

The term "reperfusion", as used herein, refers to restoration of the flow of blood to a previously ischemic organ or tissue (e.g., heart or brain).

The term "retrievable thrombectomy stents", as used herein, refers to a self-expandable, re-sheathable, and re-constrainable stent-like thrombectomy device. Since it can be retrieved, it does not become a permanent implant, and while being recovered, it functions as a mechanical thrombectomy device. The entire removal of the device circumvents the drawbacks of permanent stent implantation, for example the requirement for double anti-platelet medication, which potentially adds to the risk of hemorrhagic complications and the risk of in-stent thrombosis or stenosis. Under general anesthesia, using a transfemoral approach, a guide catheter is positioned in the proximal internal carotid artery. A guide wire is advanced coaxially over a microcatheter within the blocked intracranial vessel and navigated past the thrombus. The microcatheter is then advanced over the wire through the clot, and the guide wire is substituted for the embolectomy device. The revascularization device is placed with the middle third of the device residing within the thrombus formation. The radial force of the stent retriever is capable of instantly creating a channel by squeezing the thrombus, and of partially restore blood flow to the distal territory in the majority of cases, producing a channel for a temporary bypass. The device is usually left in place for an embedding time up to 10 minutes, permitting entrapment of the thrombus within the stent struts. To extract the thrombus, the unfolded stent and the microcatheter are slowly dragged into the guide catheter with flow reversal by continuous aspiration (Singh P. et al. J Neurosci Rural Pract. 2013 July-September; 4(3): 298-303).

The term "self-expanding stents", as used herein, refers to a cylindrical mesh that is positioned at the site of a blood vessel occlusion and expanded, thereby stretching the blood vessel wall. Self-expanding stents are manufactured at (or slightly above) the diameter of a blood vessel and are crimped and constrained to a smaller diameter until the intended delivery site is reached. The constraint is then removed and the stent is deployed.

The term "slant height" of a cone, as used herein, refers to the length measured along a lateral face from the base to the apex along the "center" of the face. For example, the slant height "l" of a right circular cone is the distance from the apex to a point on the base, and is related to the height "h" and base radius "a" by the equation: $l=\sqrt{h^2+a^2}$.

The term "stenosis" as used herein refers to an abnormal narrowing of a passage in the body. The term "restenosis", as used herein, refers to the recurrence of this abnormal narrowing (e.g., of a blood vessel (e.g., artery or vein) or valve).

The term "steerability", as used herein, refers to an ability to turn or rotate the distal end of a catheter with like-for-like movement of the proximal section or the catheter handle.

The terms "subject" or "individual" or "patient" are used interchangeably to refer to a member of an animal species of mammalian origin, including but not limited to, mouse, rat, cat, goat, sheep, horse, hamster, ferret, pig, dog, guinea pig, rabbit and a primate, such as, for example, a monkey, ape, or human.

The phrase "subject in need thereof" as used herein refers to a patient that (i) will be treated with a device of the described invention, (ii) is receiving treatment with a device of the described invention; or (iii) comprises received treatment with a device of the described invention, unless the context and usage of the phrase indicates otherwise.

The term "stroke", "acute stroke" or "cerebrovascular accident", as used herein, refers to neurological signs and symptoms, usually focal and acute, which result from diseases involving blood vessels of the brain. Generally, strokes are either occlusive (due to closure of a blood vessel) or hemorrhagic (due to bleeding from a vessel). Although most occlusive strokes are due to atherosclerosis and thrombosis, and most hemorrhagic strokes are associated with hypertension or aneurysms, strokes of either type may occur at any age from many causes, including cardiac disease, trauma, infection, neoplasm, blood dyscrasia, vascular malformation, immunological disorder, and exogenous toxins. An ischemia stroke results from a lack of blood supply and oxygen to the brain that occurs when reduced perfusion pressure distal to an abnormal narrowing (stenosis) of a blood vessel is not compensated by autoregulatory dilation of the resistance vessels. When ischemia is sufficiently severe and prolonged, neurons and other cellular elements die. This condition is referred to as "cerebral infarction" (See, e.g., Hart R. G. et al., Stroke 1990; 21:1111-1121). Although the consequences of both ischemic and hemorrhagic stroke are similar (i.e., vessel obstruction, resultant reduced blood flow to the brain, neurological deficits and possibly death), the biophysical and hemodynamic mechanisms behind the obstruction of blood flow are different. Biophysical mechanisms for the development of obstructions that ultimately lead to stroke can arise by six distinct processes: atherosclerosis, embolus, thrombus, reduced systemic pressure, hemorrhage, and vasospasm (See, e.g., Hademenos G. J. and Massoud T. F., Stroke 1997; 28: 2067-2077).

The term "taper", as used herein, refers to a reduction of thickness toward one end; the gradual diminution of width or thickness in an elongated object; i.e., to become more slender toward one end.

The term "thrombectomy", as used herein, refers to the surgical excision of a thrombus.

The term "thrombus", as used herein, refers to an internal physiological mechanism responsible for the clotting of blood. A thrombus is an aggregation of platelets and fibrin formed in response either to an atherosclerotic lesion or to vessel injury. In response to vessel or tissue injury, the blood coagulation system is activated, which initiates a cascade of processes, transforming prothrombin, ultimately resulting in a fibrin clot (Prothrombin→Thrombin→Fibrinogen→Fibrin→Fibrin Clot) (See, e.g., Hademenos G. J. and Massoud T. F. Stroke 1997; 28: 2067-2077).

Although a host of mechanisms and causes are responsible for vessel injury, vessel injury can occur as a result of forces (e.g., shear stresses) coupled with excess energy created by the turbulent flow exerted against the inner (intimal) lining of the vessel wall, particularly an atherosclerotic vessel wall (See, e.g., Fry D. L. Circ Res. 1968; 22: 165-197; Stein P. D. and Sabbah H. N. Circ Res. 1974; 35: 608-614; Mustard J. F. et al. Am J Med. 1962; 33: 621-647; Goldsmith H. L. et al. Thromb Haemost 1986; 55: 415-435).

The term "tortuosity" and other grammatical forms of the term "tortuous" is used herein to refer to a property of a tube, passage or blood vessel (e.g., an artery or a vein) being twisted, crooked or having many turns.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in patients that have previously had the disorder(s); and (e) limiting recurrence of symptoms in patients that were previously asymptomatic for the disorder(s).

The term "vasospasm", as used herein, refers to the sudden constriction of a blood vessel, reducing its diameter and flow rate. When bleeding occurs in the subarachnoid space, the arteries in the subarachnoid space can become spastic with a muscular contraction, which can produce a focal constriction of sufficient severity to cause total occlusion. The length of time that the vessel is contracted during vasospasm varies from hours to days. However, regardless of the Page 52 duration of vessel constriction, reduction of blood flow induces cerebral ischemia, thought to be reversible within the first 6 hours and irreversible thereafter. It comprises been shown that vasospasm is maximal between 5 and 10 days after subarachnoid hemorrhage and can occur up to 2 weeks after subarachnoid hemorrhage (See, e.g., Wilkins R. H. Contemp Neurosurg. 1988; 10:1-66; Hademenos G. J. and Massoud T. F. Stroke 1997; 28: 2067-2077).

The term "venous thrombosis", as used herein, refers to a thrombus that forms within a vein. A common form of venous thrombosis is deep vein thrombosis, in which the thrombus can break off, flow toward the lungs, and become a pulmonary embolism.

In the various views of the drawings, like reference characters designate like or similar parts.

Figure 3:
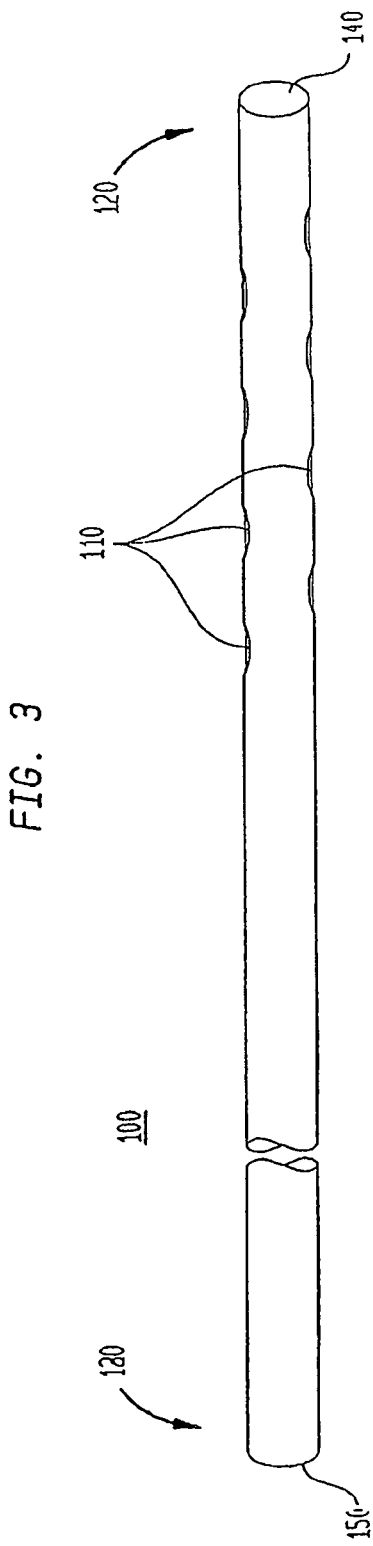
FIG. 3 shows an illustration of a side view of one aspect of the endovascular device of the described invention.

FIG. 3 shows a non-limiting example of one aspect of an endovascular device of the described invention. According to one possible configuration, FIG. 3 illustrates a side view of a microcatheter 100 with side holes 110 located around the circumference of the distal end 120 of the microcatheter 100. According to some embodiments, the microcatheter 100 further comprises a front hole 140 located at a tip of the distal end 120 of the microcatheter and a rear hole 150 located at a tip of the proximal end 130 of the microcatheter. Rear hole 150 is capable of receiving a fluid from outside a patient's body, and each of the side holes 110 and the front hole 140 are capable of ejecting fluid out of the microcatheter 100 into the vasculature of a patient.

According to some embodiments, variables include, without limitation, the number of side holes, the spacing of the side holes, the proximity of the side holes to the distal end, the length over which the side holes exist, the shape of the side holes, the diameter of the side holes, catheter wall thickness, and internal and outer diameter of the catheter.

According to some embodiments, the side holes 110 are evenly spaced around the circumference of the microcatheter 100. According to some embodiments, the side holes are randomly spaced around the circumference of the microcatheter 100. According to some embodiments, the side holes 110 are spaced in a repeating pattern around the circumference of the microcatheter 100.

According to some embodiments, the side holes 110 are located on the distal end 120 of the microcatheter 100 for a length of from 0.1 to 60 cm. According to some embodiments, the side holes 110 are present over a length of at least 0.1 cm on the distal end 120 of the microcatheter within the last 60 cm of the distal end 120 of the microcatheter 100. According to some embodiments, the side holes 110 are present over a length of at least 0.5 cm on the distal end 120 of the microcatheter within the last 60 cm of the distal end 120 of the microcatheter 100. According to some embodiments, the side holes 110 are present over a length of at least 1 cm on the distal end 120 of the microcatheter within the last 60 cm of the distal end 120 of the microcatheter 100. According to some embodiments, the side holes 110 are present over a length of at least 5 cm on the distal end 120 of the microcatheter within the last 60 cm of the distal end 120 of the microcatheter 100. According to some embodiments, the side holes 110 are present over a length of at least 10 cm on the distal end 120 of the microcatheter within the last 60 cm of the distal end 120 of the microcatheter 100. According to some embodiments, the side holes 110 are present over a length of at least 20 cm on the distal end 120 of the microcatheter within the last 60 cm of the distal end 120 of the microcatheter 100. According to some embodiments, the side holes 110 are present over a length of at least 30 cm on the distal end 120 of the microcatheter within the last 60 cm of the distal end 120 of the microcatheter 100. According to some embodiments, the side holes 110 are present over a length of at least 40 cm on the distal end 120 of the microcatheter within the last 60 cm of the distal end 120 of the microcatheter 100. According to some embodiments, the side holes 110 are present over a length of at least 50 cm on the distal end 120 of the microcatheter within the last 60 cm of the distal end 120 of the microcatheter 100. According to some embodiments, the side holes 110 are present over a length of at least 60 cm on the distal end 120 of the microcatheter within the last 60 cm of the distal end 120 of the microcatheter 100.

According to some embodiments, the side holes 110 are located on the last 0.5 cm of the distal end 120 of the microcatheter 100. According to some embodiments, the side holes 110 are located on the last 1 cm of the distal end 120 of the microcatheter 100. According to some embodiments, the side holes 110 are located on the last 3 cm of the distal end 120 of the microcatheter 100. According to some embodiments, the side holes 110 are located on the last 5 cm of the distal end 120 of the microcatheter 100. According to some embodiments, the side holes 110 are located on the last 10 cm of the distal end 120 of the microcatheter 100. According to some embodiments, the side holes 110 are located on the last 15 cm of the distal end 120 of the microcatheter 100. According to some embodiments, the side holes 110 are located on the last 20 cm of the distal end 120 of the microcatheter 100. According to some embodiments, the side holes 110 are located on the last 25 cm of the distal end 120 of the microcatheter 100. According to some embodiments, the side holes 110 are located on the last 30 cm of the distal end 120 of the microcatheter 100. According to some embodiments, the side holes 110 are located on the last 35 cm of the distal end 120 of the microcatheter 100. According to some embodiments, the side holes 110 are located on the last 40 cm of the distal end 120 of the microcatheter 100. According to some embodiments, the side holes 110 are located on the last 45 cm of the distal end 120 of the microcatheter 100. According to some embodiments, the side holes 110 are located on the last 50 cm of the distal end 120 of the microcatheter 100. According to some embodiments, the side holes 110 are located on the last 55 cm of the distal end 120 of the microcatheter 100. According to some embodiments, the side holes 110 are located on the last 60 cm of the distal end 120 of the microcatheter 100. According to some embodiments, the side holes 110 are located along greater than the last 60 cm of the distal end 120 of the microcatheter 100.

According to some embodiments, the side holes 110 are of a circular shape. According to some embodiments, the side holes 110 are of an oval shape. According to some embodiments, the side holes 110 are of a square shape. According to some embodiments, the side holes 110 are of a rectangular shape. In some embodiment, the side holes 110 are of a triangular shape. According to some embodiments, the side holes 110 are of a trapezoidal shape. According to some embodiments, the side holes 110 are of a diamond shape. According to some embodiments, the side holes 110 are of a pentagon shape. According to some embodiments, the side holes 110 are of a hexagon shape. According to some embodiments, the side holes 110 are of a heptagon shape. According to some embodiments, the side holes 110 are of an octagon shape. According to some embodiments, the side holes 110 are of a nonagon shape. According to some embodiments, the side holes 110 are of a decagon shape. According to some embodiments, the side holes 110 are of an irregular shape. According to some embodiments, the side holes 110 are of a mixture of two or more of circular, oval, square, rectangle, triangle, diamond, pentagon, hexagon, heptagon, octagon, nonagon, decagon, and irregular shapes.

According to some embodiments, the size of the side holes 110 is greater than the size of the front hole 140 on the distal end 120 of the microcatheter 100. According to some embodiments, the size of the side holes 110 is less than the size of the front hole 140 on the distal end 120 of the microcatheter 100. According to some embodiments, the size of the side holes 100 is approximately the same as the size of the front hole 140 on the distal end 120 of the microcatheter 100.

According to some embodiments, the opening of a side hole 110 is at an angle relative to the opening of the front hole 140. According to some embodiments, the opening of a side hole 110 is at a 90-degree angle relative to the opening of the front hole. According to some embodiments, the opening of a side hole 110 is at least at a 10-degree angle relative to the opening of the front hole. According to some embodiments, the opening of a side hole 110 is at least at a 20-degree angle relative to the opening of the front hole. According to some embodiments, the opening of a side hole 110 is at least at a 30-degree angle relative to the opening of the front hole. According to some embodiments, the opening of a side hole 110 is at least at a 40-degree angle relative to the opening of the front hole. According to some embodiments, the opening of a side hole 110 is at least at a 50-degree angle relative to the opening of the front hole. According to some embodiments, the opening of a side hole 110 is at least at a 60-degree angle relative to the opening of the front hole. According to some embodiments, the opening of a side hole 110 is at least at a 70-degree angle relative to the opening of the front hole. According to some embodiments, the opening of a side hole 110 is at least at an 80-degree angle relative to the opening of the front hole. According to some embodiments, the opening of a side hole 110 is at least at a 100-degree angle relative to the opening of the front hole. According to some embodiments, the opening of a side hole 110 is at least at a 120-degree angle relative to the opening of the front hole. According to some embodiments, the opening of a side hole 110 is at least at a 130-degree angle relative to the opening of the front hole. According to some embodiments, the opening of a side hole 110 is at least at a 140-degree angle relative to the opening of the front hole. According to some embodiments, the opening of a side hole 110 is at least at a 150-degree angle relative to the opening of the front hole. According to some embodiments, the opening of a side hole 110 is at least at a 160-degree angle relative to the opening of the front hole. According to some embodiments, the opening of a side hole 110 is at least at a 170-degree angle relative to the opening of the front hole. According to some embodiments, a plurality of side holes 110 is at the same angle relative to the front hole 140. According to some embodiments, a plurality of side holes 110 is at different angles relative to the front hole 140.

According to some embodiments, the microcatheter 100 comprises an outer diameter between 34 French and 0.1 French. According to some embodiments, the microcatheter 100 comprises an outer diameter of less than 34 French. According to some embodiments, the microcatheter 100 comprises an outer diameter of less than 32 French. According to some embodiments, the microcatheter 100 comprises an outer diameter of less than 30 French. According to some embodiments, the microcatheter 100 comprises an outer diameter of less than 28 French. According to some embodiments, the microcatheter 100 comprises an outer diameter of less than 26 French. According to some embodiments, the microcatheter 100 comprises an outer diameter of less than 24 French. According to some embodiments, the microcatheter 100 comprises an outer diameter of less than 22 French. According to some embodiments, the microcatheter 100 comprises an outer diameter of less than 20 French. According to some embodiments, the microcatheter 100 comprises an outer diameter of less than 19 French. According to some embodiments, the microcatheter 100 comprises an outer diameter of less than 18 French. According to some embodiments, the microcatheter 100 comprises an outer diameter of less than 17 French. According to some embodiments, the microcatheter 100 comprises an outer diameter of less than 16 French. According to some embodiments, the microcatheter 100 comprises an outer diameter of less than 15 French. According to some embodiments, the microcatheter 100 comprises an outer diameter of less than 14 French. According to some embodiments, the microcatheter 100 comprises an outer diameter of less than 13 French. According to some embodiments, the microcatheter 100 comprises an outer diameter of less than 12 French. According to some embodiments, the microcatheter 100 comprises an outer diameter of less than 11 French. According to some embodiments, the microcatheter 100 comprises an outer diameter of less than 10 French. According to some embodiments, the microcatheter 100 comprises an outer diameter of less than 9 French. According to some embodiments, the microcatheter 100 comprises an outer diameter of less than 8 French. According to some embodiments, the microcatheter 100 comprises an outer diameter of less than 7 French. According to some embodiments, the microcatheter 100 comprises an outer diameter of less than 6 French. According to some embodiments, the microcatheter 100 comprises an outer diameter of less than 5 French. According to some embodiments, the microcatheter 100 comprises an outer diameter of less than 4 French. According to some embodiments, the microcatheter 100 comprises an outer diameter of less than 3 French. According to some embodiments, the microcatheter 100 comprises an outer diameter of less than 2 French. According to some embodiments, the microcatheter 100 comprises an outer diameter of less than 1 French.

According to some embodiments, the side holes 110 are of a width at their widest point of between 17 French and 0.01 French. According to some embodiments, the side holes 110 are of a width at their widest point of less than 17 French. According to some embodiments, the side holes 110 are of a width at their widest point of less than 16 French. According to some embodiments, the side holes 110 are of a width at their widest point of less than 15 French. According to some embodiments, the side holes 110 are of a width at their widest point of less than 14 French. According to some embodiments, the side holes 110 are of a width at their widest point of less than 13 French. According to some embodiments, the side hole 110 have a width at their widest point of less than 12 French. According to some embodiments, the side holes 110 are of a width at their widest point of less than 11 French. According to some embodiments, the side holes 110 are of a width at their widest point of less than 10 French. According to some embodiments, the side holes 110 are of a width at their widest point of less than 9 French. According to some embodiments, the side holes 110 are of a width at their widest point of less than 8 French. According to some embodiments, the side holes 110 are of a width at their widest point of less than 7 French. According to some embodiments, the side holes 110 are of a width at their widest point of less than 6 French. According to some embodiments, the side holes 110 are of a width at their widest point of less than 5 French. According to some embodiments, the side holes 110 are of a width at their widest point of less than 4 French. According to some embodiments, the side holes 110 are of a width at their widest point of less than 3 French. According to some embodiments, the side holes 110 are of a width at their widest point of less than 2 French. According to some embodiments, the side holes 110 are of a width at their widest point of less than 1 French. According to some embodiments, the side holes 110 are of a width at their widest point of less than 0.1 French. According to some embodiments, the side holes 110 are of a width at their widest point of less than 0.01 French.

According to some embodiments, the luminal space defined by the microcatheter 100 is of a diameter between 32 French and 0.1 French. According to some embodiments, the luminal space defined by the microcatheter 100 is of a diameter of less than 32 French. According to some embodiments, the luminal space defined by the microcatheter 100 is of a diameter of less than 30 French. According to some embodiments, the luminal space defined by the microcatheter 100 is of a diameter of less than 28 French. According to some embodiments, the luminal space defined by the microcatheter 100 is of a diameter of less than 26 French. According to some embodiments, the luminal space defined by the microcatheter 100 is of a diameter of less than 24 French. According to some embodiments, the luminal space defined by the microcatheter 100 is of a diameter of less than 22 French. According to some embodiments, the luminal space defined by the microcatheter 100 is of a diameter of less than 20 French. According to some embodiments, the luminal space defined by the microcatheter 100 is of a diameter of less than 19 French. According to some embodiments, the luminal space defined by the microcatheter 100 is of a diameter of less than 18 French. According to some embodiments, the luminal space defined by the microcatheter 100 is of a diameter of less than 17 French. According to some embodiments, the luminal space defined by the microcatheter 100 is of a diameter of less than 16 French. According to some embodiments, the luminal space defined by the microcatheter 100 is of a diameter of less than 15 French. According to some embodiments, the luminal space defined by the microcatheter 100 is of a diameter of less than 14 French. According to some embodiments, the luminal space defined by the microcatheter 100 is of a diameter of less than 13 French. According to some embodiments, the luminal space defined by the microcatheter 100 is of a diameter of less than 12 French. According to some embodiments, the luminal space defined by the microcatheter 100 is of a diameter of less than 11 French. According to some embodiments, the luminal space defined by the microcatheter 100 is of a diameter of less than 10 French. According to some embodiments, the luminal space defined by the microcatheter 100 is of a diameter of less than 9 French. According to some embodiments, the luminal space defined by the microcatheter 100 is of a diameter of less than 8 French. According to some embodiments, the luminal space defined by the microcatheter 100 is of a diameter of less than 7 French. According to some embodiments, the luminal space defined by the microcatheter 100 is of a diameter of less than 6 French. According to some embodiments, the luminal space defined by the microcatheter 100 is of a diameter of less than 5 French. According to some embodiments, the luminal space defined by the microcatheter 100 is of a diameter of less than 4 French. According to some embodiments, the luminal space defined by the microcatheter 100 is of a diameter of less than 3 French. According to some embodiments, the luminal space defined by the microcatheter 100 is of a diameter of less than 2 French. According to some embodiments, the luminal space defined by the microcatheter 100 is of a diameter of less than 1 French. According to some embodiments, the luminal space defined by the microcatheter 100 is of a diameter of less than 0.1 French. According to some embodiments, the luminal space defined by the microcatheter 100 is of a diameter of less than 0.01 French.

According to some embodiments, the microcatheter 100 is made from one or more of the following materials: silicone, polyurethane, polyethylene, polytetrafluoroethylene (PTFE), polyethylene terephthalate (PET), latex, and thermoplastic elastomers. According to some embodiments, the microcatheter 100 comprises an inner layer made of a first material, and an outer layer made from a second material. According to some embodiments, the microcatheter is reinforced with steel or other suitable material.

According to some embodiments, the microcatheter 100 is made of a material and is of dimensions able to withstand internal pressure between 0.1 and 1200 psi. According to some embodiments, the microcatheter 100 is able to withstand internal pressures greater than 0.1 psi. According to some embodiments, the microcatheter 100 is able to withstand internal pressures greater than 1 psi. According to some embodiments, the microcatheter 100 is able to withstand internal pressures greater than 5 psi. According to some embodiments, the microcatheter 100 is able to withstand internal pressures greater than 10 psi. According to some embodiments, the microcatheter 100 is able to withstand internal pressures greater than 20 psi. According to some embodiments, the microcatheter 100 is able to withstand internal pressures greater than 40 psi. According to some embodiments, the microcatheter 100 is able to withstand internal pressures greater than 80 psi. According to some embodiments, the microcatheter 100 is able to withstand internal pressures greater than 160 psi. According to some embodiments, the microcatheter 100 is able to withstand internal pressures greater than 320 psi. According to some embodiments, the microcatheter 100 is able to withstand internal pressures greater than 460 psi. According to some embodiments, the microcatheter 100 is able to withstand internal pressures greater than 920 psi. According to some embodiments, the microcatheter 100 is able to withstand internal pressures greater than 1000 psi. According to some embodiments, the microcatheter 100 is able to withstand internal pressures greater than 1200 psi.

According to some embodiments, the material allows for a variable pressure between the proximal end and the distal end. According to some embodiments, the microcatheter is able to withstand a greater pressure at the proximal end and a lesser pressure at the distal end. According to some embodiments, the pressure the microcatheter can withstand at the proximal end is greater than the pressure the microcatheter can withstand at the proximal end by a ratio of 1.5:1. According to some embodiments, the pressure the microcatheter can withstand at the proximal end is greater than the pressure the microcatheter can withstand at the proximal end by a ratio of 2:1. According to some embodiments, the pressure the microcatheter can withstand at the proximal end is greater than the pressure the microcatheter can withstand at the proximal end by a ratio of 3:1. According to some embodiments, the pressure the microcatheter can withstand at the proximal end is greater than the pressure the microcatheter can withstand at the proximal end by a ratio of 4:1. According to some embodiments, the pressure the microcatheter can withstand at the proximal end is greater than the pressure the microcatheter can withstand at the proximal end by a ratio of 5:1. According to some embodiments, the pressure the microcatheter can withstand at the proximal end is greater than the pressure the microcatheter can withstand at the proximal end by a ratio of 6:1. According to some embodiments, the pressure the microcatheter can withstand at the proximal end is greater than the pressure the microcatheter can withstand at the proximal end by a ratio of 7:1. According to some embodiments, the pressure the microcatheter can withstand at the proximal end is greater than the pressure the microcatheter can withstand at the proximal end by a ratio of 8:1. According to some embodiments, the pressure the microcatheter can withstand at the proximal end is greater than the pressure the microcatheter can withstand at the proximal end by a ratio of 9:1. According to some embodiments, the pressure the microcatheter can withstand at the proximal end is greater than the pressure the microcatheter can withstand at the proximal end by a ratio of 10:1.

According to some embodiments, the outer diameter of the microcatheter 100 at the proximal end 130 is approximately the same as the outer diameter of the microcatheter 100 at the distal end 120. According to some embodiments, the outer diameter of the microcatheter 100 at the proximal end 130 is greater than the outer diameter of the microcatheter 100 at the distal end 120. According to some embodiments, the outer diameter of the microcatheter 100 at the proximal end 130 is less than the outer diameter of the microcatheter 100 at the distal end 120. According to some embodiments, the outer diameter of the microcatheter 100 varies along the length of the microcatheter.

According to some embodiments, the inner luminal diameter of the microcatheter 100 at the proximal end 130 is approximately the same as the inner luminal diameter of the microcatheter 100 at the distal end 120. According to some embodiments, the inner luminal diameter of the microcatheter 100 at the proximal end 130 is greater than the inner luminal diameter of the microcatheter 100 at the distal end 120. According to some embodiments, the inner luminal diameter of microcatheter 100 at the proximal end 130 is less than the inner luminal diameter of the microcatheter 100 at the distal end 120.

According to some embodiments, the diameter of the microcatheter is adapted to provide fluid proximal, distal, or inside the site of an occlusion. According to some embodiments, the microcatheter 100 can be used to irrigate a blood vessel on the distal side of a thrombus, on a proximal side of a thrombus, or both. By way of non-limiting example, according to some embodiments the microcatheter 100 can be pushed through a thrombus in a proximal to distal direction. According to some embodiments, the microcatheter 100 can be used in conjunction with an aspirator to perform a direct aspiration first pass technique (ADAPT) to irrigate at and distal to a thrombus to prevent the creation of an empty vacuum distal to the thrombus. According to some such embodiments, the thrombus then is aspirated proximally so the catheter can pick up the clot.

According to some embodiments, the diameter of the microcatheter is adapted to provide fibrinolytics to the site of an occlusion. According to some embodiments, the microcatheter is adapted to provide fluid, fluid including saline solution, HEP-saline, neuro-protective cooled solution, and other neuro-protective liquids, proximal, distal, or inside the site of an occlusion. According to some embodiments, the diameter of the microcatheter is adapted to provide fluid while not obstructing suction of an aspirator.

Figure 4:
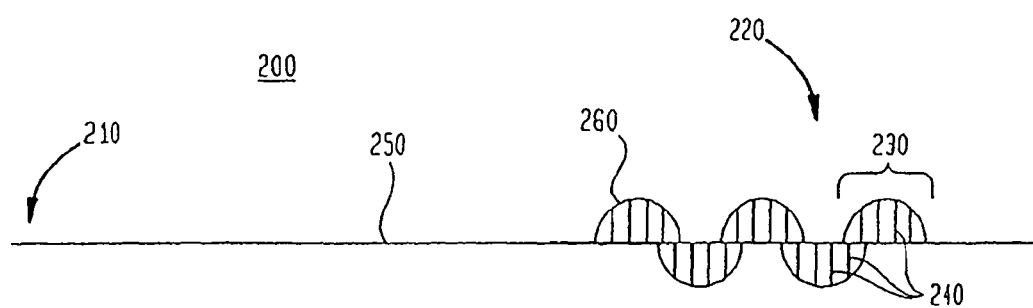
FIG. 4 shows an illustration of a side view of one aspect of the endovascular device of the described invention.
Figure 5B:
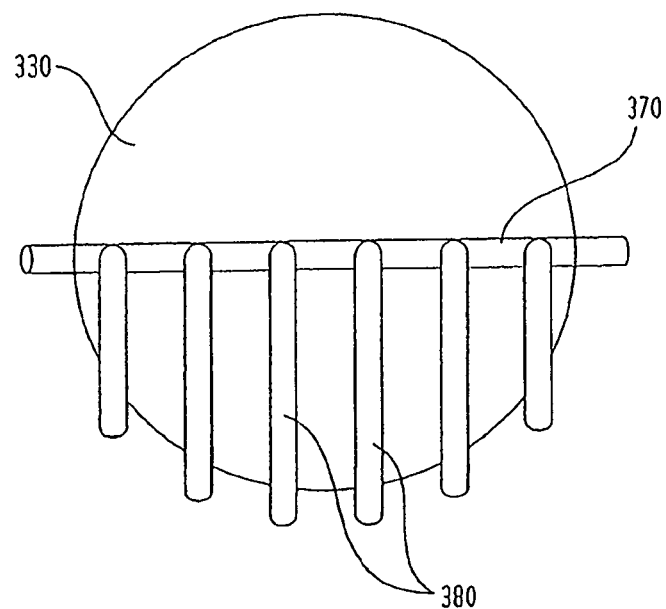
FIG. 5B shows a top view of one embodiment of the side hole and half loop structure of the described invention.
Figure 5C:
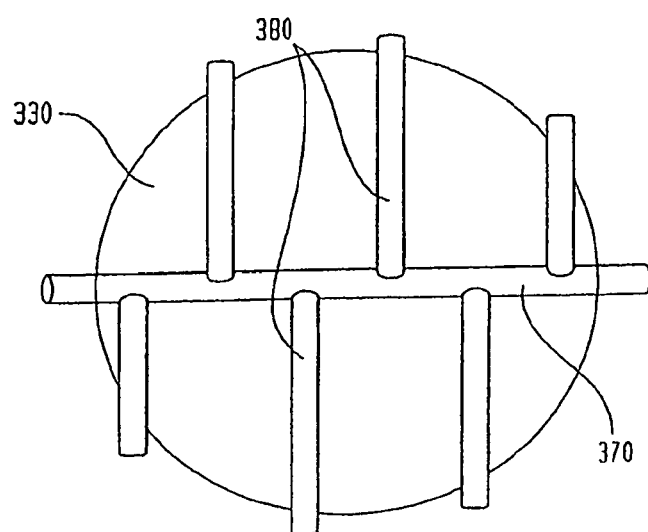
FIG. 5C shows a top view of one embodiment of the side hole and half loop structure of the described invention.
Figure 5D:
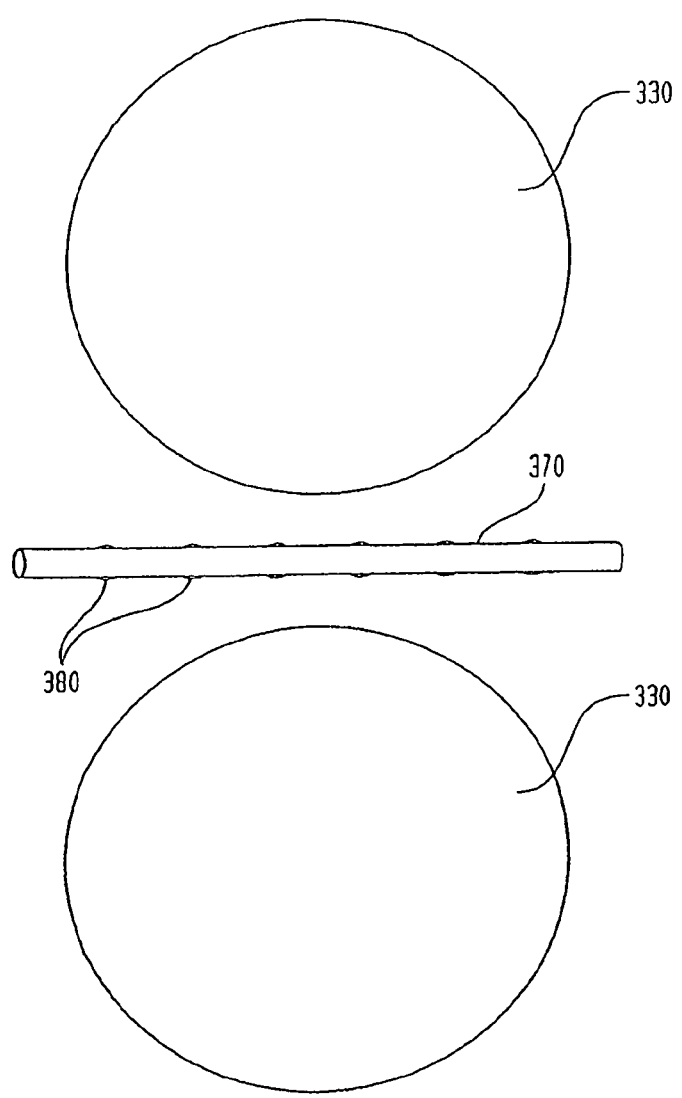
FIG. 5D shows a top view of one embodiment of the side hole and half loop structure of the described invention.

FIG. 4 shows an exemplary and non-limiting example of one aspect of the endovascular device of the described invention that includes macerating loops mounted on the microwire.

According to some embodiments, a macerating microwire 200 comprises a central wire 250 comprising a proximal end 210 and a distal end 220. Attached to the distal end of the microwire are one or more half-loop structures 230. According to some embodiments, the half loop-structures 230 comprise a second microwire with a first end and a second end, wherein both the first end and second end of the half-loop structure are attached to the central wire 250 of the macerating microwire, and cross strut wires 240 are connected to both the second microwire of the half-loop structure and the central wire 250 of the macerating microwire. Said cross-strut wires 240 may vary in size but are limited by the maximum interior radius of the vessel.

According to some embodiments, variables include, without limitation, the diameter of the central wire, size of the half loops, placement of the half loops, and construction of the half loops.

According to some embodiments, the proximal end 210 of the microwire 200 can be connected to a power-driven plug that rotates the macerating microwire 200 around the axis of the central wire 250. For example, the power-driven plug can be battery or electrically powered.

According to some embodiments, the diameter of the central wire 250 is between 0.1 inches and 0.001 inches. According to some embodiments, the diameter of the central wire 250 is between 0.09 and 0.002 inches. According to some embodiments, the diameter of the central wire 250 is between 0.08 and 0.003 inches. According to some embodiments, the diameter of the central wire 250 is between 0.07 and 0.004 inches. According to some embodiments, the diameter of the central wire 250 is between 0.06 and 0.005 inches. According to some embodiments, the diameter of the central wire 250 is between 0.05 and 0.006 inches. According to some embodiments, the diameter of the central wire 250 is between 0.04 and 0.007 inches. According to some embodiments, the diameter of the central wire 250 is between 0.03 and 0.008 inches. According to some embodiments, the diameter of the central wire 250 is between 0.02 and 0.009 inches. According to some embodiments, the diameter of the central wire 250 is between 0.01 and 0.009 inches.

According to some embodiments, the diameter of the central wire 250 is greater than 0.001 inches. According to some embodiments, the diameter of the central wire 250 is greater than 0.002 inches. According to some embodiments, the diameter of the central wire 250 is greater than 0.003 inches. According to some embodiments, the diameter of the central wire 250 is greater than 0.004 inches. According to some embodiments, the diameter of the central wire 250 is greater than 0.005 inches. According to some embodiments, the diameter of the central wire 250 is greater than 0.006 inches. According to some embodiments, the diameter of the central wire 250 is greater than 0.007 inches. According to some embodiments, the diameter of the central wire 250 is greater than 0.008 inches. According to some embodiments, the diameter of the central wire 250 is greater than 0.009 inches. According to some embodiments, the diameter of the central wire 250 is greater than 0.01 inches. According to some embodiments, the diameter of the central wire 250 is greater than 0.02 inches. According to some embodiments, the diameter of the central wire 250 is greater than 0.03 inches. According to some embodiments, the diameter of the central wire 250 is greater than 0.04 inches. According to some embodiments, the diameter of the central wire 250 is greater than 0.05 inches. According to some embodiments, the diameter of the central wire 250 is greater than 0.06 inches. According to some embodiments, the diameter of the central wire 250 is greater than 0.07 inches. According to some embodiments, the diameter of the central wire 250 is greater than 0.08 inches. According to some embodiments, the diameter of the central wire 250 is greater than 0.09 inches.

According to some embodiments, the diameter of the central wire 250 is less than 0.1 inches. According to some embodiments, the diameter of the central wire 250 is less than 0.05 inches. According to some embodiments, the diameter of the central wire 250 is less than 0.04 inches. According to some embodiments, the diameter of the central wire 250 is less than 0.03 inches. According to some embodiments, the diameter of the central wire 250 is less than 0.02 inches. According to some embodiments, the diameter of the central wire 250 is less than 0.01 inches. According to some embodiments, the diameter of the central wire 250 is less than 0.009 inches. According to some embodiments, the diameter of the central wire 250 is less than 0.008 inches. According to some embodiments, the diameter of the central wire 250 is less than 0.007 inches. According to some embodiments, the diameter of the central wire 250 is less than 0.006 inches. According to some embodiments, the diameter of the central wire 250 is less than 0.005 inches. According to some embodiments, the diameter of the central wire 250 is less than 0.004 inches. According to some embodiments, the diameter of the central wire 250 is less than 0.003 inches. According to some embodiments, the diameter of the central wire 250 is less than 0.002 inches. According to some embodiments, the diameter of the central wire 250 is less than 0.001 inches.

According to some embodiments, the diameter of the central wire 250 is 0.1 inches. According to some embodiments, the diameter of the central wire 250 is 0.05 inches. According to some embodiments, the diameter of the central wire 250 is 0.04 inches. According to some embodiments, the diameter of the central wire 250 is 0.03 inches. According to some embodiments, the diameter of the central wire 250 is 0.02 inches. According to some embodiments, the diameter of the central wire 250 is 0.01 inches. According to some embodiments, the diameter of the central wire 250 is 0.009 inches. According to some embodiments, the diameter of the central wire 250 is 0.008 inches. According to some embodiments, the diameter of the central wire 250 is 0.007 inches. According to some embodiments, the diameter of the central wire 250 is 0.006 inches. According to some embodiments, the diameter of the central wire 250 is 0.005 inches. According to some embodiments, the diameter of the central wire 250 is 0.004 inches. According to some embodiments, the diameter of the central wire 250 is 0.003 inches. According to some embodiments, the diameter of the central wire 250 is 0.002 inches. According to some embodiments, the diameter of the central wire 250 is 0.001 inches.

According to some embodiments, the central wire 250 terminates at the distal end 220 with a soft wire tip. According to some embodiments, the central wire 250 terminates at the distal end 220 with a soft round metal atraumatic ball tip.

According to some embodiments, the half loops 230 are comprised of wire of the same diameter as the central wire 250. According to some embodiments, the half loops 230 comprise a wire of a smaller diameter than the diameter of the central wire 250. According to some embodiments, the half loops 230 comprise a wire of a larger diameter than the diameter of the central wire 250. According to some embodiments, the diameter of the wire comprising the half loops 230 is of a diameter between 0.1 inches and 0.006 inches. According to some embodiments, the diameter of the wire comprising the half loops 230 is of a diameter between 0.006 inches and 0.008 inches. According to some embodiments, the diameter of the wire comprising the half loops 230 is less than 0.1 inches. According to some embodiments, the diameter of the wire comprising the half loops 230 is less than 0.05 inches. According to some embodiments, the diameter of the wire comprising the half loops 230 is less than 0.04 inches. According to some embodiments, the diameter of the wire comprising the half loops 230 is less than 0.03 inches. According to some embodiments, the diameter of the wire comprising the half loops 230 is less than 0.02 inches. According to some embodiments, the diameter of the wire comprising the half loops 230 is less than 0.01 inches. According to some embodiments, the diameter of the wire comprising the half loops 230 is less than 0.009 inches. According to some embodiments, the diameter of the wire comprising the half loops 230 is less than 0.008 inches. According to some embodiments, the diameter of the wire comprising the half loops 230 is less than 0.007 inches. According to some embodiments, the diameter of the wire comprising the half loops 230 is less than 0.006 inches. According to some embodiments, the diameter of the wire comprising the half loops 230 is less than 0.005 inches. According to some embodiments, the diameter of the wire comprising the half loops 230 is less than 0.004 inches. According to some embodiments, the diameter of the wire comprising the half loops 230 is less than 0.003 inches. According to some embodiments, the diameter of the wire comprising the half loops 230 is less than 0.002 inches. According to some embodiments, the diameter of the wire comprising the half loops 230 is less than 0.001 inches.

According to some embodiments, one or more half loop 230 is connected to the central wire 250 around the circumference of the central wire 250. According to some embodiments, the circumference of the central wire comprises half loops 230 placed every 10 degrees of rotation around the central wire 250. According to some embodiments the circumference of the central wire comprises half loops 230 placed every 20 degrees of rotation around the central wire 250. According to some embodiments the circumference of the central wire 250 comprises half loops 230 placed every 30 degrees of rotation around the central wire 250. According to some embodiments the circumference of the central wire 250 comprises half loops 230 placed every 40 degrees of rotation around the central wire 250. According to some embodiments the circumference of the central wire 250 comprises half loops 230 placed every 50 degrees of rotation around the central wire 250. According to some embodiments the circumference of the central wire 250 comprises half loops 230 placed every 60 degrees of rotation around the central wire 250. According to some embodiments the circumference of the central wire 250 comprises half loops 230 placed every 70 degrees of rotation around the central wire 250. According to some embodiments the circumference of the central wire 250 comprises half loops 230 placed every 80 degrees of rotation around the central wire 250. According to some embodiments the circumference of the central wire 250 comprises half loops 230 placed every 90 degrees of rotation around the central wire 250. According to some embodiments the circumference of the central wire 250 comprises half loops 230 placed every 100 degrees of rotation around the central wire 250. According to some embodiments the circumference of the central wire 250 comprises half loops 230 placed every 110 degrees of rotation around the central wire 250. According to some embodiments the circumference of the central wire 250 comprises half loops 230 placed every 120 degrees of rotation around the central wire 250. According to some embodiments the circumference of the central wire 250 comprises half loops 230 placed every 130 degrees of rotation around the central wire 250. According to some embodiments the circumference of the central wire 250 comprises half loops 230 placed every 140 degrees of rotation around the central wire 250. According to some embodiments the circumference of the central wire 250 comprises half loops 230 placed every 150 degrees of rotation around the central wire 250. According to some embodiments the circumference of the central wire 250 comprises half loops 230 placed every 160 degrees of rotation around the central wire 250. According to some embodiments the circumference of the central wire 250 comprises half loops 230 placed every 170 degrees of rotation around the central wire 250. According to some embodiments the circumference of the central wire 250 comprises half loops 230 placed every 180 degrees of rotation around the central wire 250. According to some embodiments the circumference of the central wire 250 comprises half loops 230 placed every 190 degrees of rotation around the central wire 250. According to some embodiments the circumference of the central wire 250 comprises half loops 230 placed every 200 degrees of rotation around the central wire 250. According to some embodiments the circumference of the central wire 250 comprises half loops 230 placed every 210 degrees of rotation around the central wire 250. According to some embodiments the circumference of the central wire 250 comprises half loops 230 placed every 220 degrees of rotation around the central wire 250. According to some embodiments the circumference of the central wire 250 comprises half loops 230 placed every 230 degrees of rotation around the central wire 250. According to some embodiments the circumference of the central wire 250 comprises half loops 230 placed every 240 degrees of rotation around the central wire 250. According to some embodiments the circumference of the central wire 250 comprises half loops 230 placed every 250 degrees of rotation around the central wire 250. According to some embodiments the circumference of the central wire 250 comprises half-loops 230 placed every 260 degrees of rotation around the central wire 250. According to some embodiments the circumference of the central wire 250 comprises half loops 230 placed every 270 degrees of rotation around the central wire 250. According to some embodiments the circumference of the central wire 250 comprises half loops 230 placed every 280 degrees of rotation around the central wire 250. According to some embodiments the circumference of the central wire 250 comprises half loops 230 placed every 290 degrees of rotation around the central wire 250. According to some embodiments the circumference of the central wire 250 comprises half loops 230 placed every 300 degrees of rotation around the central wire 250. According to some embodiments the circumference of the central wire 250 comprises half loops 230 placed every 310 degrees of rotation around the central wire 250. According to some embodiments the circumference of the central wire 250 comprises half loops 230 placed every 320 degrees of rotation around the central wire 250. According to some embodiments the circumference of the central wire 250 comprises half loops 230 placed every 330 degrees of rotation around the central wire 250. According to some embodiments the circumference of the central wire 250 comprises half loops 230 placed every 340 degrees of rotation around the central wire 250. According to some embodiments the circumference of the central wire 250 comprises half loops 230 placed every 350 degrees of rotation around the central wire 250. According to some embodiments the circumference of the central wire 250 comprises half loops 230 placed every 360 degrees of rotation around the central wire 250.

According to some embodiments, the half loops 230 are staggered so that each half loop at least partially overlaps with at least one other half loop 230. For example, as depicted in FIG. 4 the half loops are positioned around the circumference of the central wire 250 every 180 degrees and are staggered so that each half loop 230 overlaps with both the preceding and the following half loop 230. In the non-limiting embodiment depicted in FIG. 4, about 33% of a preceding half loop 230 overlaps with a following half loop 230. According to some embodiments, the half loops 230 are staggered around the circumference of the central wire so that less than 10% of a preceding half loop 230 overlaps with a following half loop 230. According to some embodiments, the half loops 230 are staggered around the circumference of the central wire so that less than 15% of a preceding half loop 230 overlaps with a following half loop 230. According to some embodiments, the half loops 230 are staggered around the circumference of the central wire so that less than 20% of a preceding half loop 230 overlaps with a following half loop 230. According to some embodiments, the half loops 230 are staggered around the circumference of the central wire so that less than 25% of a preceding half loop 230 overlaps with a following half loop 230. According to some embodiments, the half loops 230 are staggered around the circumference of the central wire so that less than 30% of a preceding half loop 230 overlaps with a following half loop 230. According to some embodiments, the half loops 230 are staggered around the circumference of the central wire so that less than 35% of a preceding half loop 230 overlaps with a following half loop 230. According to some embodiments, the half loops 230 are staggered around the circumference of the central wire so that less than 40% of a preceding half loop 230 overlaps with a following half loop 230. According to some embodiments, the half loops 230 are staggered around the circumference of the central wire so that less than 45% of a preceding half loop 230 overlaps with a following half loop 230. According to some embodiments, the half loops 230 are staggered around the circumference of the central wire so that less than 50% of a preceding half loop 230 overlaps with a following half loop 230. According to some embodiments, the half loops 230 are staggered around the circumference of the central wire so that less than 55% of a preceding half loop 230 overlaps with a following half loop 230. According to some embodiments, the half loops 230 are staggered around the circumference of the central wire so that less than 60% of a preceding half loop 230 overlaps with a following half loop 230. According to some embodiments, the half loops 230 are staggered around the circumference of the central wire so that less than 65% of a preceding half loop 230 overlaps with a following half loop 230. According to some embodiments, the half loops 230 are staggered around the circumference of the central wire so that less than 70% of a preceding half loop 230 overlaps with a following half loop 230. According to some embodiments, the half loops 230 are staggered around the circumference of the central wire so that less than 75% of a preceding half loop 230 overlaps with a following half loop 230. According to some embodiments, the half loops 230 are staggered around the circumference of the central wire so that less than 80% of a preceding half loop 230 overlaps with a following half loop 230. According to some embodiments, the half loops 230 are staggered around the circumference of the central wire so that less than 85% of a preceding half loop 230 overlaps with a following half loop 230. According to some embodiments, the half loops 230 are staggered around the circumference of the central wire so that less than 90% of a preceding half loop 230 overlaps with a following half loop 230. According to some embodiments, the half loops 230 are staggered around the circumference of the central wire so that less than 95% of a preceding half loop 230 overlaps with a following half loop 230. According to some embodiments, the half loops 230 are staggered around the circumference of the central wire so that less than 100% of a preceding half loop 230 overlaps with a following half loop 230.

According to some embodiments, the half loops can be staggered around the circumference of the central wire 250 so that a preceding half loop does not overlap with a following half loop.

According to some embodiments, the half loop 230 comprises cross struts 240 that are connected to the central wire 250 at a 90-degree angle relative to the central wire. According to some embodiments, the cross struts 240 are connected to the central wire at less than a 90-degree angle. According to some embodiments, the cross struts 240 are connected to the central wire at less than an 85-degree angle. According to some embodiments, the cross struts 240 are connected to the central wire at less than an 80-degree angle. According to some embodiments, the cross struts 240 are connected to the central wire at less than a 75-degree angle. According to some embodiments, the cross struts 240 are connected to the central wire at less than a 70-degree angle. According to some embodiments, the cross struts 240 are connected to the central wire at less than a 65-degree angle. According to some embodiments, the cross struts 240 are connected to the central wire at less than a 60-degree angle. According to some embodiments, the cross struts 240 are connected to the central wire at less than a 55-degree angle. According to some embodiments, the cross struts 240 are connected to the central wire at less than a 50-degree angle. According to some embodiments, the cross struts 240 are connected to the central wire at less than a 45-degree angle. According to some embodiments, the cross struts 240 are connected to the central wire at less than a 40-degree angle. According to some embodiments, the cross struts 240 are connected to the central wire at less than a 35-degree angle. According to some embodiments, the cross struts 240 are connected to the central wire at less than a 30-degree angle. According to some embodiments, the cross struts 240 are connected to the central wire at less than a 25-degree angle. According to some embodiments, the cross struts 240 are connected to the central wire at less than a 20-degree angle. According to some embodiments, the cross struts 240 are connected to the central wire at less than a 15-degree angle. According to some embodiments, the cross struts 240 are connected to the central wire at less than a 10-degree angle. According to some embodiments, the cross struts 240 are connected to the central wire at less than a 5-degree angle.

According to some embodiments, the half loop structures 230 are made of a flexible material that is less stiff than the central wire 250. According to some embodiments, the half loop structures 230 comprise a flexible and resilient material that allows the half loop 230 to bend and spring back to its original shape.

According to some embodiments, the microwire 200 is effective to macerate a thrombus by contacting the thrombus with the distal end 220 of the microwire 200. According to some embodiments, the microwire 200 is effective to macerate a thrombus by rotating the half loops 230 while in contact with the thrombus. According to some embodiments, the microwire 200 can be used in conjunction with an aspirator to remove a thrombus.

The embodiment shown in FIGS. 5A through 5D includes side holes for infusion or irrigation and macerating loops mounted on a hypotube that can rotate for the loops to macerate a clot.

FIG. 5A, which shows an exemplary and non-limiting example of one aspect of the endovascular device of the described invention, illustrates a side view of one embodiment of the macerating irrigation catheter 300 of the described invention, comprising a central tube 390 having a proximal end 310 and a distal end 320. According to some embodiments, the central tube 390 comprises side holes 330 located around the circumference of the distal end 320 of the central tube 390. According to some embodiments, the macerating irrigation microcatheter further comprises a front hole 340 located at the tip of the distal end 320 of the macerating irrigation microcatheter, and a rear hole 350 located at the tip of the proximal end 310 of the macerating irrigation microcatheter. The rear hole 350 is capable of receiving a fluid from outside a patient's body, and each of the side holes 330 and front hole 340 are capable of ejecting fluid out of the central tube 390 into the vasculature of a patient. In some embodiments the fluid can be sometimes injected into the proximal hole 350 using a power injector. In some embodiments there is a Luer Lock on the proximal end of the hypotube, at 350. In some embodiment there is a soft atraumatic wire extending beyond end hole 340, and attached to it, which can have a straight, curved, ball-tip, or other shape, to facilitate the ability to advance the device distally when desired.

According to some embodiments, variables include, without limitation, the number of side holes, the spacing of the side holes, the proximity of the side holes to the distal end, the length over which the side holes exist, the shape of the side holes, the diameter of the side holes, catheter wall thickness, and internal and outer diameter of the catheter.

According to some embodiments, the side holes of the macerating irrigation microcatheter 300 are evenly spaced around the circumference of the macerating irrigation microcatheter 300. According to some embodiments, the side holes 330 are randomly spaced around the circumference of the macerating irrigation microcatheter 300. According to some embodiments, the side holes 330 are spaced in a repeating pattern around the circumference of the macerating irrigation microcatheter 300.

According to some embodiments, the side holes 330 are located on the distal end of the central tube 390 of the macerating irrigation microcatheter 300 for a length of 0.5 to 60 cm. According to some embodiments, the side holes 330 are located on the last 1 cm of the distal end 320 of the central tube 390. According to some embodiments, the side holes 330 are located on the last 3 cm of the distal end 320 of the central tube 390. According to some embodiments, the side holes 330 are located on the last 5 cm of the distal end 320 of the central tube 390. According to some embodiments, the side holes 330 are located on the last 10 cm of the distal end 320 of the central tube 390. According to some embodiments, the side holes 330 are located on the last 15 cm of the distal end 320 of the central tube 390. According to some embodiments, the side holes 330 are located on the last 20 cm of the distal end 320 of the central tube 390. According to some embodiments, the side holes 330 are located on the last 25 cm of the distal end 320 of the central tube 390. According to some embodiments, the side holes 330 are located on the last 30 cm of the distal end 320 of the central tube 390. According to some embodiments, the side holes 330 are located on the last 35 cm of the distal end 320 of the central tube 390. According to some embodiments, the side holes 330 are located on the last 40 cm of the distal end 320 of the central tube 390. According to some embodiments, the side holes 330 are located on the last 45 cm of the distal end 320 of the central tube 390. According to some embodiments, the side holes 330 are located on the last 50 cm of the distal end 320 of the central tube 390. According to some embodiments, the side holes 330 are located on the last 55 cm of the distal end 320 of the central tube 390. According to some embodiments, the side holes 330 are located on the last 60 cm of the distal end 320 of the central tube 390.

Figure 9:
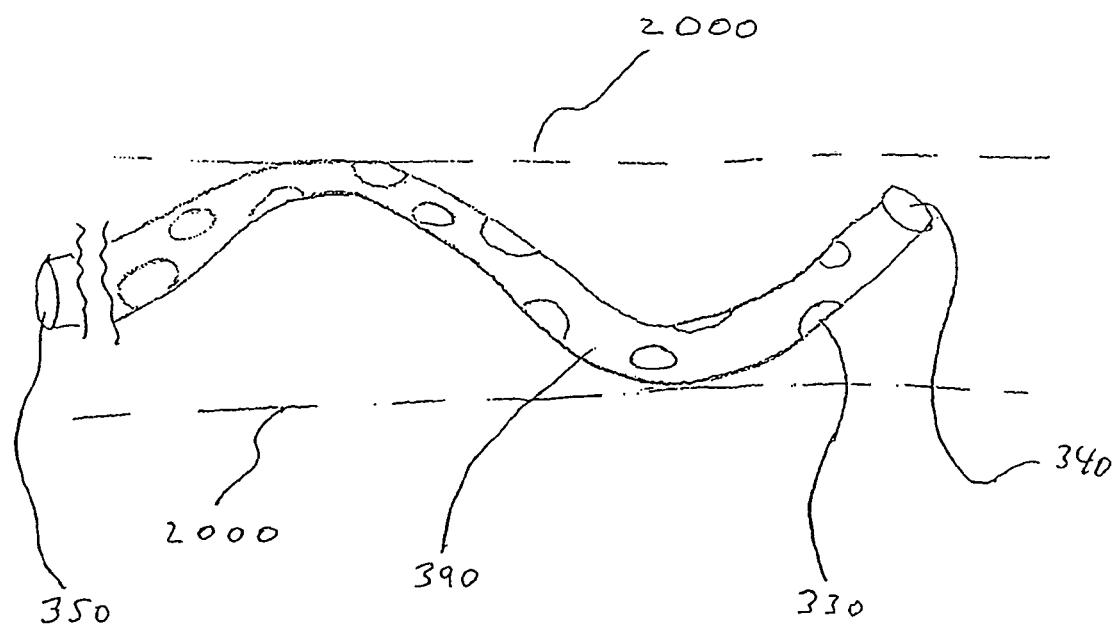
FIG. 9 illustrates a side view of the rotating, macerating and irrigating hypotube, including multiple irrigation side holes and end hole, of one embodiment of the described invention disposed within the lumen (cutaway) of a blood vessel.

With reference to FIG. 9, according to some embodiments the hypotube 390, also referred to as tube 390, itself has a sinusoidal or other geometric shape, so that the hypotube itself can effect maceration of the clot when it is rotated. This is a similar rotational maceration created by the Argon-Cleaner XT. But whereas their device only allows irrigation proximal to the clot, our device replaces the macerating sinusoidal cable with a hypotube, thereby allowing irrigation proximal to the clot, across the length of the clot, as well as distal to the clot. Our devices are further distinguished from The Argon device by additionally using aspiration, to prevent emboli and subsequent secondary ischemic injury to healthy downstream tissue, either immediately proximal to the clot with flow reversal techniques in most arterial application, or distal to the thrombectomy site in most venous applications. In many venous and some arterial applications, the protection from emboli afforded by the aspiration is further abetted by an attached semipermeable filter (FIGS. 7G, 10A, 11A, 12A, 13A).

According to some embodiments, the side holes 330 are of a circular shape. According to some embodiments, the side holes 330 are of an oval shape. According to some embodiments, the side holes 330 are of a square shape. According to some embodiments, the side holes 330 are of a rectangular shape. According to some embodiments, the side holes 330 are of a triangular shape. According to some embodiments, the side holes 330 are of a trapezoid shape. According to some embodiments, the side holes 330 are of a diamond shape. According to some embodiments, the side holes 330 are of a pentagon shape. According to some embodiments, the side holes 330 are of a hexagon shape. According to some embodiments, the side holes 330 are of a heptagon shape. According to some embodiments, the side holes 330 are of an octagon shape. According to some embodiments, the side holes 330 are of a nonagon shape. According to some embodiments, the side holes 330 are of a decagon shape. According to some embodiments, the side holes 330 are of an irregular shape. According to some embodiments, the side holes 330 are of a mixture of two or more of circular, oval, square, rectangle, triangle, diamond, pentagon, hexagon, heptagon, octagon, nonagon, decagon, and irregular shapes.

According to some embodiments, the size of the side holes 330 is greater than the size of the front hole 340. According to some embodiments, the size of the side holes 330 is less than the size of the front hole 340. According to some embodiments, the size of the side holes 330 is approximately the same size as the front hole 340.

According to some embodiments, the outer diameter of the central tube 390 of the macerating irrigation microcatheter 300 is between 34 French and 0.1 French. According to some embodiments, the outer diameter of the central tube 390 of the macerating irrigation microcatheter 300 is less than 34 French. According to some embodiments, the outer diameter of the central tube 390 of the macerating irrigation microcatheter 300 is less than 32 French. According to some embodiments, the outer diameter of the central tube 390 of the macerating irrigation microcatheter 300 is less than 30 French. According to some embodiments, the outer diameter of the central tube 390 of the macerating irrigation microcatheter 300 is less than 28 French. According to some embodiments, the outer diameter of the central tube 390 of the macerating irrigation microcatheter 300 is less than 26 French. According to some embodiments, the outer diameter of the central tube 390 of the macerating irrigation microcatheter 300 is less than 24 French. According to some embodiments, the outer diameter of the central tube 390 of the macerating irrigation microcatheter 300 is less than 22 French. According to some embodiments, the outer diameter of the central tube 390 of the macerating irrigation microcatheter 300 is less than 20 French. According to some embodiments, the outer diameter of the central tube 390 of the macerating irrigation microcatheter 300 is less than 19 French. According to some embodiments, the outer diameter of the central tube 390 of the macerating irrigation microcatheter 300 is less than 18 French. According to some embodiments, the outer diameter of the central tube 390 of the macerating irrigation microcatheter 300 is less than 17 French. According to some embodiments, the outer diameter of the central tube 390 of the macerating irrigation microcatheter 300 is less than 16 French. According to some embodiments, the outer diameter of the central tube 390 of the macerating irrigation microcatheter 300 is less than 15 French. According to some embodiments, the outer diameter of the central tube 390 of the macerating irrigation microcatheter 300 is less than 14 French. According to some embodiments, the outer diameter of the central tube 390 of the macerating irrigation microcatheter 300 is less than 13 French. According to some embodiments, the outer diameter of the central tube 390 of the macerating irrigation microcatheter 300 is less than 12 French. According to some embodiments, the outer diameter of the central tube 390 of the macerating irrigation microcatheter 300 is less than 11 French. According to some embodiments, the outer diameter of the central tube 390 of the macerating irrigation microcatheter 300 is less than 10 French. According to some embodiments, the outer diameter of the central tube 390 of the macerating irrigation microcatheter 300 is less than 9 French. According to some embodiments, the outer diameter of the central tube 390 of the macerating irrigation microcatheter 300 is less than 8 French. According to some embodiments, the outer diameter of the central tube 390 of the macerating irrigation microcatheter 300 is less than 7 French. According to some embodiments, the outer diameter of the central tube 390 of the macerating irrigation microcatheter 300 is less than 6 French. According to some embodiments, the outer diameter of the central tube 390 of the macerating irrigation microcatheter 300 is less than 5 French. According to some embodiments, the outer diameter of the central tube 390 of the macerating irrigation microcatheter 300 is less than 4 French. According to some embodiments, the outer diameter of the central tube 390 of the macerating irrigation microcatheter 300 is less than 3 French. According to some embodiments, the outer diameter of the central tube 390 of the macerating irrigation microcatheter 300 is less than 2 French. According to some embodiments, the outer diameter of the central tube 390 of the macerating irrigation microcatheter 300 is less than 1 French.

According to some embodiments, the width of the side holes 330 at their widest point is between 17 French and 0.01 French. According to some embodiments, the width of side holes 330 at their widest point is less than 17 French. According to some embodiments, the width of side holes 330 at their widest point is less than 16 French. According to some embodiments, the width of side holes 330 at their widest point is less than 15 French. According to some embodiments, the width of side holes 330 at their widest point is less than 14 French. According to some embodiments, the width of side holes 330 at their widest point is less than 13 French. According to some embodiments, the width of side holes 330 at their widest point is less than 12 French. According to some embodiments, the width of side holes 330 at their widest point is less than 11 French. According to some embodiments, the width of side holes 330 at their widest point is less than 10 French. According to some embodiments, the width of side holes 330 at their widest point is less than 9 French. According to some embodiments, the width of side holes 330 at their widest point is less than 8 French. According to some embodiments, the width of side holes 330 at their widest point is less than 7 French. According to some embodiments, the width of side holes 330 at their widest point is less than 6 French. According to some embodiments, the width of side holes 330 at their widest point is less than 5 French. According to some embodiments, the width of side holes 330 at their widest point is less than 4 French. According to some embodiments, the width of side holes 330 at their widest point is less than 3 French. According to some embodiments, the width of side holes 330 at their widest point is less than 2 French. According to some embodiments, the width of side holes 330 at their widest point is less than 1 French. According to some embodiments, the width of side holes 330 at their widest point is less than 0.1 French. According to some embodiments, the width of side holes 330 at their widest point is less than 0.01 French.

According to some embodiments, the diameter of the luminal space defined by the central tube 390 of the macerating irrigation microcatheter 300 is between 32 French and 0.1 French. According to some embodiments, the diameter of the luminal space defined by the central tube 390 of the macerating irrigation microcatheter 300 is less than 32 French. According to some embodiments, the diameter of the luminal space defined by the central tube 390 of the macerating irrigation microcatheter 300 is less than 30 French. According to some embodiments, the diameter of the luminal space defined by the central tube 390 of the macerating irrigation microcatheter 300 is less than 28 French. According to some embodiments, the diameter of the luminal space defined by the central tube 390 of the macerating irrigation microcatheter 300 is less than 26 French. According to some embodiments, the diameter of the luminal space defined by the central tube 390 of the macerating irrigation microcatheter 300 is less than 24 French. According to some embodiments, the diameter of the luminal space defined by the central tube 390 of the macerating irrigation microcatheter 300 is less than 22 French. According to some embodiments, the diameter of the luminal space defined by the central tube 390 of the macerating irrigation microcatheter 300 is less than 20 French. According to some embodiments, the diameter of the luminal space defined by the central tube 390 of the macerating irrigation microcatheter 300 is less than 19 French. According to some embodiments, the diameter of the luminal space defined by the central tube 390 of the macerating irrigation microcatheter 300 is less than 18 French. According to some embodiments, the diameter of the luminal space defined by the central tube 390 of the macerating irrigation microcatheter 300 is less than 17 French. According to some embodiments, the diameter of the luminal space defined by the central tube 390 of the macerating irrigation microcatheter 300 is less than 16 French. According to some embodiments, the diameter of the luminal space defined by the central tube 390 of the macerating irrigation microcatheter 300 is less than 15 French. According to some embodiments, the diameter of the luminal space defined by the central tube 390 of the macerating irrigation microcatheter 300 is less than 14 French. According to some embodiments, the diameter of the luminal space defined by the central tube 390 of the macerating irrigation microcatheter 300 is less than 13 French. According to some embodiments, the diameter of the luminal space defined by the central tube 390 of the macerating irrigation microcatheter 300 is less than 12 French. According to some embodiments, the diameter of the luminal space defined by the central tube 390 of the macerating irrigation microcatheter 300 is less than 11 French. According to some embodiments, the diameter of the luminal space defined by the central tube 390 of the macerating irrigation microcatheter 300 is less than 10 French. According to some embodiments, the diameter of the luminal space defined by the central tube 390 of the macerating irrigation microcatheter 300 is less than 9 French. According to some embodiments, the diameter of the luminal space defined by the central tube 390 of the macerating irrigation microcatheter 300 is less than 8 French. According to some embodiments, the diameter of the luminal space defined by the central tube 390 of the macerating irrigation microcatheter 300 is less than 7 French. According to some embodiments, the diameter of the luminal space defined by the central tube 390 of the macerating irrigation microcatheter 300 is less than 6 French. According to some embodiments, the diameter of the luminal space defined by the central tube 390 of the macerating irrigation microcatheter 300 is less than 5 French. According to some embodiments, the diameter of the luminal space defined by the central tube 390 of the macerating irrigation microcatheter 300 is less than 4 French. According to some embodiments, the diameter of the luminal space defined by the central tube 390 of the macerating irrigation microcatheter 300 is less than 3 French. According to some embodiments, the diameter of the luminal space defined by the central tube 390 of the macerating irrigation microcatheter 300 is less than 2 French. According to some embodiments, the diameter of the luminal space defined by the central tube 390 of the macerating irrigation microcatheter 300 is less than 1 French. According to some embodiments, the diameter of the luminal space defined by the central tube 390 of the macerating irrigation microcatheter 300 is less than 0.1 French. According to some embodiments, the diameter of the luminal space defined by the central tube 390 of the macerating irrigation microcatheter 300 is less than 0.01 French.

According to some embodiments, the central tube 390 of the macerating irrigation microcatheter 300 is made from one or more of the following materials: silicone, polyurethane, polyethylene, polytetrafluoroethylene (PTFE), polyethylene terephthalate (PET), latex, and thermoplastic elastomers. According to some embodiments, the central tube 390 of the macerating irrigation microcatheter 300 comprises an inner layer made of a first material, and an outer layer made from a second material. According to some embodiments, the central tube 390 of the macerating irrigation microcatheter 300 is reinforced with steel or other suitable material.

According to some embodiments, the central tube 390 of the macerating irrigation microcatheter 300 is made of a material and of dimensions able to withstand internal pressure between 0.1 and 1200 psi. According to some embodiments, the central tube 390 is able to withstand internal pressures greater than 0.1 psi. According to some embodiments, the central tube 390 is able to withstand internal pressures greater than 1 psi. According to some embodiments, the central tube 390 is able to withstand internal pressures greater than 5 psi. According to some embodiments, the central tube 390 is able to withstand internal pressures greater than 10 psi. According to some embodiments, the central tube 390 is able to withstand internal pressures greater than 15 psi. According to some embodiments, the central tube 390 is able to withstand internal pressures greater than 20 psi. According to some embodiments, the central tube 390 is able to withstand internal pressures greater than 40 psi. According to some embodiments, the central tube 390 is able to withstand internal pressures greater than 80 psi. According to some embodiments, the central tube 390 is able to withstand internal pressures greater than 160 psi. According to some embodiments, the central tube 390 is able to withstand internal pressures greater than 320 psi. According to some embodiments, the central tube 390 is able to withstand internal pressures greater than 460 psi. According to some embodiments, the central tube 390 is able to withstand internal pressures greater than 920 psi. According to some embodiments, the central tube 390 is able to withstand internal pressures greater than 1000 psi. According to some embodiments, the central tube 390 is able to withstand internal pressures greater than 1200 psi.

According to some embodiments, the outer diameter of the central tube 390 at the proximal end 310 is approximately the same as the outer diameter of the central tube 390 at the distal end 320. According to some embodiments, the outer diameter of the central tube 390 at the proximal end 310 is greater than the outer diameter of the central tube 390 at the distal end 320. According to some embodiments, the outer diameter of the central tube 390 at the proximal end 310 is less than the outer diameter of the central tube 390 at the distal end 320. According to some embodiments, the outer diameter of the central tube 390 varies along its length.

According to some embodiments, the inner luminal diameter of the central tube 390 at the proximal end 310 is approximately the same as the inner luminal diameter of the central tube 390 at the distal end 320. According to some embodiments, the inner luminal diameter of the central tube 390 at the proximal end 310 is greater than the inner luminal diameter of the central tube 390 at the distal end 320. According to some embodiments, the inner luminal diameter of the central tube 390 at the proximal end 310 is less than the inner luminal diameter of the central tube 390 at the distal end 320. According to some embodiments, the inner luminal diameter of the central tube 390 varies along its length.

According to some embodiments, the macerating irrigation microcatheter 300 further comprises one or more half loop structures 360. As illustrated in FIG. 5A, according to some embodiments, one or more half loop structures 360 are attached to the distal end 320 of the central tube 390. According to some embodiments, the half loop structures 360 comprise a microwire 370 comprising a first end and a second end, wherein both the first end and the second end are connected to the outside of the central tube 390. According to some embodiments, the half loop structures 360 comprise cross strut wires 380 connected to both the microwire 370 and the central tube 390. Said cross-strut wires 380 may vary in size but are limited by the maximum interior radius of the vessel.

According to some embodiments, variables include, without limitation, the diameter of the microwire, size of the half loops, placement of the macerating half loops, and construction of the macerating half loops.

According to some embodiments, the proximal end 310 of the central tube 390 can be connected to a power-driven plug that rotates the macerating irrigation microcatheter 300 around its central axis. According to some such embodiments, the power-driven plug may be battery or electrically powered.

According to some embodiments, the half loops 360 are comprised of wire of a diameter between 0.1 inches and 0.006 inches. According to some embodiments, the half loops 360 are comprised of wire of a diameter of less than 0.1 inches. According to some embodiments, the half loops 360 are comprised of wire of a diameter of less than 0.05 inches. According to some embodiments, the half loops 360 are comprised of wire of a diameter of less than 0.04 inches. According to some embodiments, the half loops 360 are comprised of wire of a diameter of less than 0.03 inches. According to some embodiments, the half loops 360 are comprised of wire of a diameter of less than 0.02 inches. According to some embodiments, the half loops 360 are comprised of wire of a diameter of less than 0.01 inches. According to some embodiments, the half loops 360 are comprised of wire of a diameter of less than 0.009 inches. According to some embodiments, the half loops 360 are comprised of wire of a diameter of less than 0.008 inches. According to some embodiments, the half loops 360 are comprised of wire of a diameter of less than 0.007 inches. According to some embodiments, the half loops 360 are comprised of wire of a diameter of less than 0.006 inches. According to some embodiments, the half loops 360 are comprised of wire of a diameter of less than 0.005 inches. According to some embodiments, the half loops 360 are comprised of wire of a diameter of less than 0.004 inches. According to some embodiments, the half loops 360 are comprised of wire of a diameter of less than 0.003 inches. According to some embodiments, the half loops 360 are comprised of wire of a diameter of less than 0.002 inches. According to some embodiments, the half loops 360 are comprised of wire of a diameter of less than 0.001 inches.

According to some embodiments, a plurality of half loops 360 is connected around the circumference of the central tube 390. According to some embodiments, the half loops 360 are located on the central tube 390 every 10 degrees of rotation around the central tube 390. According to some embodiments, the half loops 360 are located on the central tube 390 every 20 degrees of rotation around the central tube 390. According to some embodiments, the half loops 360 are located on the central tube 390 every 30 degrees of rotation around the central tube 390. According to some embodiments, the half loops 360 are located on the central tube 390 every 40 degrees of rotation around the central tube 390. According to some embodiments, the half loops 360 are located on the central tube 390 every 50 degrees of rotation around the central tube 390. According to some embodiments, the half loops 360 are located on the central tube 390 every 60 degrees of rotation around the central tube 390. According to some embodiments, the half loops 360 are located on the central tube 390 every 70 degrees of rotation around the central tube 390. According to some embodiments, the half loops 360 are located on the central tube 390 every 80 degrees of rotation around the central tube 390. According to some embodiments, the half loops 360 are located on the central tube 390 every 90 degrees of rotation around the central tube 390. According to some embodiments, the half loops 360 are located on the central tube 390 every 100 degrees of rotation around the central tube 390. According to some embodiments, the half loops 360 are located on the central tube 390 every 120 degrees of rotation around the central tube 390. According to some embodiments, the half loops 360 are located on the central tube 390 every 130 degrees of rotation around the central tube 390. According to some embodiments, the half loops 360 are located on the central tube 390 every 140 degrees of rotation around the central tube 390. According to some embodiments, the half loops 360 are located on the central tube 390 every 150 degrees of rotation around the central tube 390. According to some embodiments, the half loops 360 are located on the central tube 390 every 160 degrees of rotation around the central tube 390. According to some embodiments, the half loops 360 are located on the central tube 390 every 170 degrees of rotation around the central tube 390. According to some embodiments, the half loops 360 are located on the central tube 390 every 180 degrees of rotation around the central tube 390. According to some embodiments, the half loops 360 are located on the central tube 390 every 190 degrees of rotation around the central tube 390. According to some embodiments, the half loops 360 are located on the central tube 390 every 200 degrees of rotation around the central tube 390. According to some embodiments, the half loops 360 are located on the central tube 390 every 210 degrees of rotation around the central tube 390. According to some embodiments, the half loops 360 are located on the central tube 390 every 220 degrees of rotation around the central tube 390. According to some embodiments, the half loops 360 are located on the central tube 390 every 230 degrees of rotation around the central tube 390. According to some embodiments, the half loops 360 are located on the central tube 390 every 240 degrees of rotation around the central tube 390. According to some embodiments, the half loops 360 are located on the central tube 390 every 250 degrees of rotation around the central tube 390. According to some embodiments, the half loops 360 are located on the central tube 390 every 260 degrees of rotation around the central tube 390. According to some embodiments, the half loops 360 are located on the central tube 390 every 270 degrees of rotation around the central tube 390.

According to some embodiments, the half loops 360 are located on the central tube 390 every 280 degrees of rotation around the central tube 390. According to some embodiments, the half loops 360 are located on the central tube 390 every 290 degrees of rotation around the central tube 390. According to some embodiments, the half loops 360 are located on the central tube 390 every 300 degrees of rotation around the central tube 390. According to some embodiments, the half loops 360 are located on the central tube 390 every 310 degrees of rotation around the central tube 390. According to some embodiments, the half loops 360 are located on the central tube 390 every 320 degrees of rotation around the central tube 390. According to some embodiments, the half loops 360 are located on the central tube 390 every 330 degrees of rotation around the central tube 390. According to some embodiments, the half loops 360 are located on the central tube 390 every 340 degrees of rotation around the central tube 390. According to some embodiments, the half loops 360 are located on the central tube 390 every 350 degrees of rotation around the central tube 390. According to some embodiments, the half loops 360 are located on the central tube 390 every 360 degrees of rotation around the central tube 390.

According to some embodiments, the half loops 360 are staggered so that each half loop at least partially overlaps with at least one other half loop 360. For example, as depicted in FIG. 5A the half loops are positioned around the circumference of the central tube 390 every 180 degrees and are staggered so that each half loop 360 overlaps with the preceding and following half loop 360. In the embodiment depicted in FIG. 5A, about 33% of a preceding half loop 360 overlaps with a following half loop 360. According to some embodiments, the half loops 360 are staggered around the circumference of the central tube 390 so that less than 10% of a preceding half loop 360 overlaps with a following half loop 360. According to some embodiments, the half loops 360 are staggered around the circumference of the central tube 390 so that less than 15% of a preceding half loop 360 overlaps with a following half loop 360. According to some embodiments, the half loops 360 are staggered around the circumference of the central tube 390 so that less than 20% of a preceding half loop 360 overlaps with a following half loop 360. According to some embodiments, the half loops 360 are staggered around the circumference of the central tube 390 so that less than 25% of a preceding half loop 360 overlaps with a following half loop 360. According to some embodiments, the half loops 360 are staggered around the circumference of the central tube 390 so that less than 30% of a preceding half loop 360 overlaps with a following half loop 360. According to some embodiments, the half loops 360 are staggered around the circumference of the central tube 390 so that less than 35% of a preceding half loop 360 overlaps with a following half loop 360. According to some embodiments, the half loops 360 are staggered around the circumference of the central tube 390 so that less than 40% of a preceding half loop 360 overlaps with a following half loop 360. According to some embodiments, the half loops 360 are staggered around the circumference of the central tube 390 so that less than 45% of a preceding half loop 360 overlaps with a following half loop 360. According to some embodiments, the half loops 360 are staggered around the circumference of the central tube 390 so that less than 50% of a preceding half loop 360 overlaps with a following half loop 360. According to some embodiments, the half loops 360 are staggered around the circumference of the central tube 390 so that less than 60% of a preceding half loop 360 overlaps with a following half loop 360. According to some embodiments, the half loops 360 are staggered around the circumference of the central tube 390 so that less than 65% of a preceding half loop 360 overlaps with a following half loop 360. According to some embodiments, the half loops 360 are staggered around the circumference of the central tube 390 so that less than 70% of a preceding half loop 360 overlaps with a following half loop 360. According to some embodiments, the half loops 360 are staggered around the circumference of the central tube 390 so that less than 75% of a preceding half loop 360 overlaps with a following half loop 360. According to some embodiments, the half loops 360 are staggered around the circumference of the central tube 390 so that less than 80% of a preceding half loop 360 overlaps with a following half loop 360. According to some embodiments, the half loops 360 are staggered around the circumference of the central tube 390 so that less than 85% of a preceding half loop 360 overlaps with a following half loop 360. According to some embodiments, the half loops 360 are staggered around the circumference of the central tube 390 so that less than 90% of a preceding half loop 360 overlaps with a following half loop 360. According to some embodiments, the half loops 360 are staggered around the circumference of the central tube 390 so that less than 95% of a preceding half loop 360 overlaps with a following half loop 360. According to some embodiments, the half loops 360 are staggered around the circumference of the central tube 390 so that less than 100% of a preceding half loop 360 overlaps with a following half loop 360.

According to some embodiments, the half loops 360 may be staggered around the circumference of the central tube 390 so that a preceding half loop does not overlap with a following half loop 360.

According to some embodiments, the half loop 360 comprises cross strut wires 380 that are connected to the central tube 390 at a 90-degree angle relative to the central tube 390. According to some embodiments, the cross-strut wires 380 are connected to the central tube 390 at less than a 90-degree angle. According to some embodiments, the cross-strut wires 380 are connected to the central tube 390 at less than an 85-degree angle. According to some embodiments, the cross-strut wires 380 are connected to the central tube 390 at less than an 80-degree angle. According to some embodiments, the cross-strut wires 380 are connected to the central tube 390 at less than a 75-degree angle. According to some embodiments, the cross-strut wires 380 are connected to the central tube 390 at less than a 70-degree angle. According to some embodiments, the cross-strut wires 380 are connected to the central tube 390 at less than a 65-degree angle. According to some embodiments, the cross-strut wires 380 are connected to the central tube 390 at less than a 60-degree angle. According to some embodiments, the cross-strut wires 380 are connected to the central tube 390 at less than a 55-degree angle. According to some embodiments, the cross-strut wires 380 are connected to the central tube 390 at less than a 50-degree angle. According to some embodiments, the cross-strut wires 380 are connected to the central tube 390 at less than a 45-degree angle. According to some embodiments, the cross-strut wires 380 are connected to the central tube 390 at less than a 40-degree angle. According to some embodiments, the cross-strut wires 380 are connected to the central tube 390 at less than a 35-degree angle. According to some embodiments, the cross-strut wires 380 are connected to the central tube 390 at less than a 30-degree angle. According to some embodiments, the cross-strut wires 380 are connected to the central tube 390 at less than a 25-degree angle. According to some embodiments, the cross-strut wires 380 are connected to the central tube 390 at less than a 20-degree angle. According to some embodiments, the cross-strut wires 380 are connected to the central tube 390 at less than a 15-degree angle. According to some embodiments, the cross-strut wires 380 are connected to the central tube 390 at less than a 10-degree angle. According to some embodiments, the cross-strut wires 380 are connected to the central tube 390 at less than a 5-degree angle.

According to some embodiments, the half loop structures 360 comprise between 1 and 100 cross strut wires 380. According to some embodiments, the half loop structures 360 comprise 1 or more cross strut wires 380. According to some embodiments, the half loop structures 360 comprise 2 or more cross strut wires 380. According to some embodiments, the half loop structures 360 comprise 3 or more cross strut wires 380. According to some embodiments, the half loop structures 360 comprise 4 or more cross strut wires 380. According to some embodiments, the half loop structures 360 comprise 5 or more cross strut wires 380. According to some embodiments, the half loop structures 360 comprise 6 or more cross strut wires 380. According to some embodiments, the half loop structures 360 comprise 7 or more cross strut wires 380. According to some embodiments, the half loop structures 360 comprise 8 or more cross strut wires 380. According to some embodiments, the half loop structures 360 comprise 9 or more cross strut wires 380. According to some embodiments, the half loop structures 360 comprise 10 or more cross strut wires 380. According to some embodiments, the half loop structures 360 comprise 15 or more cross strut wires 380. According to some embodiments, the half loop structures 360 comprise 20 or more cross strut wires 380. According to some embodiments, the half loop structures 360 comprise 25 or more cross strut wires 380. According to some embodiments, the half loop structures 360 comprise 30 or more cross strut wires 380. According to some embodiments, the half loop structures 360 comprise 40 or more cross strut wires 380. According to some embodiments, the half loop structures 360 comprise 50 or more cross strut wires 380. According to some embodiments, the half loop structures 360 comprise 60 or more cross strut wires 380. According to some embodiments, the half loop structures 360 comprise 70 or more cross strut wires 380. According to some embodiments, the half loop structures 360 comprise 80 or more cross strut wires 380. According to some embodiments, the half loop structures 360 comprise 90 or more cross strut wires 380. According to some embodiments, the half loop structures 360 comprise 100 or more cross strut wires 380.

According to some embodiments, the half loop structures 360 on the macerating irrigation catheter 300 are positioned on the central tube 390 above or adjacent to one or more of the side holes 330. According to some embodiments, the half loop structures 360 positioned on the central tube 390 above or adjacent to a side hole 330 are effective to break up the clot into smaller pieces, thereby facilitating its removal via an aspirating catheter proximal or distal to the clot, while also minimizing the chance the aspirating catheter could become clogged by larger pieces of clot. According to some embodiments, the type and amount of breakdown of clots into smaller pieces can be altered depending upon the number and position of the microwire 370 and cross strut wires 380 in proximity to the side holes 330.

According to some embodiments, the microwire 370 spans at least a part of a side hole 330, and all concomitant cross strut wires 380 are on one side of the side hole 330. According to the embodiment illustrated in FIG. 5B, the microwire 370 spans the middle of the side hole 330, and each of cross strut wires 380 are connected to the surface of the central tube 390 on one side of the side hole 330.

According to some embodiments, the microwire 370 spans at least part of a side hole 330 and the concomitant cross strut wires are connected to either side of the side hole 330. According to the embodiment illustrated in FIG. 5C, the microwire 370 spans the middle of the side hole 330, and each of cross strut wires 380 are alternately connected to the central tube 390 on opposite sides of the side hole 330, or at various angles relative to the side holes.

According to some embodiments, the microwire 370 is connected to the central tube 390 such that the microwire 370 is adjacent to, but does not span, side holes 330. According to the embodiment illustrated in FIG. 5D, the microwire 370 is connected to the central tube 390 between two separate side holes 330. Cross strut wires 380 are also connected to the central tube 390 between two separate side holes 330.

According to some embodiments of the described invention, the length of the microwire 370 and the length of the cross-strut wires 380 determine the distance by which the half loop structures extend from the surface of the central tube 390. According to some embodiments, one or more of the half loop structures 360 extend from the surface of the central tube 390 by a length equivalent to one half the diameter of the central tube 390. According to some embodiments, one or more of the half loop structures 360 extend from the surface of the central tube 390 by a length equivalent to the diameter of the central tube 390. According to some embodiments, one or more of the half loop structures 360 extend from the surface of the central tube 390 by a length equivalent to double the diameter of the central tube 390. According to some embodiments, one or more of the half loop structures 360 extend from the surface of the central tube 390 by a length equivalent to triple the diameter of the central tube 390. According to some embodiments, one or more of the half loop structures 360 extend from the surface of the central tube 390 by a length equivalent to quadruple the diameter of the central tube 390. According to some embodiments, one or more of the half loop structures 360 extend from the surface of the central tube 390 by a length equivalent to five times the diameter of the central tube 390. According to some embodiments, one or more of the half loop structures 360 extend from the surface of the central tube 390 by a length equivalent to six times the diameter of the central tube 390. According to some embodiments, one or more of the half loop structures 360 extend from the surface of the central tube 390 by a length equivalent to less than one half the diameter of the central tube 390. According to some embodiments, one or more of the half loop structures 360 extend from the surface of the central tube 390 by a length equivalent to greater than six times the diameter of the central tube 390.

According to some embodiments, the microwire 370 takes a continuously curved path between the first end and the second end. According to some embodiments, the microwire 370 takes an irregularly shaped path between the first end and the second end. According to some embodiments, the microwire 370 takes a path comprising two or more straight paths connected at an angle between 0 degrees and 180 degrees.

According to some embodiments, the cross-strut wires 380 take a straight path from a first end connected to the central tube 390 and the second end connected to the microwire 370. According to some embodiments, the cross-strut wires 380 take a non-linear path from a first end connected to the central tube 390 and the second end connected to the microwire 370. According to some embodiments, cross strut wires 380 are branched such that one or more of the cross-strut wires 380 is connected to one or more other cross strut wires 380.

According to some embodiments, the half loop structures 360 are oriented linearly along the central tube 390; i.e. the first end of the microwire 370 and the second end of the microwire 370 are attached to the central tube 390 in a line parallel to the length of the central tube 390. According to some embodiments, the half loop structures 360 are oriented in a spiral around the central tube 390; i.e., the second end of the microwire 370 is located in a position on the surface of the central tube 390 that is radially twisted around the central tube 390 relative to the first end of the microwire 370. According to some embodiments, the second end of the microwire 370 is radially twisted relative to the first end of the microwire 370 by less than 5 degrees. According to some embodiments, the second end of the microwire 370 is radially twisted relative to the first end of the microwire 370 by less than 10 degrees. According to some embodiments, the second end of the microwire 370 is radially twisted relative to the first end of the microwire 370 by less than 15 degrees. According to some embodiments, the second end of the microwire 370 is radially twisted relative to the first end of the microwire 370 by less than 20 degrees. According to some embodiments, the second end of the microwire 370 is radially twisted relative to the first end of the microwire 370 by less than 25 degrees. According to some embodiments, the second end of the microwire 370 is radially twisted relative to the first end of the microwire 370 by less than 30 degrees. According to some embodiments, the second end of the microwire 370 is radially twisted relative to the first end of the microwire 370 by less than 35 degrees. According to some embodiments, the second end of the microwire 370 is radially twisted relative to the first end of the microwire 370 by less than 40 degrees. According to some embodiments, the second end of the microwire 370 is radially twisted relative to the first end of the microwire 370 by less than 45 degrees. According to some embodiments, the second end of the microwire 370 is radially twisted relative to the first end of the microwire 370 by less than 50 degrees. According to some embodiments, the second end of the microwire 370 is radially twisted relative to the first end of the microwire 370 by less than 60 degrees. According to some embodiments, the second end of the microwire 370 is radially twisted relative to the first end of the microwire 370 by less than 65 degrees. According to some embodiments, the second end of the microwire 370 is radially twisted relative to the first end of the microwire 370 by less than 70 degrees. According to some embodiments, the second end of the microwire 370 is radially twisted relative to the first end of the microwire 370 by less than 75 degrees. According to some embodiments, the second end of the microwire 370 is radially twisted relative to the first end of the microwire 370 by less than 80 degrees. According to some embodiments, the second end of the microwire 370 is radially twisted relative to the first end of the microwire 370 by less than 85 degrees. According to some embodiments, the second end of the microwire 370 is radially twisted relative to the first end of the microwire 370 by less than 90 degrees. According to some embodiments, the second end of the microwire 370 is radially twisted relative to the first end of the microwire 370 by less than 180 degrees. According to some embodiments, the second end of the microwire 370 is radially twisted relative to the first end of the microwire 370 by less than 360 degrees. According to some embodiments, the second end of the microwire 370 is radially twisted relative to the first end of the microwire 370 by less than 720 degrees. According to some embodiments, the second end of the microwire 370 is radially twisted relative to the first end of the microwire 370 by less than 1080 degrees.

According to some embodiments, the macerating irrigation microcatheter 300 is adapted so that fluid passes through the catheter as it is macerating the clot, for example, in short intermittent infusions; for example, in a continuous infusion. According to some embodiments, the fluid flow is into and beyond the clot so that the clot is capable of being aspirated proximally.

According to some embodiments, the macerating irrigation catheter 300 further comprises a filter 395 that protrudes from the distal end of the central tube 390 to catch any macerated clot material that escapes aspiration. According to some embodiments, the filter 395 is connected to an intraluminal cable 396 which runs through the luminal space defined by the central tube 390 (FIG. 5A). According to some embodiments, the filter 395 comprises a net structure connected to the intraluminal cable 396, wherein the net structure is effective to capture distal emboli that may result from maceration of a blood clot proximal to the filter. According to some embodiments, the filter 395 is effective to capture particulates greater than 10 µm in size. According to some embodiments, the filter 395 is effective to capture particulates greater than 15 µm in size. According to some embodiments, the filter 395 is effective to capture particulates greater than 20 µm in size. According to some embodiments, the filter 395 is effective to capture particulates greater than 30 µm in size. According to some embodiments, the filter 395 is effective to capture particulates greater than 40 µm in size. According to some embodiments, the filter 395 is effective to capture particulates greater than 50 µm in size. According to some embodiments, the filter 395 is effective to capture particulates greater than 70 µm in size. According to some embodiments, the filter 395 is effective to capture particulates greater than 100 µm in size. According to some embodiments, the filter 395 is effective to capture particulates greater than 500 µm in size.

According to some embodiments, the filter 395 comprises an opening that is round in shape and comprises a diameter approximately equal to the diameter of the central tube 390. According to some embodiments, the filter 395 comprises an opening that comprises a diameter less than or equal to twice the diameter of the central tube 390. According to some embodiments, the filter 395 comprises an opening that comprises a diameter less than or equal to three times the diameter of the central tube 390. According to some embodiments, the filter 395 comprises an opening that comprises a diameter less than or equal to four times the diameter of the central tube 390. According to some embodiments, the filter 395 comprises an opening that comprises a diameter less than or equal to five times the diameter of the central tube 390. According to some embodiments, the filter 395 comprises an opening that comprises a diameter less than or equal to six times the diameter of the central tube 390. According to some embodiments, the filter 395 comprises an opening that comprises a diameter less than or equal to seven times the diameter of the central tube 390. According to some embodiments, the filter 395 comprises an opening that comprises a diameter less than or equal to eight times the diameter of the central tube 390. According to some embodiments, the filter 395 comprises an opening that comprises a diameter less than or equal to nine times the diameter of the central tube 390. According to some embodiments, the filter 395 comprises an opening that comprises a diameter less than or equal to ten times the diameter of the central tube 390.

According to some embodiments, diameter of the filter 395 diameter is between 0.1 cm and 15 cm. According to some embodiments, diameter of the filter 395 diameter is less than or equal to 15 cm. According to some embodiments, diameter of the filter 395 diameter is less than or equal to 10 cm. According to some embodiments, diameter of the filter 395 is less than or equal to 7 cm. According to some embodiments, diameter of the filter 395 is less than or equal to 5 cm. According to some embodiments, diameter of the filter 395 is less than or equal to 3 cm. According to some embodiments, diameter of the filter 395 is less than or equal to 1 cm. According to some embodiments, diameter of the filter 395 is less than or equal to 0.5 cm.

According to some embodiments the filter 395 is made from a flexible, but resilient material that can be folded and contained inside the lumen defined by central tube 390.

FIG. 6 shows an embodiment of the aspiration catheter that is large enough that it is sufficiently occlusive to occlude the vessel so that there is no anterograde flow distally into the brain. According to some such embodiments, aspiration is in the direction of flow. According to some such embodiments, aspiration is opposite the direction of flow. In some embodiments, as depicted in FIG. 6, there is a balloon 430 mounted on the outside of the distal segment of the aspiration catheter, which can help occlude the vessel in some cases. In some illustrative cases, flow of clot into the aspiration catheter can then be augmented by a combination of maceration by the rotating wire loops 360 which breaks the clot into smaller pieces that can be more readily sucked up without occluding the aspiration catheter, as well irrigation into and beyond the clot, which serves to expand that segment of the vessel, thereby decreasing adherence of the clot to the vessel wall, and also serves to replace the clot and any blood that is sucked out of the vessel, thereby avoiding an "empty vacuum" phenomenon, which can cause the vessel to collapse and nothing to flow when aspiration is applied. In other embodiments an aspiration catheter without a balloon can be used, but the aspiration catheter is chosen to be of the same size or slightly larger than the target vessel, so when it is advanced into the target vessel it becomes wedged against the vessel walls, thereby obstructing normal distal flow.

As illustrated in FIG. 6, according to some embodiments, the endovascular device of the described invention may comprise an aspirator 400 comprising a proximal end 410 and a distal end 420, wherein the walls of the aspirator 400 define a lumen. As seen in FIG. 6, the macerating irrigation microcatheter 300 may protrude from the lumen of the aspirator 400 on the distal end of the aspirator 400.

According to some embodiments, the diameter of the central tube 390 of the macerating irrigation microcatheter 300 can be less than the diameter of the aspirator 400. According to some embodiments, the ratio of the diameter of the central tube 390 to the diameter of the aspirator 400 is less than 1:100. According to some embodiments, the ratio of the diameter of the central tube 390 to the diameter of the aspirator 400 is less than 1:50. According to some embodiments, the ratio of the diameter of the central tube 390 to the diameter of the aspirator 400 is less than 1:25. According to some embodiments, the ratio of the diameter of the central tube 390 to the diameter of the aspirator 400 is less than 1:20. According to some embodiments, the ratio of the diameter of the central tube 390 to the diameter of the aspirator 400 is less than 1:15. According to some embodiments, the ratio of the diameter of the central tube 390 to the diameter of the aspirator 400 is less than 1:10. According to some embodiments, the ratio of the diameter of the central tube 390 to the diameter of the aspirator 400 is less than 1:5. According to some embodiments, the ratio of the diameter of the central tube 390 to the diameter of the aspirator 400 is less than 1:4. According to some embodiments, the ratio of the diameter of the central tube 390 to the diameter of the aspirator 400 is less than 1:3. According to some embodiments, the ratio of the diameter of the central tube 390 to the diameter of the aspirator 400 is less than 1:2.

According to some embodiments, the aspirator 400 is connected to an inflatable soft balloon 430 that is effective to expand to the size of a blood vessel to occlude the blood vessel so that there is no anterograde flow distally into the brain. According to some embodiments, the soft balloon 430 is located on the distal end 420 of the aspirator 400.

FIGS. 7A and 7B show exemplary and non-limiting embodiments of the endovascular device of the described invention. As seen in FIG. 7A a microcatheter 100, as described above, is connected to, and in some versions the proximal portion is embedded within, the inner wall defining the lumen of an aspirator 400. According to some embodiments, the connection of the microcatheter 100 to the inner wall defining the lumen of the aspirator 400 maximizes the force of aspiration that can be applied to a clot by the aspirator 400. According to some embodiments, the flow of fluid in the distal to proximal direction in the aspirator is laminar. According to some embodiments, the flow of fluid in the proximal to distal direction in the microcatheter is laminar. According to some embodiments, the flow rate of fluid in the aspirator or microcatheter is described by Poiseuille's Law:

$$\text{Volume Flowrate} = (\text{Pressure difference} \times \text{radius}^4)/(8/\pi \times \text{viscosity} \times \text{length})$$

As seen in FIG. 7B a microcatheter 100, as described above, is connected to the inner wall defining the lumen of an aspirator 400, wherein the aspirator is additionally connected to a soft balloon 430.

Figure 7C:
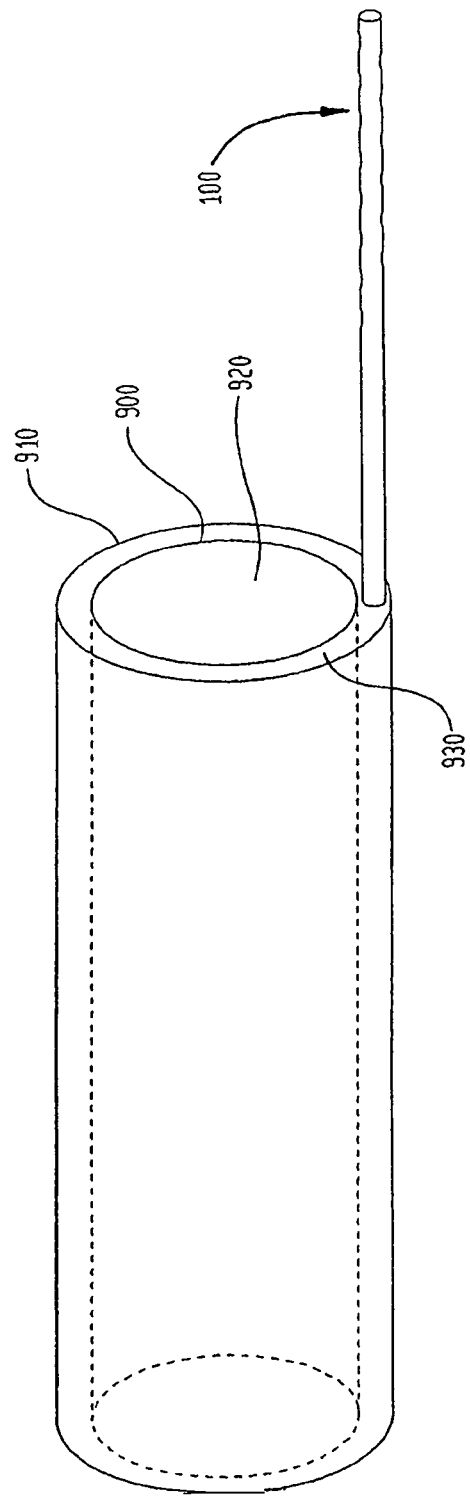
FIG. 7C shows an illustration of a perspective view of one embodiment of the endovascular device of the described invention.

FIG. 7C shows a non-limiting example of one aspect of the endovascular device of the present invention. According to some embodiments, the microcatheter is positioned between an inner wall 900 and outer wall 910 of the aspirator, wherein the inner wall defines a first luminal space 920 and the outer wall defines a second luminal space 930, and wherein the inner wall and first luminal space are disposed within the second luminal space. According to some embodiments, the microcatheter 100 is disposed in the second luminal space between the inner wall and the outer wall. According to some embodiments, the distal end of the second luminal space is sealed with the microcatheter projected through in a proximal to distal direction. According to some embodiments, the microcatheter runs the full length of the second luminal space. According to some embodiments, the microcatheter runs less than the full length of the second luminal space. According to some embodiments, the second luminal space is continuous with the luminal space defined by the microcatheter. According to some embodiments, a fluid is introduced into the second luminal space on the proximal end and ejected out from the microcatheter on the distal end, while simultaneously the first luminal space aspirates fluid in a distal to proximal direction. According to some embodiments, fluid flows through the second luminal space in a distal to proximal direction and funnels to one side into the lumen of the microcatheter. According to some embodiments, the microcatheter is disposed in the second lumen between the inner wall and outer wall, and is adapted to receive fluid which flows from the proximal end of the microcatheter to the distal end of the microcatheter.

According to some embodiments, the inflatable space defined by the soft balloon is connected to the first luminal space, which allows fluid to be injected into the soft balloon via the first luminal space from outside the patient's blood vessel. The second luminal space is a separate compartment from the first luminal space and is capable of suctioning fluid and particulates from the patient's blood vessel outside the patient's body.

Figure 7E:
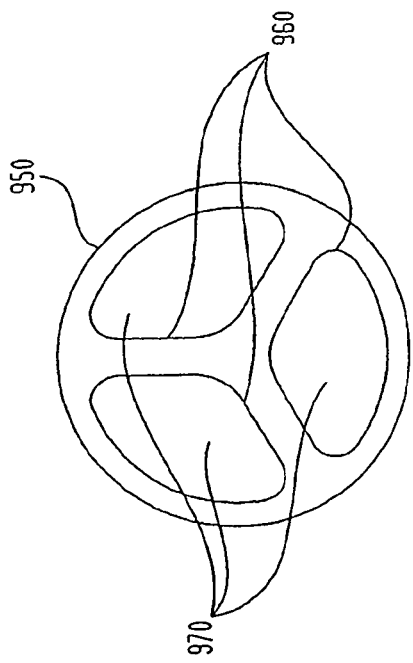
FIG. 7E shows an illustration of a cross section view of one embodiment of the endovascular device of the described invention.
Figure 7D:
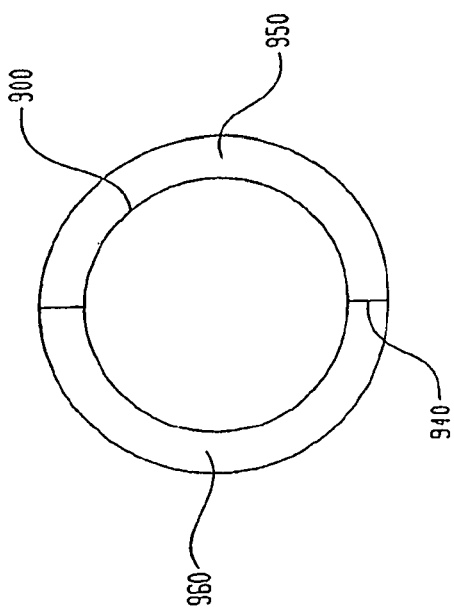
FIG. 7D shows an illustration of a cross section view of one embodiment of the endovascular device of the described invention.

According to some embodiments, the second luminal space is further divided into two or more separate spaces by a divider 940 that is connected to the inner wall and the outer wall, and that runs along the length of the inner wall and outer wall (FIG. 7D). According to some embodiments, the second luminal space is divided into a first compartment 950 and a second compartment 960. According to some embodiments, the first compartment is continuous with the lumen of the microcatheter, and the second compartment is continuous with an inner space defined by the soft balloon 430. According to some embodiments, the first compartment is adapted to flow fluid from the proximal end to the distal end of the aspirator and out the distal end of the microcatheter, and the second compartment is adapted to flow fluid into and out of the inner space defined by the soft balloon.

According to some embodiments, the described invention comprises a tube defined by an outer wall 950 and two or more inner walls 960, wherein the inner walls run as least part of the length of the outer wall and define two or more luminal spaces 970 (FIG. 7E). According to some embodiments, one or more of the luminal spaces 970 is continuous with one or more lumens of microcatheters. According to some embodiments, one or more of the luminal spaces 970 is continuous with one or more inner spaces defined by one or more soft balloons. According to some embodiments, one or more of the luminal spaces is adapted to flow fluid from the proximal end to the distal end of the aspirator and out the distal end of the microcatheter, and one or more of the luminal spaces is adapted to flow fluid into and out of the inner space define by the soft balloon.

According to some embodiments, the described invention comprises a Y-connector that includes two Luer Locks which connect two or more of the lumens defined as shown in any of FIG. 7C, 7D, 7E, or 7J such that functionally there is a separate lumen for aspiration and a separate lumen for irrigation. According to some embodiments, the present invention comprises a connector including Luer Locks which connect two or more of the lumens defined as shown in any of FIG. 7C, 7D, 7E, or 7J such that the separate lumens merge into one lumen outside the patient's body, wherein the path of fluid flow can be selected. According to some embodiments, one or more distinct lumens is/are bounded by a single structure on the distal end (e.g., FIG. 7C, 7D, 7E, or 7J), while each lumen diverges into separate branches defined by separate structures on the proximal end. According to some embodiments, the distal one or more distinct lumens bounded by a single structure is/are adapted to be inserted into a blood vessel, while the proximal divergent lumens defined by separate structures remain outside a blood vessel. According to some embodiments, the proximal divergent lumens defined by separate structures are connected to a separate Luer Lock for each lumen.

According to some embodiments, one or more of the lumens shown in any of embodiments FIG. 7C, 7D, 7E, or 7J is adapted for one or more of balloon inflation, contrast, aspiration, and irrigation. According to some embodiments, a Luer Lock is attached to the proximal end of each lumen.

According to some embodiments, the diameter of the soft balloon 430 ranges from about 1 mm to about 100 mm. According to some embodiments, the diameter of the soft balloon 430 is about 1 mm. According to some embodiments, the diameter of the soft balloon 430 is about 2 mm. According to some embodiments, the diameter of the soft balloon 430 is about 3 mm. According to some embodiments, the diameter of the soft balloon 430 is about 4 mm. According to some embodiments, the diameter of the soft balloon 430 is about 5 mm. According to some embodiments, the diameter of the soft balloon 430 is about 10 mm. According to some embodiments, the diameter of the soft balloon 430 is about 15 mm. According to some embodiments, the diameter of the soft balloon 430 is about 20 mm. According to some embodiments, the diameter of the soft balloon 430 is about 25 mm. According to some embodiments, the diameter of the soft balloon 430 is about 30 mm. According to some embodiments, the diameter of the soft balloon 430 is about 35 mm. According to some embodiments, the diameter of the soft balloon 430 is about 40 mm. According to some embodiments, the diameter of the soft balloon 430 is about 45 mm. According to some embodiments, the diameter of the soft balloon 430 is about 50 mm.

According to some embodiments, the length of the soft balloon 430 ranges from about 1 mm to about 1000 mm. According to some embodiments, the length of the soft balloon 430 is about 4 mm. According to some embodiments, the length of the soft balloon 430 is about 5 mm. According to some embodiments, the length of the soft balloon 430 is about 6 mm. According to some embodiments, the length of the soft balloon 430 is about 7 mm. According to some embodiments, the length of the soft balloon 430 is about 8 mm. According to some embodiments, the length of the soft balloon 430 is about 9 mm. According to some embodiments, the length of the soft balloon 430 is about 10 mm. According to some embodiments, the length of the soft balloon 430 is about 20 mm. According to some embodiments, the length of the soft balloon 430 is about 30 mm. According to some embodiments, the length of the soft balloon 430 is about 40 mm. According to some embodiments, the length of the soft balloon 430 is about 50 mm. According to some embodiments, the length of the soft balloon 430 is about 60 mm. According to some embodiments, the length of the soft balloon 430 is about 70 mm. According to some embodiments, the length of the soft balloon 430 is about 80 mm. According to some embodiments, the length of the soft balloon 430 is about 90 mm. According to some embodiments, the length of the soft balloon 430 is about 100 mm. According to some embodiments, the length of the soft balloon 430 is about 110 mm. According to some embodiments, the length of the soft balloon 430 is about 120 mm. According to some embodiments, the length of the soft balloon 430 is about 130 mm. According to some embodiments, the length of the soft balloon 430 is about 140 mm. According to some embodiments, the length of the soft balloon 430 is about 150 mm. According to some embodiments, the length of the soft balloon 430 is about 160 mm. According to some embodiments, the length of the soft balloon 430 is about 170 mm. According to some embodiments, the length of the soft balloon 430 is about 180 mm. According to some embodiments, the length of the soft balloon 430 is about 190 mm. According to some embodiments, the length of the soft balloon 430 is about 200 mm. According to some embodiments, the length of the soft balloon 430 is about 210 mm. According to some embodiments, the length of the soft balloon 430 is about 220 mm. According to some embodiments, the length of the soft balloon 430 is about 230 mm. According to some embodiments, the length of the soft balloon 430 is about 240 mm. According to some embodiments, the length of the soft balloon 430 is about 250 mm. According to some embodiments, the length of the soft balloon 430 is about 260 mm. According to some embodiments, the length of the soft balloon 430 is about 270 mm. According to some embodiments, the length of the soft balloon 430 is about 280 mm. According to some embodiments, the length of the soft balloon 430 is about 290 mm. According to some embodiments, the length of the soft balloon 430 is about 300 mm. According to some embodiments, the length of the soft balloon 430 is about 350 mm. According to some embodiments, the length of the soft balloon 430 is about 400 mm. According to some embodiments, the length of the soft balloon 430 is about 450 mm. According to some embodiments, the length of the soft balloon 430 is about 500 mm. According to some embodiments, the length of the soft balloon 430 is about 550 mm. According to some embodiments, the length of the soft balloon 430 is about 600 mm. According to some embodiments, the length of the soft balloon 430 is about 650 mm. According to some embodiments, the length of the soft balloon 430 is about 700 mm. According to some embodiments, the length of the soft balloon 430 is about 750 mm. According to some embodiments, the length of the soft balloon 430 is about 800 mm. According to some embodiments, the length of the soft balloon 430 is about 850 mm. According to some embodiments, the length of the soft balloon 430 is about 900 mm. According to some embodiments, the length of the soft balloon 430 is about 1000 mm.

According to some embodiments, the soft balloon 430 comprises various shapes including, but not limited, cylindrical, spherical, oval, conical, stepped, tapered and dog bone.

According to some embodiments, the soft balloon 430 comprises a material such as, for example, a polyamide, polyethylene terephthalate (PET), polyurethane, composites, and engineered nylons. Engineered nylons include, but are not limited to, Pebax®, Grilamid®, and Vestamid® or other suitable materials.

According to some embodiments, the soft balloon 430 ends comprise various shapes including, but not limited to, a conical sharp corner, a conical radius corner, an offset neck, a spherical end and a square.

According to some embodiments, the soft balloon 430 is filled with a fluid. Non-limiting examples of the fluid include sterile water, contrast, and saline.

According to some embodiments, the soft balloon 430 is adapted to occlude proximally blood flow and, in conjunction with irrigation and aspiration, to reverse the direction of flow in the blood vessel and/or to prevent the distal flow of emboli.

According to some embodiments, the aspirator is adapted to capture emboli during procedures where the direction of blood flow relative to the aspirator is from the distal end to the proximal end. According to some embodiments, the aspirator 800 comprises a flared distal end 820 that is capable of capturing emboli as blood flows in a distal end to proximal end direction (FIGS. 7F to 7I). According to some embodiments, the flared distal end 820 is adapted to guide emboli into the flared aspirator 800 for removal from the blood vessel.

According to some embodiments, the diameter of the opening at the flared distal end 820 of the flared aspirator 800 is at least 10% greater than the diameter of the proximal end 810. According to some embodiments, the diameter of the opening of the flared distal end 820 of the flared aspirator 800 is at least 15% greater than the diameter of the proximal end 810. According to some embodiments, the diameter of the opening of the flared distal end 820 of the flared aspirator 800 is at least 20% greater than the diameter of the proximal end 810. According to some embodiments, the diameter of the opening of the flared distal end 820 of the flared aspirator 800 is at least 25% greater than the diameter of the proximal end 810. According to some embodiments, the diameter of the opening of the flared distal end 820 of the flared aspirator 800 is at least 30% greater than the diameter of the proximal end 810. According to some embodiments, the diameter of the opening of the flared distal end 820 of the flared aspirator 800 is at least 35% greater than the diameter of the proximal end 810. According to some embodiments, the diameter of the opening of the flared distal end 820 of the flared aspirator 800 is at least 40% greater than the diameter of the proximal end 810. According to some embodiments, the diameter of the opening of the flared distal end 820 of the flared aspirator 800 is at least 50% greater than the diameter of the proximal end 810. According to some embodiments, the diameter of the opening of the flared distal end 820 of the flared aspirator 800 is at least 60% greater than the diameter of the proximal end 810. According to some embodiments, the diameter of the opening of the flared distal end 820 of the flared aspirator 800 is at least 65% greater than the diameter of the proximal end 810. According to some embodiments, the diameter of the opening of the flared distal end 820 of the flared aspirator 800 is at least 70% greater than the diameter of the proximal end 810. According to some embodiments, the diameter of the opening of the flared distal end 820 of the flared aspirator 800 is at least 75% greater than the diameter of the proximal end 810. According to some embodiments, the diameter of the opening of the flared distal end 820 of the flared aspirator 800 is at least 80% greater than the diameter of the proximal end 810. According to some embodiments, the diameter of the opening of the flared distal end 820 of the flared aspirator 800 is at least 85% greater than the diameter of the proximal end 810. According to some embodiments, the diameter of the opening of the flared distal end 820 of the flared aspirator 800 is at least 90% greater than the diameter of the proximal end 810. According to some embodiments, the diameter of the opening of the flared distal end 820 of the flared aspirator 800 is at least 95% greater than the diameter of the proximal end 810. According to some embodiments, the diameter of the opening of the flared distal end 820 of the flared aspirator 800 is at least 100% greater than the diameter of the proximal end 810. According to some embodiments, the diameter of the opening of the flared distal end 820 of the flared aspirator 800 is at least 200% greater than the diameter of the proximal end 810. According to some embodiments, the diameter of the opening of the flared distal end 820 of the flared aspirator 800 is at least 300% greater than the diameter of the proximal end 810. According to some embodiments, the diameter of the opening of the flared distal end 820 of the flared aspirator 800 is at least 400% greater than the diameter of the proximal end 810. According to some embodiments, the diameter of the opening of the flared distal end 820 of the flared aspirator 800 is at least 500% greater than the diameter of the proximal end 810. According to some embodiments, the diameter of the opening of the flared distal end 820 of the flared aspirator 800 is at least 600% greater than the diameter of the proximal end 810.

According to some embodiments, the diameter of the opening of the flared distal end 820 of the flared aspirator 800 is at least 700% greater than the diameter of the proximal end 810. According to some embodiments, the diameter of the opening of the flared distal end 820 of the flared aspirator 800 is at least 800% greater than the diameter of the proximal end 810. According to some embodiments, the diameter of the opening of the flared distal end 820 of the flared aspirator 800 is at least 900% greater than the diameter of the proximal end 810. According to some embodiments, the diameter of the opening of the flared distal end 820 of the flared aspirator 800 is at least 1000% greater than the diameter of the proximal end 810.

Figure 7F:
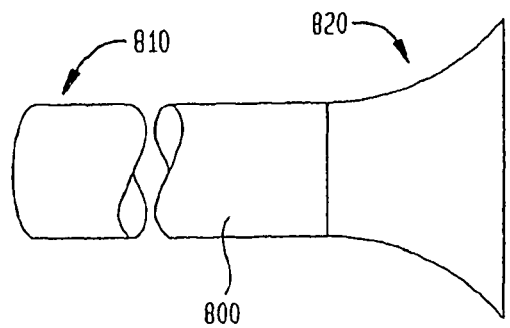
FIG. 7F shows an illustration of a side view of one embodiment of the endovascular device of the described invention.
Figure 7G:
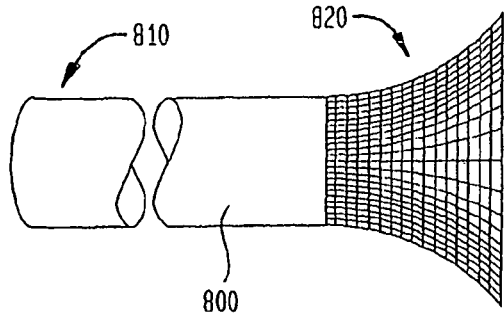
FIG. 7G shows an illustration of a side view of one embodiment of the endovascular device of the described invention.
Figure 7H:
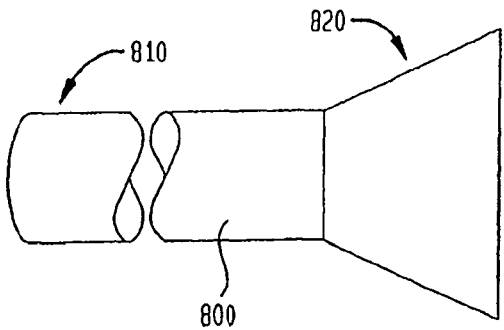
FIG. 7H shows an illustration of a side view of one embodiment of the endovascular device of the described invention.

According to some embodiments, the flared distal end 820 is a continuous extension of the flared or unflared aspirator 800. According to some embodiments, the flared aspirator comprises a solid structure that obstructs blood flow (FIG. 7F). According to some embodiments, the flared distal end comprises a mesh material that is adapted to capture emboli, but also allow passage of blood flow (FIG. 7G). By allowing continued blood flow through the mesh filter attached to the distal end of the aspiration catheter, the aspiration can be applied only intermittently, to clear thrombi and other debris from the filter. The amount of flow versus flow obstruction can be monitored by intermittent contrast venography, or by transabdominal ultrasound. Alternatively, in some iterations IVUS (intravascular or intravenus ultrasound) can be incorporated into the tip of the aspiration catheter, to allow continuous monitoring of blood flow at the tip of the aspiration catheter without the use of contrast, radiation, or a second technician performing transabdominal ultrasound. By way of nonlimiting example, the following setup can be used in a patient with a large left Iliac Vein thrombus: Venous access can be obtained via the left Femoral Vein, and separately through either Internal Jugular Vein in the neck. At the jugular vein an aspiration catheter with embedded IVUS andpo a flared filter end extension can be advanced and deployed in the upper Inferior Vena Cava, with the end hole for aspiration and the filter facing inferiorly, so as to be oriented to capture any debris as it flows in the normal venous direction from the leg to the heart. A rotational irrigating thrombectomy hypotube with side wire loops can then be advanced from the left femoral vein access across the clot in the left iliac vein. The IVUS can then start monitoring flow in the upper IVC at the tip of the aspiration catheter. But in order to minimize blood loss, aspiration is not started until some diminution of flow and buildup of embolic debris is seen. The rotational maceration and aspiration are then started, to break up and free up the clot form the iliac vein. As flow is restored in the iliac vein, debris flows to the IVC and is captured in the filter. Intermittent aspiration can then be applied as needed only, to minimize blood loss. In some cases, another rotational separator, with or without an additional irrigating element, can be advanced though the aspiration catheter, to further break up the clot and debris into smaller pieces when needed, to avoid the aspiration catheter becoming clogged. In other iterations the aspiration catheter can additionally have a wire through it hat ends inside the catheter in the tip, and uses technology to create vibrational energy, similar to the used in the Penumbra Apollo device to remove parenchymal blood from the brain, to break up the clots as they enter the tipoff the aspiration catheter, and thereby avoid clogging of the aspiration catheter.

The present invention in one embodiment includes a vibrational wire is deployed distally from or within said device. Said vibrational wire is designed to cut clots.

Figure 7I:
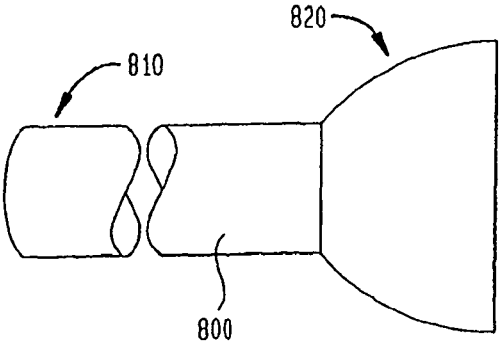
FIG. 7I shows an illustration of a side view of one embodiment of the endovascular device of the described invention.
Figure 7J:
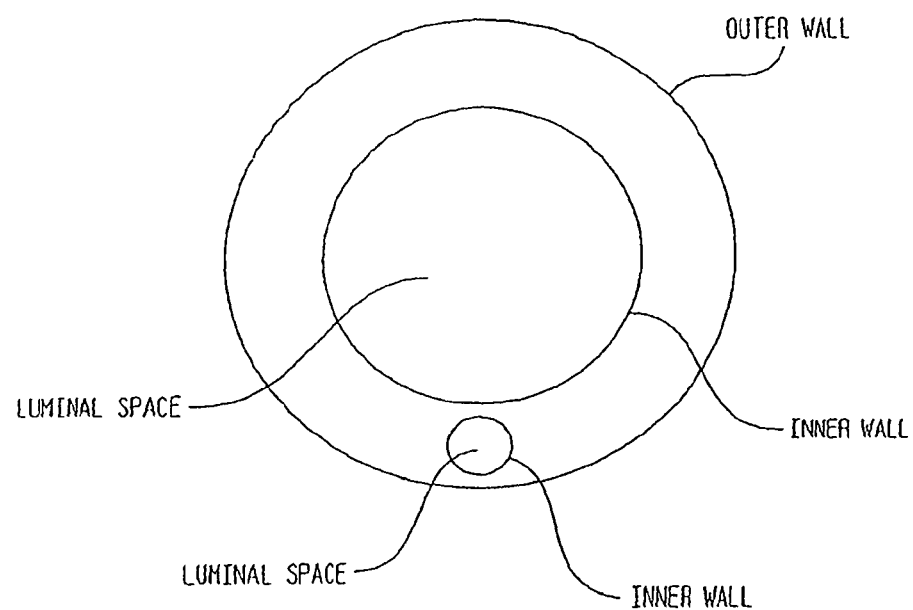
FIG. 7J shows an illustration of a cross section view of one embodiment of the endovascular device of the described invention.

According to some embodiments, the flaring of the flared end 820 is a continuously increasing flare relative to the rest of the aspirator 800, which gives the outer wall of the flared end 820 a concave shape (FIG. 7F). According to some embodiments, the flaring of the flared end 820 is abrupt and provides the outer wall of the flared end 820 with a flat shape (FIG. 7H) or a convex shape (FIG. 7I).

According to some embodiments, the diameter of the opening of the flared distal end 820 is capable of being increased or decreased relative to the diameter of the rest of the flared aspirator 800 while placed inside a blood vessel. According to some embodiments, the diameter of the opening of the flared distal end 820 is increased by inflation of a balloon attached to the inner or outer wall of the flared distal end 820 or embedded within the wall of the flared distal end 820. According to some embodiments, the flared distal end 820 is adapted to be retracted inside the lumen of the flared aspirator 800. According to some embodiments, the flared distal end 820 is made of a flexible, resilient material with a flared shape that expands while protruding from the flared aspirator 800 and collapses when retracted into the flared aspirator 800. According to some embodiments, the flared distal end 820 is adapted to cinch closed via a lasso mechanism around the periphery of the flared distal end 820. According to some embodiments, the flared aspirator 800 further comprises a macerating irrigation catheter 300 as shown and described.

Figure 7K:
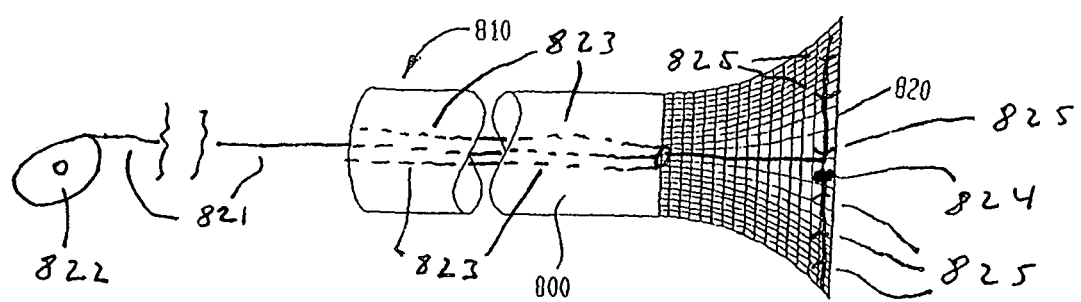
FIG. 7K shows an illustration of a cross section view of one embodiment of the endovascular device of the described invention wherein the flared distal end is adapted to cinch close with a lasso-type mechanism.

Referring now to FIG. 7K, according to embodiments having flared distal end 820 adapted to cinch closed via a lasso mechanism, said lasso mechanism is comprised of at least one string or wire 821 extending from an external reel or retraction mechanism 822. String 821 passes through flared aspirator 800 through a lasso channel 823. String 821 is fixed to periphery of flared distal end 820 at single point 824. From fixed point 824, said string travels circumferentially around said periphery of flared distal end 820 slidably through hoops 825 forming a loop or lasso about the rim. In an alternative embodiment, hoops 825 are replaced by a second lasso channel (not shown).

In operation, using the lasso mechanism of FIG. 7K, flared distal end 820 of flared aspirator 800 is cinched closed by retracting string 821 by rewinding reel 822 (or other mechanism adapted to ratchet back string), tensioning said string 821 such that the loop or lasso formed around the periphery 750 of flared distal end 820 contracts at a rate controlled by the retraction, decreasing the diameter of the opening of the flared distal end 820 to the desired diameter.

According to some embodiments, the flared distal end may be straight (non-flared) on insertion into a blood vessel, and then flare after insertion into the blood vessel. According to some embodiments, the flaring of the flared end is triggered by body temperature, unsheathing from within another catheter, or any other mechanism. According to some embodiments, the flared end is retracted (back to non-flared state) by the lasso mechanism of FIG. 7K, retraction into another catheter, retraction cables, or any other mechanism.

The present invention is a continuation in part of parents teaching a microcatheter for simultaneous rotation, separation and irrigation for thrombectomy and method which are described herein. The novel features of the present disclosure are depicted in FIGS. 18-29.

Figure 18:
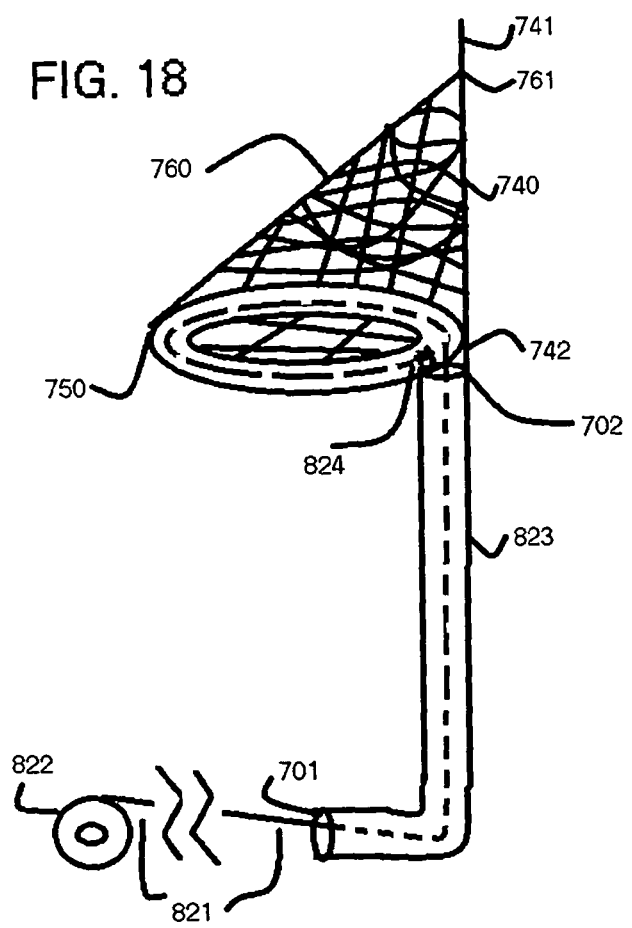
FIG. 18 shows an alternative flared filter embodiment of the disclosed invention as depicted in FIG. 7K, wherein the orientation of said filter is reversed with open ring disposed proximal to the introducing catheter, having a drawstring-type cincture.

More particularly, referring to FIG. 18, which discloses lasso channel 823. At least one string 821 is wound around reel 822 enters lasso channel 823 by proximal hole 701 and exits catheter 823 via distal hole 702. Attached to the rim of distal hole 702 is staff 740 and peripheral filter ring 750 which forms the proximal end of semi-permeable flared filter 760. Said filter 760 is attached to staff 740 such that distal tip 761 of flared filter 760 is proximal to distal tip 741 of staff 740. Staff 740 attaches to lasso channel 823 at attachment point 742. At least one string 821, upon exiting lasso channel 823 via end hole 702, extends into a channel around peripheral ring 750 and is attached to fixation point 824. The portion of string 821 in ring 750 is slidable. Fixation point 824 is located on the rim of distal hole 702. Peripheral filter ring 750 may be rigid or semirigid. String 821 may be a string or a cable, said string or cable 821 may be malleable, rigid, or semirigid.

Figure 19:
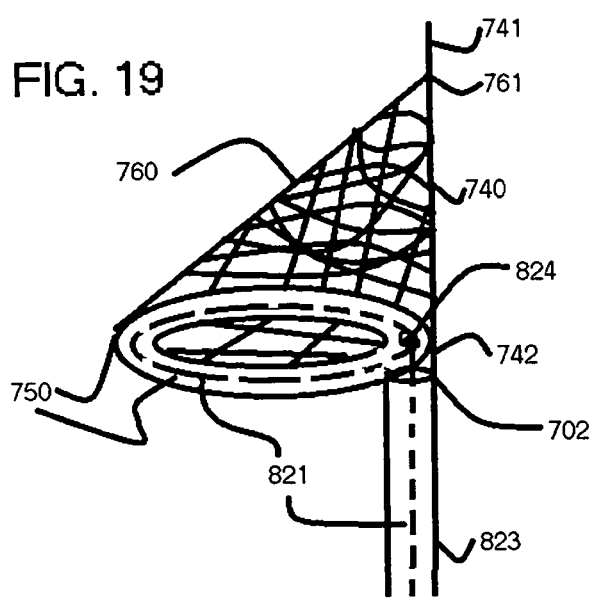
FIG. 19 shows an alternative flared filter embodiment of the disclosed invention as depicted in FIG. 19, wherein the cincture is a lasso-type.

Now referring to the optional embodiment shown in FIG. 19, the distal end of string 821 is attached to a proximal section of string 821 at attachment point 824 forming a fixed-length lasso. In this embodiment, no fixed-point 824 is required. When string 821 is retracted, the lasso diameter outside end hole 702 decreases, and closes the proximal opening of flared filter 760.

Figure 20:
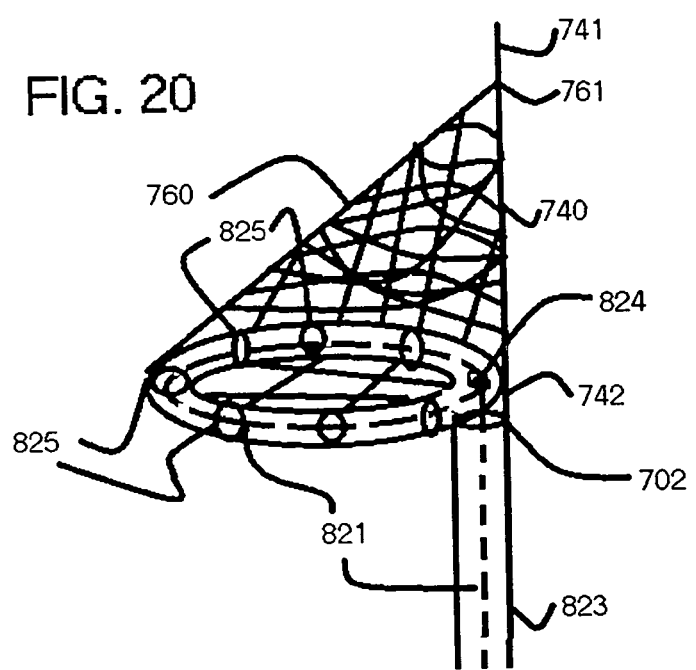
FIG. 20 shows alternative flared filter embodiment of the disclosed invention as depicted in FIG. 19, wherein the cincture encloses the at least one control string or wire in an array of hoops disposed about the periphery of the rim of said flared filter.
Figure 21:
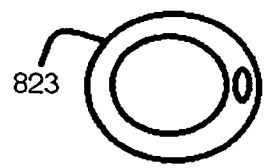
FIG. 21A shows a cross-section (A-A) of the alternate embodiment shown in FIG. 18 of the lasso channel or lumen.
FIG. 21B shows a cross-section of a filter-tipped lasso channel including moveable elements.
Figure 21:
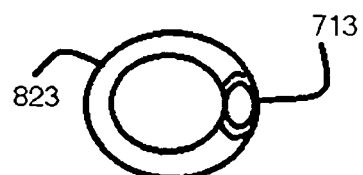

Now referring to an alternate embodiment shown in FIG. 20, peripheral ring 750 is disposed with hoops 825 instead of a channel wherein string 821 passes through and terminates at fixation point 824.

Now referring to an alternate embodiment shown in FIG. 21A, a cross-sectional view (line A-A of FIG. 18) of the lasso channel 823. Within said cross-section is disposed a moveable element 713, which is part of the lasso channel 823 wall. In this embodiment, filter elements not mounted to the tip of lasso channel 823 may be deployed.

FIG. 21B presents an alternate embodiment of filter-tipped lasso channel 823 which includes moveable elements 713.

Figure 22:
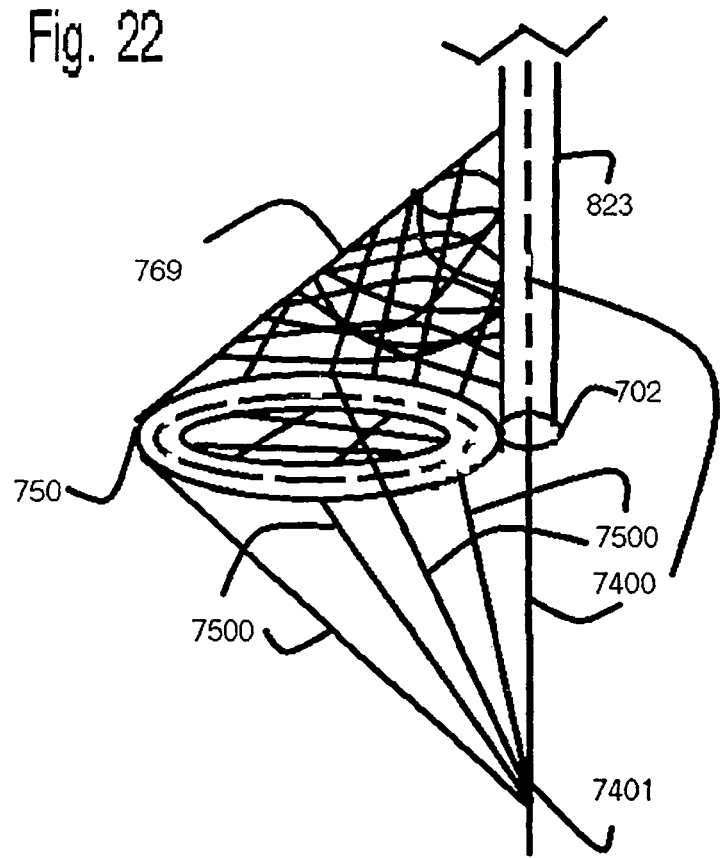
FIG. 22 shows an alternative of the embodiment of FIG. 18, wherein the flared filter is depicted in an opposite orientation, wherein a staff wire and strut wires facilitate the closing mechanism.

Now referring to an alternate embodiment shown in FIG. 22, flared filter 769 is depicted in an opposite orientation from the embodiment of filter 760 shown in FIG. 18. Said oppositely oriented filter 769 is fixed to the outside of lasso channel 823 along its length. Rim 750 of filter 769 is attached to staff wire 7400 via strut wires 7500. Each strut wire 7500 attaches at each end, one end at dispersed points about peripheral rim 750 of rotated filter 769, and the opposite end of each strut wire or string 7500 together at single junction point 7401 on staff wire 7400. Staff wire 7400 runs through lasso channel 823 from reel or ratcheting mechanism 822 through and out distal hole 702. The rotation of reel or ratcheting mechanism 822 allows either the lengthening or shortening of wire 7400 which in turn contracts or expands the distance between strut wires 7500, which allows the opening and closing of peripheral ring 750 of filter 769.

Figure 23:
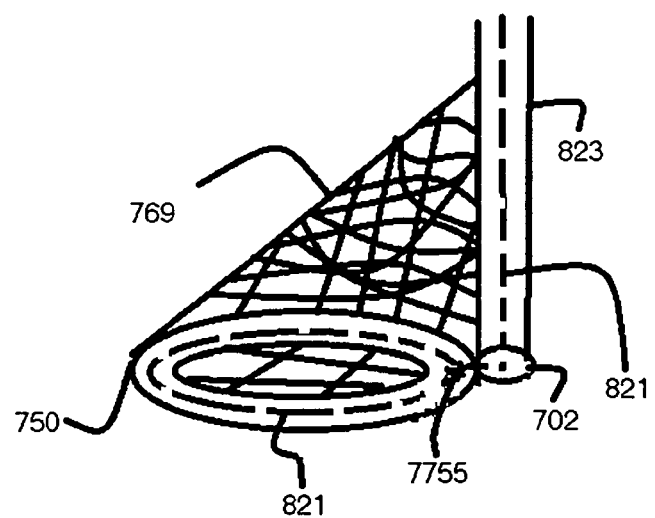
FIG. 23 shows an alternative embodiment of FIG. 22, further depicting an attachment point forming a fixed-length lasso without a staff wire or strut wires.

Now referring to another embodiment shown in FIG. 23, disclosed is the oppositely-oriented flared filter 769 of FIG. 22 without a staff wire 7400 or strut wires 7500. In this embodiment, attachment point 7755 forms a fixed-length lasso closing mechanism.

Figure 24:
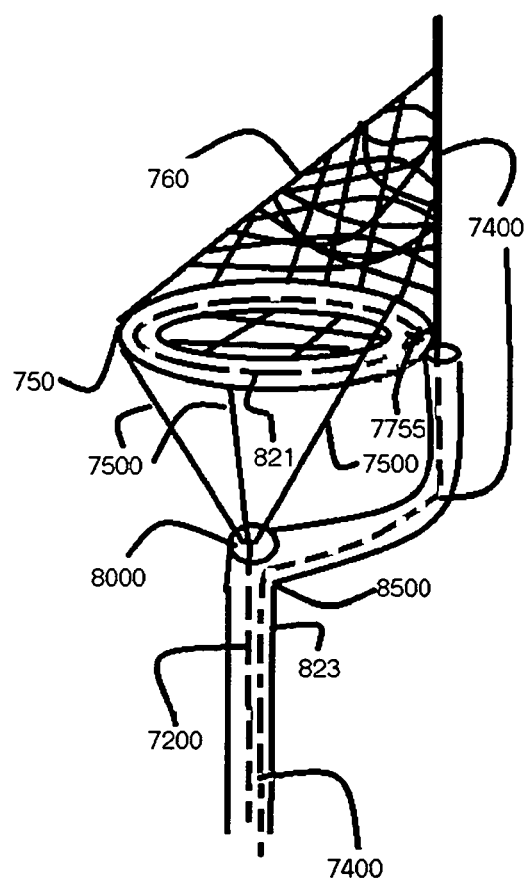
FIG. 24 shows an alternative embodiment of the current invention wherein opening and closing of the flared uses an additional control string or wire passing through a side hole of the lasso channel disposed at a bend.

Referring now to FIG. 24, disclosed is yet another embodiment shown wherein flared filter 760 opens and closes by additional string 7200 passing through side hole 8000 of lasso channel 823. Side hole 8000 is located at bend 8500. The distal end of said string 7200 is attached to the proximal end at least one strut string or wires 7500, The distal end of strut string or wires 7500, in turn, attach to rim 750. When string 7200 is extended or withdrawn through lasso channel 823, strut strings 7500 lengthens or contracts which opens or closes peripheral ring 750.

Figure 25:
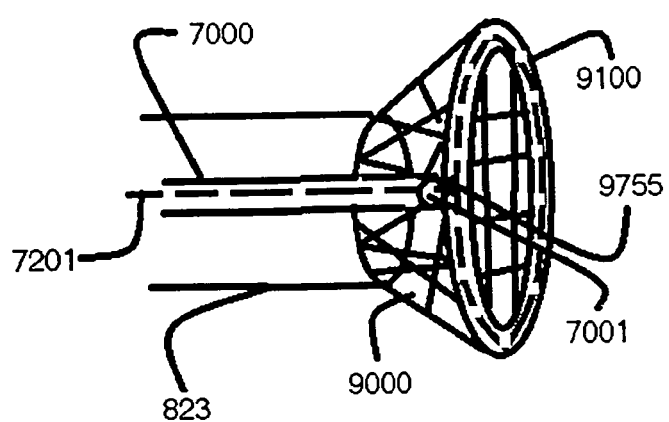
FIG. 25 shows an alternative embodiment of the current invention having a filtered-tip affixed at the distal end of the lasso channel with a fixed-loop closing mechanism.

Now referring to FIG. 25, disclosed is another embodiment having a filtered-tip 9000 affixed at the tip of lasso channel 823 with a fixed-loop closing mechanism. In this embodiment, the fixed-loop closing mechanism is embodied by having the distal end of at least one string or wire 7201 fixed to a proximal point on at least one string or wire 7201 forming a fixed-loop closing mechanism which operates as follows: when at least one string 7201 is pulled through the distal end 7001 of inner catheter 7000, such that the distal rim 9100 of filtered-tip 9000 closes. Filtered-tip 9000 is usually self-expanding but can be optionally restrained by the "lasso" element for insertion. In a further alternative, said filtered-tip 9000 can be delivered through an outer delivery catheter, optionally including a "rapid exchange" catheter. Filtered-tip 9000 further includes at least one collapsible ring channel 9100 peripherally disposed at the distal end of filtered-tip 9000. Lasso channel 823 in this embodiment further encloses inner catheter 7000 which, in turn, contains at least one string 7201. Said at least one string 7201 further depicting attachment point 9755 forming a fixed-length lasso. When at least one string 7201 is extended or withdrawn through catheter 7000, string 7201 lengthens or contracts which opens or closes peripheral ring 9100. Said at least one string 7201 may be rigid or semirigid.

Figure 26:
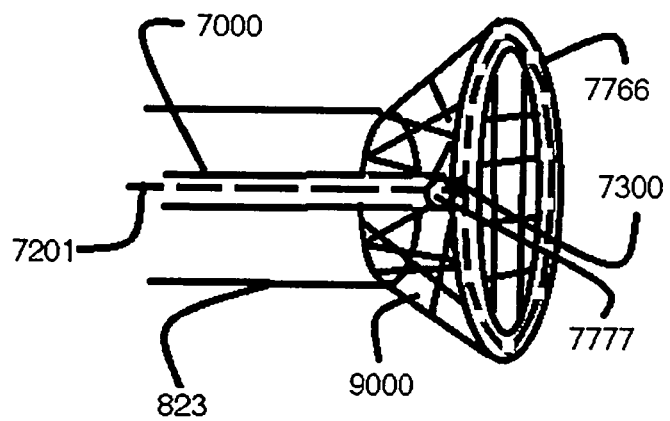
FIG. 26 shows an alternative embodiment of FIG. 25, wherein the fixed-loop closing mechanism is replaced by a drawstring-closing mechanism.

FIG. 26 discloses the embodiment of FIG. 25, wherein the fixed-loop closing mechanism is replaced by a drawstring-closing mechanism. More particularly, in the alternate embodiment of filtered-tip 9000 affixed at the tip of lasso channel 823, the distal end of at least one string 7201, after passing out of the distal end hole 7777 of catheter 7000, circles through channel 7766 which is located on the distal end of filtered-tip 9000, and returns to a fixation point 7300 located on the tip of catheter 7000. This drawstring mechanism operates by extending or withdrawing string 7201 which in turn opens or closes channel 7766, which in turn opens and closes filtered-tip 9000.

Figure 27:
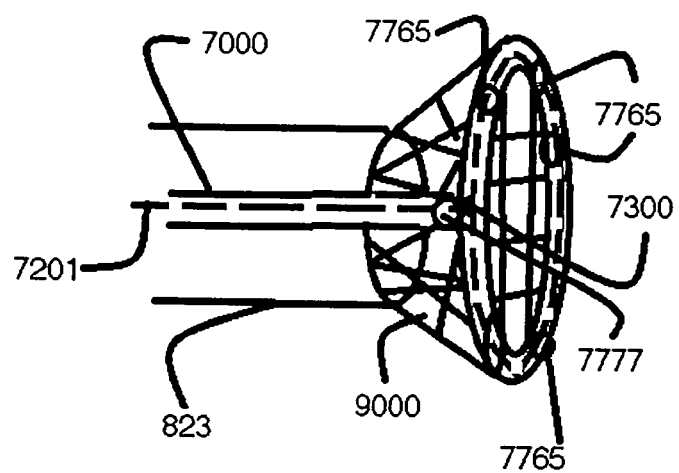
FIG. 27 an alternative embodiment of FIG. 26, wherein the control string or wire closing mechanism is contained by hoops instead of a peripheral channel.

FIG. 27 discloses the embodiment of FIG. 26, wherein channel 7766 is replaced by hoops 7765.

Figure 28:
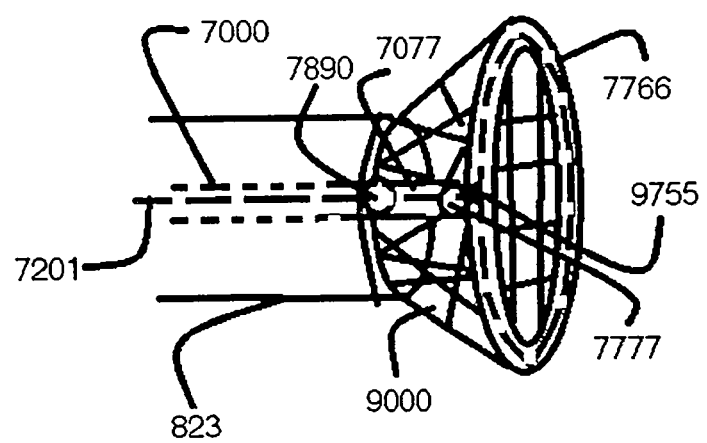
FIG. 28 shows an alternative embodiment of FIG. 26, wherein the catheter is embedded in the wall of lasso channel to form a drawstring closing mechanism.

FIG. 28 discloses the embodiment of FIG. 26, wherein catheter 7000 is embedded in the wall of lasso channel 823, thus resulting in a drawstring closing mechanism. Catheter segment 7077 is the portion of embedded catheter 7000 that exits the wall of channel 823 at location 7890. Element 7077 located at the proximal section of catheter 7000 is collapsible.

Figure 29:
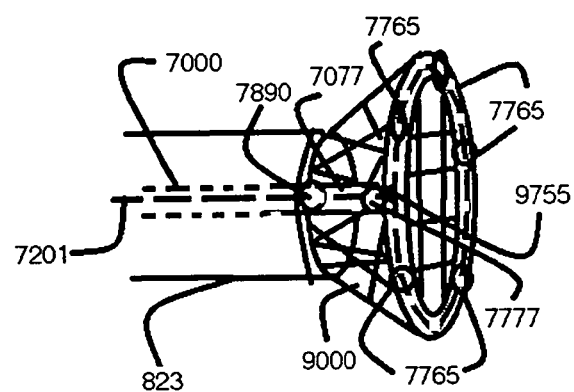
FIG. 29 shows an alternative embodiment of FIG. 28, wherein the control string or wire closing mechanism is contained by hoops instead of a peripheral channel.

FIG. 29 discloses the embodiment of FIG. 28, wherein channel 7766 is replaced by hoops 7765.

The various components of the described invention may comprise one or more materials. For example, according to some embodiments, the components can comprise one or more of thermoplastics, a thermoset, a composite or a radiopaque filler.

Thermoplastics include, but are not limited to, nylon, polyethylene terephthalate (PET), urethane, polyethylene, polyvinyl chloride (PVC) and polyether ether ketone (PEEK).

Thermosets include, but are not limited to, silicone, polytetrafluoroethylene (PTFE) and polyimide.

Composites include, but are not limited to, liquid crystal polymers (LCP). LCPs are partially crystalline aromatic polyesters based on p-hydroxybenzoic acid and related monomers. LCPs are highly ordered structures when liquid, but the degree of order is less than that of a regular solid crystal. LCPs can be substituted for such materials as ceramics, metals, composites and other plastics due to their strength at extreme temperatures and resistance to chemicals, weathering, radiation and heat. Non-limiting examples of LCPs include wholly or partially aromatic polyesters or copolyesters such as XYDAR® (Amoco) or VECTRA® (Hoechst Celanese). Other commercial liquid crystal polymers include SUMIKOSUPER™ and EKONOL™ (Sumitomo Chemical), DuPont HX™ and DuPont ZENITE™ (E.I. DuPont de Nemours), RODRUN™ (Unitika) and GRANLAR™ (Grandmont).

Non-limiting examples of radiopaque fillers include barium sulfate, bismuth oxychloride, tantalum and the like.

According to some embodiments, the invention comprises component parts made of material and dimensions having varying stiffness. According to some embodiments, the invention comprises component parts made of material and dimensions having the same stiffness. The term "stiffness" as used herein refers to the extent to which an object resists deformation in response to an applied force. By way of non-limiting example, according to some embodiments, the stiffness of the half-loop structures is less than the rotational stiffness of the central tube. According to some embodiments, the stiffness of the half loop structures is such that the half loop structures bend upon contact with a thrombosis while being rotated within a blood vessel. According to some embodiments, the stiffness of the half loop structures is such that the half loop structures do not bend upon contact with a thrombosis while being rotated within a blood vessel. According to some embodiments, the stiffness of the half loop structures is variable; i.e. some half loop structures have a greater or lesser stiffness compared to other half loop structures.

According to some embodiments, the microcatheter can extend beyond the opening of the aspiration catheter between 0.1 cm and 100 cm. According to some embodiments, the microcatheter can extend beyond the opening of the aspiration catheter by 5 cm. According to some embodiments, the microcatheter can extend beyond the opening of the aspiration catheter by 10 cm. According to some embodiments, the microcatheter can extend beyond the opening of the aspiration catheter by 15 cm. According to some embodiments, the microcatheter can extend beyond the opening of the aspiration catheter by 20 cm. According to some embodiments, the microcatheter can extend beyond the opening of the aspiration catheter by 25 cm. According to some embodiments, the microcatheter can extend beyond the opening of the aspiration catheter by 30 cm. According to some embodiments, the microcatheter can extend beyond the opening of the aspiration catheter by 35 cm. According to some embodiments, the microcatheter can extend beyond the opening of the aspiration catheter by 40 cm. According to some embodiments, the microcatheter can extend beyond the opening of the aspiration catheter by 45 cm. According to some embodiments, the microcatheter can extend beyond the opening of the aspiration catheter by 50 cm. According to some embodiments, the microcatheter can extend beyond the opening of the aspiration catheter by 60 cm. According to some embodiments, the microcatheter can extend beyond the opening of the aspiration catheter by 70 cm. According to some embodiments, the microcatheter can extend beyond the opening of the aspiration catheter by 80 cm. According to some embodiments, the microcatheter can extend beyond the opening of the aspiration catheter by 90 cm. According to some embodiments, the microcatheter can extend beyond the opening of the aspiration catheter by 100 cm.

According to some embodiments, one or more of the microwire, microcatheter, or aspiration catheter comprises a length of between 5 cm and 500 cm. According to some embodiments, one or more of the microwire, microcatheter, or aspiration catheter comprises a length of 10 cm. According to some embodiments, one or more of the microwire, microcatheter, or aspiration catheter comprises a length of 20 cm. According to some embodiments, one or more of the microwire, microcatheter, or aspiration catheter comprises a length of 30 cm. According to some embodiments, one or more of the microwire, microcatheter, or aspiration catheter comprises a length of 40 cm. According to some embodiments, one or more of the microwire, microcatheter, or aspiration catheter comprises a length of 50 cm. According to some embodiments, one or more of the microwire, microcatheter, or aspiration catheter comprises a length of 70 cm. According to some embodiments, one or more of the microwire, microcatheter, or aspiration catheter comprises a length of 90 cm. According to some embodiments, one or more of the microwire, microcatheter, or aspiration catheter comprises a length of 100 cm. According to some embodiments, one or more of the microwire, microcatheter, or aspiration catheter comprises a length of 120 cm. According to some embodiments, one or more of the microwire, microcatheter, or aspiration catheter comprises a length of 140 cm. According to some embodiments, one or more of the microwire, microcatheter, or aspiration catheter comprises a length of 160 cm. According to some embodiments, one or more of the microwire, microcatheter, or aspiration catheter comprises a length of 180 cm. According to some embodiments, one or more of the microwire, microcatheter, or aspiration catheter comprises a length of 200 cm. According to some embodiments, one or more of the microwire, microcatheter, or aspiration catheter comprises a length of 250 cm. According to some embodiments, one or more of the microwire, microcatheter, or aspiration catheter comprises a length of 300 cm. According to some embodiments, one or more of the microwire, microcatheter, or aspiration catheter comprises a length of 350 cm. According to some embodiments, one or more of the microwire, microcatheter, or aspiration catheter comprises a length of 400 cm. According to some embodiments, one or more of the microwire, microcatheter, or aspiration catheter comprises a length of 450 cm. According to some embodiments, one or more of the microwire, microcatheter, or aspiration catheter comprises a length of 500 cm.

According to some embodiments, the half loop structures comprise a length (i.e. the distance from the surface to which they are attached to the farthest part of the half loop from that surface) of 0.1 mm to 5 cm. According to some embodiments, the half loop structures comprise a length of 0.1 mm. According to some embodiments, the half loop structures comprise a length of 0.5 mm. According to some embodiments, the half loop structures comprise a length of 1 mm. According to some embodiments, the half loop structures comprise a length of 2 mm. According to some embodiments, the half loop structures comprise a length of 4 mm. According to some embodiments, the half loop structures comprise a length of 6 mm. According to some embodiments, the half loop structures comprise a length of 8 mm. According to some embodiments, the half loop structures comprise a length of 1 cm. According to some embodiments, the half loop structures comprise a length of 2 cm. According to some embodiments, the half loop structures comprise a length of 3 cm. According to some embodiments, the half loop structures comprise a length of 4 cm. According to some embodiments, the half loop structures comprise a length of 5 cm.

According to some embodiments, the central wire and/or microcatheter is straight. According to some embodiments, the central wire and/or microcatheter is curved. According to some embodiments, the central wire and/or microcatheter comprises one or more bends of between 5 degrees and 85 degrees before or within the region comprising side holes or half loop structures. According to some embodiments, the central wire and/or microcatheter comprises one or more bends of 5 degrees before or within the region comprising side holes or half loop structures. According to some embodiments, the central wire and/or microcatheter comprises one or more bends of 15 degrees before or within the region comprising side holes or half loop structures. According to some embodiments, the central wire and/or microcatheter comprises one or more bends of 25 degrees before or within the region comprising side holes or half loop structures. According to some embodiments, the central wire and/or microcatheter comprises one or more bends of 35 degrees before or within the region comprising side holes or half loop structures. According to some embodiments, the central wire and/or microcatheter comprises one or more bends of 45 degrees before or within the region comprising side holes or half loop structures. According to some embodiments, the central wire and/or microcatheter comprises one or more bends of 55 degrees before or within the region comprising side holes or half loop structures. According to some embodiments, the central wire and/or microcatheter comprises one or more bends of 65 degrees before or within the region comprising side holes or half loop structures. According to some embodiments, the central wire and/or microcatheter comprises one or more bends of 75 degrees before or within the region comprising side holes or half loop structures. According to some embodiments, the central wire and/or microcatheter comprises one or more bends of 85 degrees before or within the region comprising side holes or half loop structures.

According to some embodiments, the central wire and/or microcatheter comprises one or more bends before or within the region comprising the side holes or half loop structures such that it is adapted for large vessel application (e.g. pulmonary artery and iliac vein/inferior vena cava) so a small device can still effectively sweep along the walls of the blood vessel. According to some embodiments, the distal portion of the central wire and/or microcatheter comprises a repeating curve or other shape (e.g., sinusoidal shape).

According to some embodiments, a microcatheter or a central wire comprises a repeating curve or other shape that is adapted to macerate a clot while rotating within and/or beyond the clot. According to some embodiments, a microcatheter or a central wire comprises an irregular shape that is adapted to macerate a clot while rotating within and/or beyond the clot. According to some embodiments, a microcatheter or central wire can have a repeating curve or irregular shape at the distal end. According to some embodiments, a microcatheter or central wire can rotate around the central axis of the blood vessel in which the microcatheter or central wire is disposed. According to some embodiments, when the microcatheter or central wire are rotated around the central axis of the blood vessel, a repeating curve or irregular shaped portion at the distal end will sweep the interior space of the blood vessel, and break up or macerate a blockage.

According to some embodiments, the described invention can be used in an endovascular procedure in a subject suffering from an arterial thrombosis or embolus. According to some embodiments, the described invention can be used in an endovascular procedure in a subject suffering from a venous thrombus or embolus. According to some embodiments, the described invention can be used in an endovascular procedure in a subject suffering from deep vein thrombosis of the leg or arm. According to some embodiments, the described invention can be used in an endovascular procedure in a subject suffering from myocardial infarction with thrombus. According to some embodiments, the described invention can be used in an endovascular procedure in a subject suffering from cerebral venous sinus thrombosis. According to some embodiments, the described invention can be used in an endovascular procedure in a subject suffering from acute stroke. According to some embodiments, the described invention can be used in an endovascular procedure comprising mechanical thrombectomy. According to some embodiments, the described invention can be used in an endovascular procedure comprising proximal endovascular thrombectomy. According to some embodiments, the described invention can be used in an endovascular procedure comprising distal endovascular thrombectomy. According to some embodiments, the described invention can be used in an endovascular procedure comprising percutaneous coronary intervention (PCI). According to some embodiments, the described invention can be used in an endovascular procedure comprising atherectomy. According to some embodiments, the described invention can be used in conjunction with self-expanding stents and retrievable thrombectomy stents. According to some embodiment, the described invention is adapted to traverse one or more blood vessels (e.g. vein or artery) of the legs, arms, torso, neck, and head. According to some embodiments, the described invention is adapted to be a universal device capable of traversing any blood vessel (e.g. vein or artery) in the human or animal body.

According to some embodiments, an aspiration catheter 1020 as depicted in FIG. 8 comprises a semipermeable filter 1030 connected to the aspirating end of the catheter. According to some embodiments, the semipermeable filter 1030 allows blood cells to pass through unimpeded, but captures emboli. According to some embodiments, the semipermeable filter comprises a flared shape, wherein the distal edge 1060 of the filter comprises a greater diameter than the remaining portion of the filter (e.g. the shape of the bell of a trombone). According to some embodiments, the distal edge 1060 of the semi-permeable filter 1030 is able to expand to the diameter of a blood vessel, thereby forcing all blood traversing the blood vessel to pass through the filter.

According to some embodiments, the diameter of the distal edge 1060 of the semi-permeable filter comprises a diameter at least 10% greater than the diameter of the aspiration catheter 1020. According to some embodiments, the diameter of the distal edge 1060 of the semi-permeable filter comprises a diameter at least 15% greater than the diameter of the aspiration catheter 1020. According to some embodiments, the diameter of the distal edge 1060 of the semi-permeable filter comprises a diameter at least 20% greater than the diameter of the aspiration catheter 1020. According to some embodiments, the diameter of the distal edge 1060 of the semi-permeable filter comprises a diameter at least 25% greater than the diameter of the aspiration catheter 1020. According to some embodiments, the diameter of the distal edge 1060 of the semi-permeable filter comprises a diameter at least 30% greater than the diameter of the aspiration catheter 1020. According to some embodiments, the diameter of the distal edge 1060 of the semi-permeable filter comprises a diameter at least 35% greater than the diameter of the aspiration catheter 1020. According to some embodiments, the diameter of the distal edge 1060 of the semi-permeable filter comprises a diameter at least 40% greater than the diameter of the aspiration catheter 1020. According to some embodiments, the diameter of the distal edge 1060 of the semi-permeable filter comprises a diameter at least 45% greater than the diameter of the aspiration catheter 1020. According to some embodiments, the diameter of the distal edge 1060 of the semi-permeable filter comprises a diameter at least 50% greater than the diameter of the aspiration catheter 1020. According to some embodiments, the diameter of the distal edge 1060 of the semi-permeable filter comprises a diameter at least 55% greater than the diameter of the aspiration catheter 1020. According to some embodiments, the diameter of the distal edge 1060 of the semi-permeable filter comprises a diameter at least 60% greater than the diameter of the aspiration catheter 1020. According to some embodiments, the diameter of the distal edge 1060 of the semi-permeable filter comprises a diameter at least 65% greater than the diameter of the aspiration catheter 1020. According to some embodiments, the diameter of the distal edge 1060 of the semi-permeable filter comprises a diameter at least 70% greater than the diameter of the aspiration catheter 1020. According to some embodiments, the diameter of the distal edge 1060 of the semi-permeable filter comprises a diameter at least 75% greater than the diameter of the aspiration catheter 1020. According to some embodiments, the diameter of the distal edge 1060 of the semi-permeable filter comprises a diameter at least 80% greater than the diameter of the aspiration catheter 1020. According to some embodiments, the diameter of the distal edge 1060 of the semi-permeable filter comprises a diameter at least 85% greater than the diameter of the aspiration catheter 1020. According to some embodiments, the diameter of the distal edge 1060 of the semi-permeable filter comprises a diameter at least 90% greater than the diameter of the aspiration catheter 1020. According to some embodiments, the diameter of the distal edge 1060 of the semi-permeable filter comprises a diameter at least 95% greater than the diameter of the aspiration catheter 1020. According to some embodiments, the diameter of the distal edge 1060 of the semi-permeable filter comprises a diameter at least 100% greater than the diameter of the aspiration catheter 1020. According to some embodiments, the diameter of the distal edge 1060 of the semi-permeable filter comprises a diameter at least 200% greater than the diameter of the aspiration catheter 1020. According to some embodiments, the diameter of the distal edge 1060 of the semi-permeable filter comprises a diameter at least 300% greater than the diameter of the aspiration catheter 1020. According to some embodiments, the diameter of the distal edge 1060 of the semi-permeable filter comprises a diameter at least 400% greater than the diameter of the aspiration catheter 1020. According to some embodiments, the diameter of the distal edge 1060 of the semi-permeable filter comprises a diameter at least 500% greater than the diameter of the aspiration catheter 1020. According to some embodiments, the diameter of the distal edge 1060 of the semi-permeable filter comprises a diameter at least 600% greater than the diameter of the aspiration catheter 1020. According to some embodiments, the diameter of the distal edge 1060 of the semi-permeable filter comprises a diameter at least 700% greater than the diameter of the aspiration catheter 1020. According to some embodiments, the diameter of the distal edge 1060 of the semi-permeable filter comprises a diameter at least 800% greater than the diameter of the aspiration catheter 1020. According to some embodiments, the diameter of the distal edge 1060 of the semi-permeable filter comprises a diameter at least 900% greater than the diameter of the aspiration catheter 1020. According to some embodiments, the diameter of the distal edge 1060 of the semi-permeable filter comprises a diameter at least 1000% greater than the diameter of the aspiration catheter 1020.

According to some embodiments, the semi-permeable filter 1030 comprises a net structure as depicted in FIGS. 11A, 11B, 12A, 12B, and 13 that is effective to capture emboli that can result from maceration of a blood clot. According to some embodiments, the semi-permeable filter 1030 is effective to capture particulates greater than 10 μm in size. According to some embodiments, the semi-permeable filter 1030 is effective to capture particulates greater than 15 μm in size. According to some embodiments, the semi-permeable filter 1030 is effective to capture particulates greater than 20 μm in size. According to some embodiments, the semi-permeable filter 1030 is effective to capture particulates greater than 30 μm in size. According to some embodiments, the semi-permeable filter 1030 is effective to capture particulates greater than 40 μm in size. According to some embodiments, the semi-permeable filter 1030 is effective to capture particulates greater than 50 μm in size. According to some embodiments, the semi-permeable filter 1030 is effective to capture particulates greater than 70 μm in size. According to some embodiments, the semi-permeable filter 1030 is effective to capture particulates greater than 100 μm in size. According to some embodiments, the semi-permeable filter 1030 is effective to capture particulates greater than 500 μm in size.

According to some embodiments, as depicted in FIG. 8, the semi-permeable filter is held in a non-expanded state by rigid wings 1040 connected to a central tube 1050. According to some embodiment, the wings 1040 are formed in the shape of a skirt that defines a space in which the compressed semi-permeable filter can reside. According to some embodiments, the edge 1070 of the wings 1040 comprises a diameter less than the internal diameter of the aspiration catheter 1020. According to some embodiments, the rigidity of the wings 1040 opposes the expansion of the semipermeable filter 1030 into an expanded shape. According to some embodiments, the wings 1040 completely surround the semi-permeable filter 1030. According to some embodiments, the wings 1040 only partially surround the semi-permeable filter.

According to some embodiments, the wings 1040 and central tube 1050 can be pushed in a direction away from the aspiration catheter 1020 and semi-permeable filter 1030 by an introducer 1010. According to some embodiments, the introducer 1010 surrounds the central tube 1050, and can move independently along the length of central tube 1050. According to some embodiments, the introducer can push the central tube 1050 and wings 1040 away from the semi-permeable filter such that the expansion of the semi-permeable filter 1030 is no longer constrained by the wings 1040. According to some embodiments, the introducer 1010 can be removed from the central tube 1050 and aspiration catheter 1020 by withdrawing along the length of the central tube and aspiration catheter.

According to some embodiments, the outer diameter of the introducer 1010 is approximately equal to the inner diameter of the aspiration catheter 1020. According to some embodiments, the outer diameter of the introducer 1010 is equal to 95% of the inner diameter of the aspiration catheter 1020. According to some embodiments, the outer diameter of the introducer 1010 is equal to 90% of the inner diameter of the aspiration catheter 1020. According to some embodiments, the outer diameter of the introducer 1010 is equal to 85% of the inner diameter of the aspiration catheter 1020. According to some embodiments, the outer diameter of the introducer 1010 is equal to 80% of the inner diameter of the aspiration catheter 1020. According to some embodiments, the outer diameter of the introducer 1010 is equal to 75% of the inner diameter of the aspiration catheter 1020. According to some embodiments, the outer diameter of the introducer 1010 is equal to 70% of the inner diameter of the aspiration catheter 1020. According to some embodiments, the outer diameter of the introducer 1010 is equal to 65% of the inner diameter of the aspiration catheter 1020. According to some embodiments, the outer diameter of the introducer 1010 is equal to 60% of the inner diameter of the aspiration catheter 1020. According to some embodiments, the outer diameter of the introducer 1010 is equal to 55% of the inner diameter of the aspiration catheter 1020. According to some embodiments, the outer diameter of the introducer 1010 is equal to 50% of the inner diameter of the aspiration catheter 1020. According to some embodiments, the outer diameter of the introducer 1010 is equal to 45% of the inner diameter of the aspiration catheter 1020. According to some embodiments, the outer diameter of the introducer 1010 is equal to 40% of the inner diameter of the aspiration catheter 1020. According to some embodiments, the outer diameter of the introducer 1010 is equal to 35% of the inner diameter of the aspiration catheter 1020. According to some embodiments, the outer diameter of the introducer 1010 is equal to 30% of the inner diameter of the aspiration catheter 1020. According to some embodiments, the outer diameter of the introducer 1010 is equal to 25% of the inner diameter of the aspiration catheter 1020. According to some embodiments, the outer diameter of the introducer 1010 is equal to 20% of the inner diameter of the aspiration catheter 1020. According to some embodiments, the outer diameter of the introducer 1010 is equal to 15% of the inner diameter of the aspiration catheter 1020. According to some embodiments, the outer diameter of the introducer 1010 is equal to 10% of the inner diameter of the aspiration catheter 1020. According to some embodiments, the outer diameter of the introducer 1010 is equal to 5% of the inner diameter of the aspiration catheter 1020. According to some embodiments, the outer diameter of the introducer 1010 is equal to 1% of the inner diameter of the aspiration catheter 1020.

According to some embodiments, the wings 1040 and central tube 1050 can be removed from the blood vessel by withdrawing them through the opening and along the length of the aspiration catheter 1020. According to some embodiments, the edge 1070 of the wings 1040 comprises a diameter less than the opening of the aspiration catheter 1020 so that the wings and central tube 1050 may be withdrawn through the opening and along the length of the inside of the aspiration catheter.

With reference to FIG. 9, the central tube is a hypotube 390 that rotates, macerates and irrigates inside blood vessel 2000 (shown cutaway). Hypotube 390 further includes multiple irrigation side holes 330, proximal end hole 350 and distal end hole 340. In one embodiment hypotube 390 is sinusoidal.

This embodiment differs from prior art in that the present invention is capable of discharging liquids from side holes 330. As previously noted, the prior art, as embodied in the ArgonCleaner XT, teaches a distal end hole which dispenses liquid and a cable to macerate clots. Said prior art results in one-sided reduction of clots leading to vessel collapse assisted with creation of a vacuum.

Mechanisms for Retracting the Filter—Magnetic System and Ring Sheath System

Figure 10A:
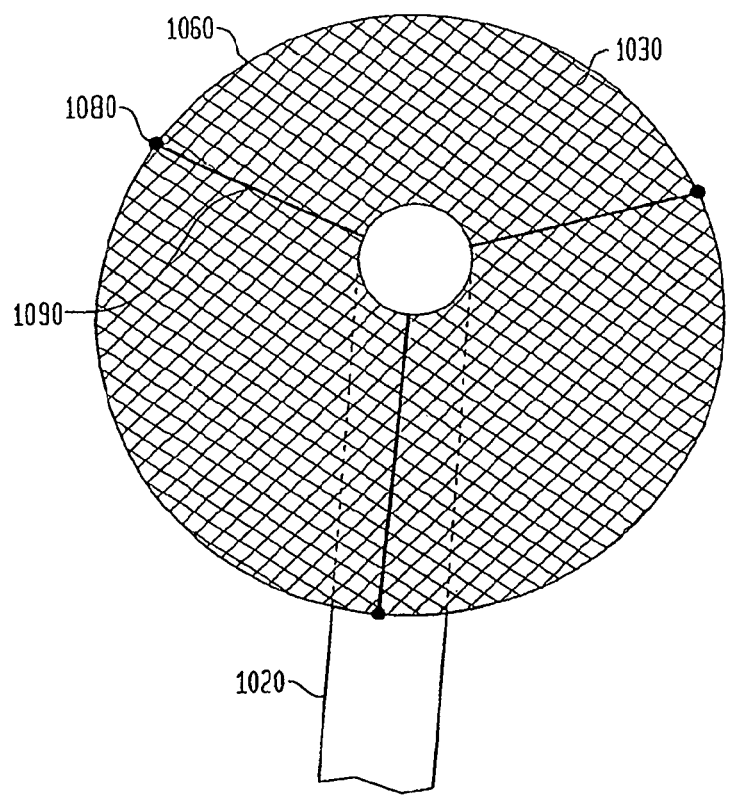
FIG. 10A shows a perspective view of one embodiment of the endovascular device of the described invention.
Figure 10B:
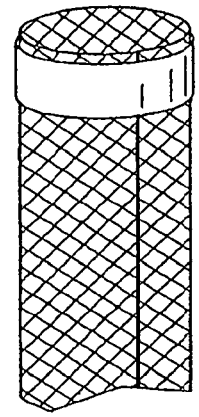
FIG. 10B shows a perspective view of one embodiment of the endovascular device of the described invention.

According to some embodiments, as depicted in FIGS. 10A and 10B, the semi-permeable filter 1030 can be compressed so that the edge 1060 is less than or equal to the diameter of the aspiration catheter 1020. According to some embodiments, the edge 1060 of the semi-permeable filter 1030 further comprises a magnet component 1080. According to some embodiments, the magnet component is connected to one or more wires 1090, which run the length of the aspiration catheter 1020 to a power source outside of the patient's body. According to some embodiments, the magnetic component 1080 comprises a solenoid, comprising a conductive wire 1090 coiled around a ferromagnetic metal, which can produce a magnetic field to attract one or more magnetic components by passing a current through the wire 1090. According to some embodiments, the magnetic component comprises a first magnetic component comprising a straight or curved ferromagnetic metal bar wrapped in an insulated copper wire, a second magnetic component comprising a ferromagnetic metal, and a third magnetic component comprising a ferromagnetic metal. According to some embodiments, when current is passed through the insulated copper wire wrapped around the metal bar, a magnetic field is produced around the first magnetic component, which attracts the second magnetic component and third magnetic component. According to some embodiments, the force of magnetic attraction between the magnetic components is strong enough to overcome the intrinsic resilience of the semi-permeable filter 1030 to maintain a flared shape, resulting in a collapse of the filter 1030.

According to some embodiments, the semi-permeable filter comprises a plurality of magnetic components comprising a conductive wire coiled around a ferromagnetic metal. According to some embodiments, the semi-permeable filter comprises a plurality of magnetic components comprising a ferromagnetic metal without a coiled wire. According to some embodiments, the semi-permeable filter comprises a plurality of magnetic components arranged in a manner adapted to collapse the semi-permeable filter such that no part of the semipermeable filter comprises a diameter greater than the diameter of the aspiration catheter.

According to some embodiments, the semi-permeable membrane comprises solenoids with magnetic poles approximately parallel to the surface of the semi-permeable membrane. According to some embodiments, the semi-permeable membrane comprises a first magnetic component comprising a solenoid arranged opposite to a second solenoid, wherein a current is passed through the coiled wire of each solenoid, and the resulting magnetic fields have opposing poles across the semi permeable membrane. For example, for a semi-permeable membrane comprising two solenoids, the solenoids are arranged so that the north pole of the first solenoid is opposite to the south pole of the second solenoid, and the south pole of the first solenoid is opposite to the north pole of the second solenoid. Thus, in this specific example, the opposite poles will attract one another across the distance of the semi-permeable membrane, thus collapsing the semi-permeable membrane.

According some embodiments, the solenoids are arranged so that the opposing poles of the solenoid are perpendicular to the semi-permeable membrane. According to some embodiments, the semi-permeable membrane comprises a first magnetic component comprising a solenoid perpendicular to the semi-permeable membrane arranged opposite to a second solenoid perpendicular to the semi-permeable membrane. For example, the north pole of the first solenoid is pointed toward the inner space defined by the semi-permeable membrane, and the south pole of the second solenoid is pointed toward the inner space defined by the semi-permeable membrane. Thus, in this specific example, the opposite poles will be attracted to one another across the distance of the semi-permeable membrane, thus collapsing the semi-permeable membrane.

According to some embodiments, the semi-permeable membrane comprises magnetic components at varying distances from the aspiration catheter. For example, some embodiments may comprise a first pair of magnetic components in the distal edge of the semi-permeable membrane, a second pair of magnetic components approximately equidistance from the distal edge and the proximal edge of the semi-permeable membrane, and a third pair of magnetic components approximately equidistance from the second pair of magnetic components and the proximal edge of the semi-permeable membrane.

According to some embodiments, the semi-permeable membrane comprises magnetic components arranged in a manner adapted to fold the semi-permeable membrane into a shape where no part of the semi-permeable membrane falls outside the diameter of the aspiration catheter. According to some embodiments, the semi-permeable membrane comprising the magnetic components and aspiration catheter is introduced into the blood vessel of a patient with the magnetic fields of the magnetic component holding the semipermeable membrane in a folded position, and upon arriving at the desired position in the blood vessel the magnetic field is turned off and the intrinsic resilience of the semi-permeable membrane unfolds the semi-permeable membrane into a flared shape. According to some embodiments, the semi-permeable membrane is re-folded by turning on the magnetic field of the magnetic components prior to removing the aspiration catheter and semi-permeable membrane from the blood vessel.

According to some embodiments (FIGS. 11A, 11B), a semi-permeable membrane can be expanded to a flared shape or collapsed into a folded shape via movement of a rigid ring 1090 structure positioned outside of the semi-permeable filter 1030. According to some embodiments, the semi-permeable filter is connected to the aspiration catheter 1020 below the rigid ring 1090. According to some embodiments, the rigid ring 1090 can be pushed out of the end of the aspiration catheter, forcing the semi-permeable filter 1030 to collapse. According to some embodiments, the rigid ring 1090 can be connected to a stiff wire 1100. According to some embodiments, the stiff wire can push the rigid ring 1090 out of the aspiration catheter to surround and collapse the semi-permeable filter 1030.

According to some embodiments, as depicted in FIGS. 11A, 11B, 13A and 13B, a semi-permeable membrane can be expanded or collapsed into a folded shape via movement of a rigid ring structure 1091 that extends from the aspiration catheter. According to some embodiments, the filter 1030 is attached to the inside of the aspirating end of the aspiration catheter 1020 and the rigid ring structure 1091 abuts the aspirating end of the aspirating catheter, acting as an extension of the aspirating catheter. According to some embodiments, the rigid ring structure can be advanced over the filter 1030 by being pushed by one or more stiff wires 1100. According to some embodiments, the rigid ring 1091 does not reduce the cross-sectional area through which aspiration occurs.

According to some embodiments, as depicted in FIGS. 12A and 12B, the aspiration catheter 1020 can be housed within an outer catheter 1110. According to some embodiments, the outer diameter of the aspiration catheter 1020 can be approximately equal to the inner diameter of the outer catheter 1110. According to some embodiments, the inner aspiration catheter 1020 can move independently within the outer catheter 1110. According to some embodiments, the outer catheter 1110 is rigid enough such that the semi-permeable filter is forced to collapse when the inner aspiration catheter 1020 is withdrawn inside the outer catheter 1110.

According to some embodiments of the present invention, using the filter-tip aspiration catheter device, the vein or artery is accessed downstream from the clot, and the filter-tip aspiration catheter is deployed downstream from the clot. This is usually easy to accomplish in most venous thrombi and emboli. This is usually not possible for arterial emboli in the brain. But in some arm and leg cases it can be. A non-limiting example is an axillary artery embolus/thrombus, where a person of ordinary skill can get access proximal to the clot from femoral insertion, and/or a person of ordinary skill in the art can access distally (downstream) via a brachial artery or radial artery access as well.

According to one aspect of the present invention, one or more embodiments of the apparatuses shown and described are used for one or more of irrigation, maceration, and aspiration of a blockage in a patient's blood vessel.

Method 1: Irrigation and Maceration Only

For example, according to some embodiments, a method of irrigating and macerating a blockage of a blood vessel comprises introducing a rotating, irrigating catheter into the blood vessel of a patient, advancing the catheter to the site of a blockage, penetrating the blockage with the catheter, macerating the blockage by rotating the catheter and irrigating within and beyond the blockage with the catheter. According to some embodiments, the maceration and irrigation can be constant. According to some embodiments, the maceration is constant while the irrigation is intermittent. According to some embodiments the maceration is intermittent while the irrigation is constant. According to some embodiments, the maceration and irrigation are both intermittent. According to some embodiments, the maceration and irrigation occur simultaneously. According to some embodiments, the maceration and irrigation occur asynchronously. Irrigation is sufficient to keep the vessels from collapsing.

Method 2: Only Irrigation and Aspiration

According to some embodiments, a method of removing a blockage in a blood vessel comprises introducing an irrigating catheter and an aspiration catheter into the blood vessel of a patient, advancing the irrigating and aspirating catheters to the site of a blockage, penetrating the blockage with the irrigating catheter, aspirating the blockage, and irrigating the blockage. According to some embodiments, the blockage comprises cells, cell debris, emboli, or other material, or a combination thereof. According to some embodiments, the aspiration is constant and the irrigation is constant. According to some embodiments, the aspiration is intermittent and the irrigation is intermittent. According to some embodiments, the aspiration is intermittent and the irrigation is constant. According to some embodiments, the aspiration is constant and the irrigation is intermittent. According to some embodiments, the aspiration and irrigation occurs simultaneously. According to some embodiments, the aspiration and irrigation occurs asynchronously. The present invention uses irrigation and aspiration to reverse blood flow while maintaining sufficient vascular volume and pressure to prevent the vessel from collapsing. This use of the present invention is independent of maceration.

Method 3: Maceration, Irrigation, and Aspiration

According to some embodiments, a method of removing a blockage in a blood vessel comprises introducing a macerating, irrigating catheter and an aspiration catheter into the blood vessel of the patient, advancing the irrigating and aspirating catheters to the site of a blockage, penetrating the blockage with the macerating, irrigating catheter, macerating the blockage, irrigating the blockage, and aspirating the blockage. According to some embodiments, the blockage comprises cells, cell debris, emboli, or other material, or a combination thereof. According to some embodiments, the aspiration, maceration, and irrigation are constant. According to some embodiments, the aspiration, maceration, and irrigation are intermittent. According to some embodiments, the aspiration is constant while the maceration and irrigation are intermittent. According to some embodiments, the aspiration and the maceration are constant while the irrigation is intermittent. According to some embodiments, the aspiration and irrigation is constant while the maceration is intermittent. According to some embodiments, the irrigation is constant while the maceration and aspiration are intermittent. According to some embodiments, two or more of the aspiration, irrigation, and maceration occurs simultaneously. According to some embodiments, two or more of the aspiration, irrigation, and maceration occurs asynchronously. The present invention can be used with or without a balloon (said balloon is any intentionally employed blood-flow blocking device). Said blood-flow blocking device may partially or completely block blood flow. The objective of using said blood-flow blocking device is to assist the present invention in reversing blood flow.

Method 5: Combining any Combination of Methods 1, 2, and 3, with a Clot Retrieval Device, a Non-Limiting Example of which is a Retrievable Stent Such a Solitaire (Medtronic) or Trevo (Stryker) Device.

According to some embodiments, a method of removing a blockage in a blood vessel comprises introducing a first device to the site of the blockage to break up the blockage, and introducing a second device at a site away from site of the blockage to capture emboli resulting from breaking up the blockage. According to some embodiments, the blockage comprises cells, cell debris, emboli, or other material, or a combination thereof. According to some embodiments, fragments of the blockage that travel in the direction of blood flow can be collected by a semi-permeable filter away from the site of the blockage. According to some embodiments, the emboli can be removed via aspiration at the site of the blockage, via an aspiration catheter with an embedded filter extending from its end, with or without additional irrigation and/or maceration elements at the site of aspiration. Aspiration can be applied to clear filters when debris builds up on said filters.

According to some optional embodiments of the present invention, an intravenous ultrasound (IVUS) is deployed to monitor blood flow rate through said filter. The purpose of inserting an intravenous ultrasound (IVUS) is to monitor blood flow rate through said filter clear so that in the event a blood clot build-up occurs on the surface of said filter and said blood clot build up slows blood flow by more than eighty percent (80%), then action is taken to remove said blood clot build up. Said removal is typically executed by using an aspirator.

Figure 14:
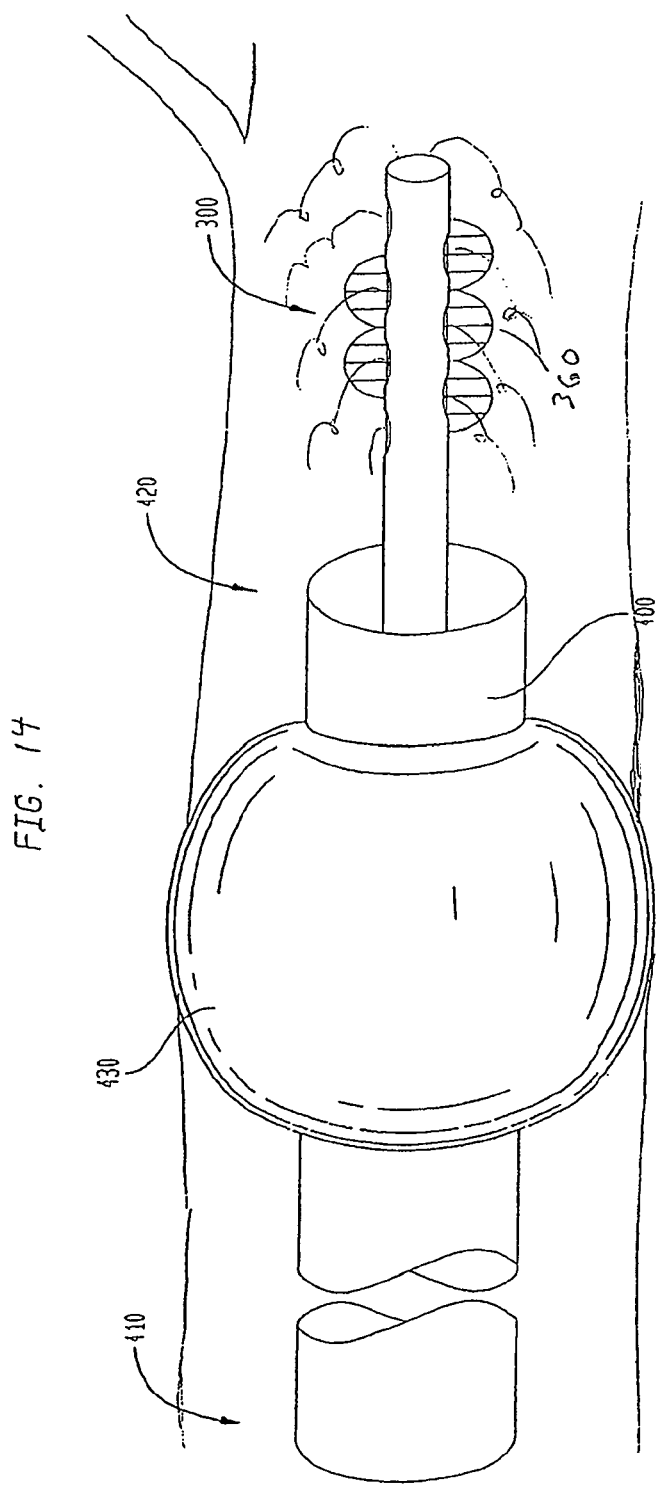
FIG. 14 shows a cross section side view of one embodiment of a balloon disposed upon the simultaneous aspirating, irrigating, macerating microcatheter of the current invention, further depicting reversal of blood flow distal to the balloon mounted aspiration catheter.

The sinusoidal, hypotube device of the current invention (such as depicted in FIG. 9) uses an eggbeater-like effect to macerate while simultaneously irrigating. The present invention is distinct from the prior art wherein a sinusoidal cable is used but cannot irrigate into and beyond the clot. The sinusoidal microtube of the present invention can vary enormously from a diameter of about 100 mm (four inches) down to approximately 0.1 mm. Referring now to FIG. 14, the present invention can be used in conjunction with balloons. Said balloon is mounted on aspiration catheter designed for use at the face of an arterial thrombus, in order to occlude a vessel and facilitate blood-flow reversal via aspiration and simultaneous distal irrigation. The present invention also teaches the use of vibrational wire, balloon and aspirator element with or without filters.

Figure 15:
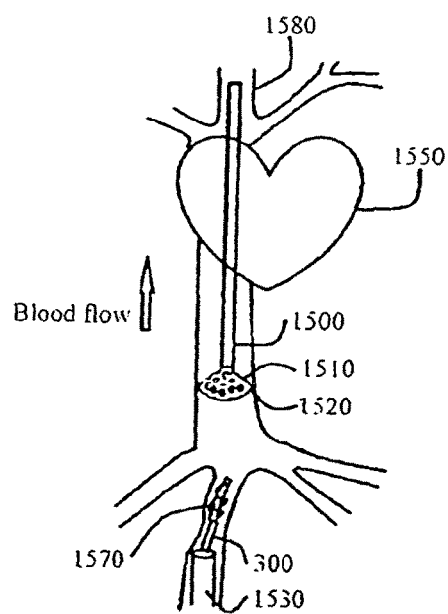
FIG. 15 shows a cross section side view of one embodiment of the simultaneous, irrigating, macerating microcatheter of the current invention inserted through the femoral vein disposed at the site of an iliac clot, further depicting a filter-tip aspiration catheter inserted into the inferior vena cava (IVC) to simultaneously catch thrombi released by the procedure.

Referring to FIG. 15, the simultaneous aspects of the current invention may be used in conjunction with the introduction of a second endovascular device, a filter-tipped aspiration catheter 1500 including at least one filter 1510 disposed at the distal tip of device 1500. Filter 1510 may optionally comprise a polyurethane membrane with pores, polyester, or other fabric or polymer, further supported by metal or other rigid wires, optionally nytinol. The pore size is 1 μm-250 μm, or 0.1 μm-5 mm (different unit intentional).

As depicted in FIG. 15, the rotating irrigation macerating catheter 300 is introduced via femoral vein sheath 1530 to the site of iliac clot 1570. Said aspiration catheter 1500 is introduced via the jugular vein 1580 through the heart 1550 from the opposite direction of blood flow to a position in the inferior vena cava (IVC) 1520 beyond the heart to catch emboli in deployed filter 1510. The perimeter of deployed filter 1510 is proximal to and within the IVC 1520. Blood flows in the direction of the heart 1550, into filter 1510 potentially carrying particulate matter freed up by the simultaneous irrigation into and maceration of the clot. Filter 1510 captures smaller particulate matter than wire structures used in the prior art, more effectively protecting the heart 1550 and other organs from the effect of small and medium sized emboli. Its use also eliminates the significant risks of deploying and removing said wire filter sometimes used in the prior art.

Figure 16:
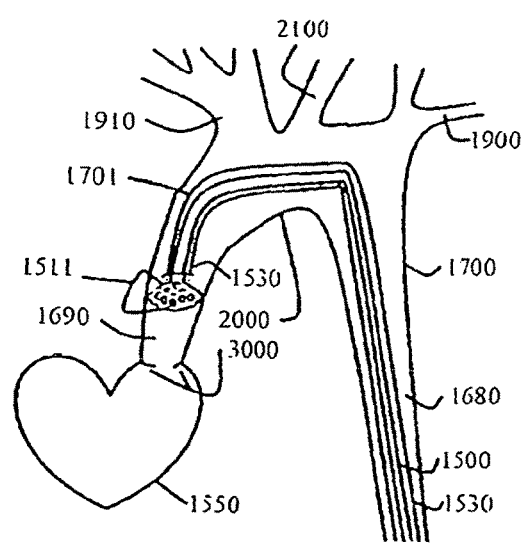
FIG. 16 shows an alternative embodiment of the current invention wherein an aspiration catheter may be introduced via the descending aorta.

In an alternative embodiment shown in FIG. 16, said aspiration catheter 1500 may be introduced via the descending aorta 1680. Said catheter 1500 has at least one bend. In FIG. 16, a first bend 1700 and a second bend 1701 are illustrated. All optional bends are positioned between filter 1510 and the terminus of catheter 1500 outside the body. In the preferred embodiment, said first bend 1700 occurs proximal to the left subclavian artery 1900, but not further than a line defined by the high point of aortic arch 2000 and the most proximal opening of the left carotid artery 2100. Said second bend 1701 occurs after the line defined by the uppermost point 2000 of the aortic arch and the most proximal opening of the left common carotid artery 2001, and proximal to the innominate artery 1910. In the preferred embodiment, filter 1510 is disposed within the ascending aorta 1690. In an optional embodiment, aspiration catheter 1500 is sheathed in outer sheath 1531 for a filter-tip aspiration catheter.

The dimensions of the present invention are as follows: the length of device 1500 is approximately 0.5-160 cm; the diameter of catheter 1500 is approximately 0.1 mm-25 mm, and the diameter of the at least one filter 1510 is approximately 0.1 mm-100 mm. In the preferred embodiment of the present invention filter 1510 is self-expanding. In an alternative embodiment, filter 1510 is expanded as a result of a balloon (not shown) expanding proximal to at least one filter 1510.

In an optional embodiment of the present invention, said at least one filter 1510 may also optionally comprise hydrogel (not shown) disposed upon the peripheral edges 1511 of said filter(s) 1510. In other optional embodiment, surfaces of the present invention likely to contact a vessel wall when deployed, such as first bend 1700 in FIG. 16, will also have a coating of hydrogel. The deployment of hydrogel as detailed above is intended to improve wall adherence such as at the site of bend 1700, and/or prevent "endoleaks" of unfiltered blood between filter 1510 and a vessel wall (as described in claims 10 and 17 of U.S. Pat. No. 9,775,730 B1 [Walzman]).

For example, one example of how the device of the present invention may be used during a heart valve-replacement procedure is as follows. The method includes the steps of delivering the present invention via a femoral artery (not shown), over aortic arch 2000, so that filter 1510 and catheter tip is facing aortic valve 3000 within the ascending aorta 1690—between the heart (aortic valve 3000) and the innominate artery 1910.

The next steps of the method include deployment of said at least one filter 1510, by delivering a replacement valve (not shown) into aortic valve 3000 and deploying said valve 300, through the "filter-tip guide catheter"—with filter 1510 capturing all emboli and protecting all three of the "Great Vessels" (the innominate artery 1910, left common carotid artery 2100, and left subclavian artery 1900, and their distal circulations), and the entire arterial supply to the body, from emboli that can be displaced during the procedure. Existing prior art such as Claret Medical's Sentinel® Cerebral Protection System, protects only two of the Great Vessels, omitting the left subclavian 1900. After deploying said replacement valve, the delivery system is removed. The filter-tip aspiration catheter 1500 can then optionally be aspirated. The filter-tip 1510 is then resheathed. All catheters and sheaths are then removed. Hemostasis is achieved by the practitioner's method of choice (using standard techniques).

Figure 17:
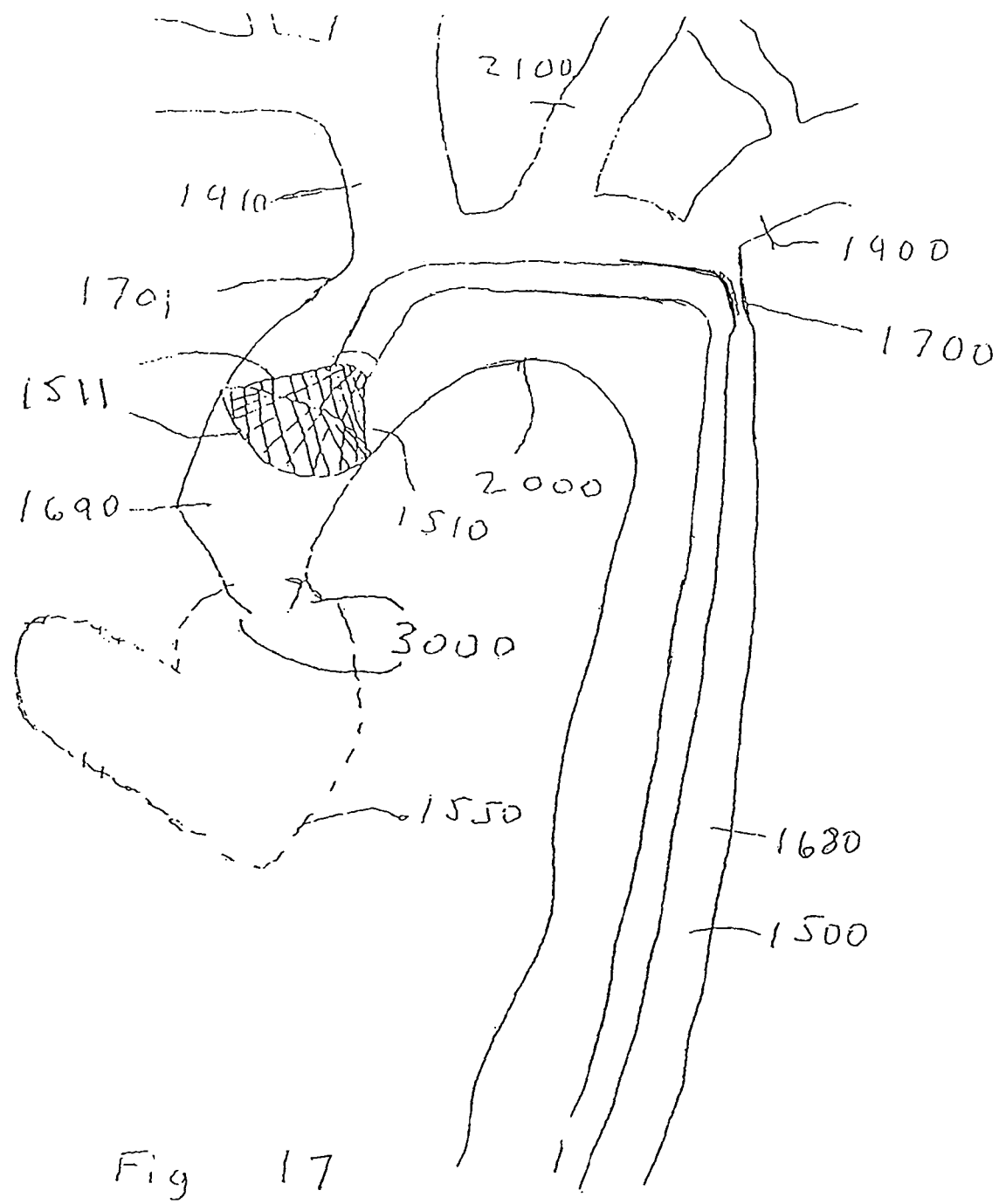
FIG. 17 shows an alternative embodiment of the current invention wherein a filter-tipped catheter has no sheath.

In an alternative embodiment shown in FIG. 17, said aspiration catheter 1500 may be introduced via the descending aorta 1680. Said catheter 1500 has at least one bend. In FIG. 17, a first bend 1700 and a second bend 1701 are illustrated. All optional bends are positioned between filter 1510 and the terminus of catheter 1500 outside the body. In the preferred embodiment, said first bend 1700 occurs proximal to the left subclavian artery 1900, but not further than a line defined by the high point of aortic arch 2000 and the most proximal opening of the left carotid artery 2100. Said second bend 1701 occurs after the line defined by the uppermost point 2000 of the aortic arch and the most proximal opening of the left common carotid artery 2001, and proximal to the innominate artery 1910. In the preferred embodiment, filter 1510 is disposed within the ascending aorta 1690. In an optional embodiment, aspiration catheter 1500. It should be noted that this embodiment differs from the embodiment of FIG. 16 in that it lacks outer sheath 1531.

An endovascular device for protecting the outflow through the ascending aorta by capturing emboli is capable of protecting more than the three great heart vessels simultaneously. In the preferred embodiment, the present invention incorporates an external sheath comprising a proximal end, a wall that comprises a circumference and that spans the proximal end to a distal end, wherein the wall of the catheter defines a luminal space, a first opening at the proximal end of the catheter, and a second opening at the distal end of the catheter. Said sheath is capable of both designed to allow smooth passage of surgical instruments as well as for positioning of said instruments.

The present invention also includes an external termination device such as a Luer Lock, diaphragm, valve among other device which were previous disclosed in the specification. Said device is attached to the proximal end of said external sheath. Such a device may also be attached to the proximal end of said inner catheter.

It should be noted that the present invention's an inner catheter comprising a proximal end, a wall that comprises a circumference and that spans the proximal end to a distal end, wherein the wall of the catheter defines a luminal space, a first opening at the proximal end of the catheter, and a second opening at the distal end of the catheter. Said catheter is made of a range of polymers are used for the construction of catheters, including silicone rubber, nylon, polyurethane, polyethylene terephthalate (PET), latex, and thermoplastic elastomers.

The present invention includes at least one flared, semi-permeable filter adapted to allow passage of blood cells and serum and to capture emboli, said at least one semi-permeable filter circumferentially attached to the distal end of said catheter. Said flared filter is collapsible to accommodate delivery into an appropriate position in the ascending aorta, wherein the diameter of said filter, when expanded, is smallest at its proximal attachment to the tip of said inner catheter and larger at its distal segment, wherein when fully expanded the distal segment of said filter conforms to the walls of the ascending aorta, so that blood flowing through the ascending aorta travels through said filter.

It should also be noted that the present invention's inner catheter has an outer circumferential diameter that is not more than the inner diameter of said outer sheath; and the filter disposed on the distal end of said inner catheter is removably attached and deliverable through said external sheath, while remaining attached to said inner catheter. Additionally, the present invention is capable of joining additional devices can be delivered through said filter into the portion of the ascending aorta closet to the heart, the aortic valve, the heart, and/or cardiac vessels without displacing any portion of said filter.

The present invention has several additional embodiments including one which is detachably secured to an external aspiration device at its external termination device, to further facilitate removal of filtered debris. Other include embodiment with at least 1 bend and yet another with at least 2 bends.

The present intention also uses a filter which is self-expanding upon release from an external constraint. Said flexible filter comprises a flexible stent having a plurality of flexible wire segments attached across the ends of the stent. The filter is resiliently compressible for s insertion into a vessel and expands against the passageway upon placement therein. The filter includes different levels of filtration. This filter further comprises shape-memory polymers that cause it to expand over a set amount of time after introduction into the body.

Additionally, in a separate embodiment the filter expands in response to an additional stimulus. One such nonlimiting example is via a balloon expansion.

The present invention has additional capabilities, such as acting as a conduit for delivery of a cardiac valve device, acting as a conduit for delivery of a cardiac ablation device and acting as a conduit for delivery of a balloon.

The present invention also discloses various optional filter elements. These include: at least one filter comprises a membrane with pores; pores are differentially sized; said pores are less than 200 μM in size; at least one filter is supported by rigid wires; at least one filter is supported by semirigid wires; at least one filter is further supported by at least 1 rigid wire comprising at least 1 ring; at least one filter is further supported by at least 1 semirigid wire comprising at least 1 ring.

All of said filter wherein said wires may use nitinol. They may also have disposed upon the peripheral edges of said at least one filter.

In a separate embodiment of the present invention the device is composed of a catheter comprising a proximal end, a wall that comprises a circumference and that spans the proximal end to a distal end, wherein the wall of the catheter defines a luminal space, a first opening at the proximal end of the catheter, and a second opening at the distal end of the catheter; an external termination device (such as Luer Lock, diaphragm, valve-define in spec) attached to the proximal end of said catheter; at least one flared, semi-permeable filter adapted to allow passage of blood cells and serum and to capture emboli, said at least one semi-permeable filter circumferentially attached to the distal end of said catheter, wherein said flared filter is collapsible to accommodate delivery into an appropriate position in the ascending aorta, and wherein the diameter of said filter, when expanded, is smallest at its proximal attachment to the tip of said catheter and larger at its distal segment, wherein when fully expanded the distal segment of said filter conforms to the walls of the ascending aorta, so that blood flowing through the ascending aorta travels through said filter; and wherein additional devices can be delivered through said filter into the portion of the ascending aorta closet to the heart, the aortic valve, the heart, and/or cardiac vessels without displacing any portion of said filter This embodiment has many of the elements of the prior embodiment such as the fact that it is detachably secured to an external aspiration device at its external termination device, to further facilitate removal of filtered debris; may have either at least one (1) bend in said catheter or at least two (2) bends in said catheter; it is self-expanding upon release from an external constraint and may be comprised of shape-memory polymers that cause it to expand over a set amount of time after introduction into the body.

More specifically, the present invention discloses that the self-expanding devices can only expand when they are released from "all" constraints. Thus, the present invention is self-expanding upon release from all constraints. Such constraints may include, but are not limited to, an external sheath covering said filter, internal hooks, and/or a shortened circumferential string. Additionally, and/or alternatively, the filter(s) may be comprised of shape-memory polymers that cause it to expand upon the application of an additional stimulus, provided there are no physical constraints to expansion.

The present invention discloses two types of devices which are capable of opening and closing the lasso, which may be known as a rewinding mechanism. They are a ratchet and a reel. A ratchet mechanism the just grabs and pulls the string along a straight line is more likely than a spinning "reel" (similar to the mechanical detachment mechanism of Penumbra coils and EV3 coils, as well as (perhaps more-so) similar to the shortening mechanism of the Rapid Medical Comaneci and Tigertriever devices (https://www.rapid-medical.com/comaneci).

The present invention also discloses that "internal" constraints (i.e. constraints which are built into the present invention) such as hooks located inside of the present invention. The function of said internal constraints are the same as said external constraints (i.e. to constrain shape change).

The present invention may be used in the following manner comprising the steps of:
(a) inserting said external sheath of said device via a femoral artery,
(b) passing distal end of said external sheath over the aortic arch over a wire and/or an additional catheter, under fluoroscopic guidance,
(c) positioning said distal end of said external sheath into the ascending aorta
(d) removing said additional delivery wire and/or catheter
(e) delivering said filter-tipped inner catheter through said external sheath, optionally over an additional catheter and/or wire;
(f) positioning the distal segment of said filter so that the end of said filter extends to the end of said external sheath
(g) holding said inner catheter steady while said external sheath is partially withdrawn by the length of said filter, under fluoroscopic guidance, thereby exposing said filter within the ascending aorta, thus prompting said (self-expanding version) filter to expand to conform at its outer segment to the inner walls of the ascending aorta;
(h) delivering an aortic valve device across the aortic valve, optionally over a wire, via a delivery device detachably attached to said aortic valve
(i) deploying and detaching said aortic valve device;
(j) removing said aortic valve delivery device;
(k) optionally applying aspiration to said proximal end of the lumen of said filter-tip inner catheter
(l) advancing said external sheath while holding still said inner catheter, optionally with aspiration still applied, until the entire filter collapses into said external sheath
(m) withdrawing said entire device from the aorta, optionally with aspiration still applied, and removing it from the body; and
(n) obtaining femoral hemostasis.

The present invention discloses three additional features for the present invention. These include (a) an outer sheath, (b) at least one curve in the catheter, and (c) at least one detachable aspirator.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the described invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the described invention is not entitled to antedate such publication by virtue of prior invention. Further, the dates of publication provided may be different from the actual publication dates which may need to be independently confirmed.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

I claim:

1. A method of performing an endovascular procedure comprising:
   inserting an endovascular device into a patient's vasculature, the endovascular device including a first tubular member and a filter element supported by the first tubular member;
   deploying the filter element within the patient's vasculature;
   delivering a replacement valve to the patient's heart through the endovascular device; and collapsing the filter element within the patient's vasculature to facilitate removal of the endovascular device, wherein collapsing the filter element includes activating a lasso mechanism.

2. The method of claim 1, wherein inserting the endovascular device includes advancing the endovascular device through the patient's femoral artery and over the patient's aortic arch such that the filter element faces the patient's aortic valve within the patient's ascending aorta.

3. The method of claim 1, further comprising capturing emboli using the filter element to protect the patient's innominate artery, left common carotid artery, and left subclavian artery.

4. The method of claim 3, wherein capturing emboli using the filter element includes permitting blood cells and serum to pass through the filter element.

5. The method of claim 1, wherein collapsing the filter element includes sheathing the filter element with the first tubular member.

6. The method of claim 5, wherein deploying the filter element includes causing relative movement between the first tubular member and a second tubular member extending within the first tubular member.

7. The method of claim 6, wherein collapsing the filter element includes retracting the second tubular member into the first tubular member such that the filter element is sheathed within the first tubular member.

8. The method of claim 1, wherein activating the lasso mechanism includes retracting a lasso connected to the filter element, the lasso connected to a retraction mechanism for tensioning the lasso.

9. The method of claim 1, further comprising:
   connecting the endovascular device to an external aspirator; and
   applying aspiration to the endovascular device via the external aspirator to enhance removal of emboli from the patient's vasculature.

10. A method of performing an endovascular procedure comprising:
    inserting a first medical device into a patient's vasculature, the first medical device including a first tubular member and a filter element supported by the first tubular member;
    deploying the filter element;
    delivering a second medical device into the patient's vasculature through the first medical device; collapsing the filter element to facilitate removal of the first medical device, wherein collapsing the filter element includes activating a lasso mechanism; wherein the filter element is configured to capture emboli created during the endovascular procedure and the second medical device is a treatment device delivered into the patient's vasculature through the first tubular member and the filter element to deliver a replacement valve to a patient's heart.

11. The method of claim 10, further comprising treating a thrombus located upstream of the patient's heart using the second medical device.

12. The method of claim 10, wherein collapsing the filter element includes sheathing the filter element.

13. The method of claim 12, wherein sheathing the filter element includes covering the filter element with the first tubular member.

14. The method of claim 12, wherein sheathing the filter element includes retracting the filter element into first tubular member via a second tubular member extending within the first tubular member such that the second tubular member and the filter element are positioned within the first tubular member.

15. The method of claim 10, further comprising:
    connecting the first medical device to an external aspirator; and
    applying aspiration to the first medical device via the external aspirator to enhance removal of emboli from the patient's vasculature.

16. The method of claim 15, wherein applying aspiration includes applying aspiration continuously.

17. The method of claim 15, wherein applying aspiration includes applying aspiration intermittently.

18. The method of claim 10, further comprising:
    moving a second tubular member positioned concentrically relative to the first tubular member to facilitate delivery, deployment, and recapture of the filter element.

* * * * *